(12) United States Patent
Mason et al.

(10) Patent No.: US 10,302,592 B2
(45) Date of Patent: May 28, 2019

(54) PARTICLE SIZE DISTRIBUTION MEASUREMENTS OF PARTICLES AND DROPLETS USING OPTICAL GEL ELECTROPHORESIS

(71) Applicant: The Regents of the University of California, Oakland, CA (US)

(72) Inventors: Thomas G. Mason, Los Angeles, CA (US); Xiaoming Zhu, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 296 days.

(21) Appl. No.: 14/898,035

(22) PCT Filed: Jun. 13, 2014

(86) PCT No.: PCT/US2014/042378
§ 371 (c)(1),
(2) Date: Dec. 11, 2015

(87) PCT Pub. No.: WO2014/201401
PCT Pub. Date: Dec. 18, 2014

(65) Prior Publication Data
US 2016/0123924 A1    May 5, 2016

Related U.S. Application Data

(60) Provisional application No. 61/834,632, filed on Jun. 13, 2013.

(51) Int. Cl.
*G01N 27/453* (2006.01)
*G01N 27/447* (2006.01)
(Continued)

(52) U.S. Cl.
CPC ... *G01N 27/44721* (2013.01); *G01N 15/0266* (2013.01); *G01N 27/44747* (2013.01);
(Continued)

(58) Field of Classification Search
CPC ....... G01N 27/44704; G01N 27/44721; G01N 27/453
See application file for complete search history.

(56) References Cited

U.S. PATENT DOCUMENTS 4,181,594 A * 1/1980 Rizk ................. G01N 27/44717
                                                204/613
4,994,166 A * 2/1991 Fernwood .......... G01N 27/4473
                                                204/614
(Continued)

OTHER PUBLICATIONS

Pellegrino et al., "Gel Electrophoresis of Gold-DNA Nanoconjugates," Journal of Biomedicine and Biotechnology, vol. 2007, article ID 26796, 9 pages (Year: 2007).*
(Continued)

*Primary Examiner* — Alexander S Noguerola
(74) *Attorney, Agent, or Firm* — Venable LLP; Henry J. Daley; Miguel A. Lopez

(57) ABSTRACT

A device for measuring size distributions of particles and droplets includes a gel electrophoresis component that has a gel chamber that is suitable to receive a gel in which at least one of particles or droplets propagate in a liquid medium during operation; an illumination source arranged to illuminate said at least one of particles or droplets such that the at least one of particles or droplets absorbs, scatters or emits light; an imaging device configured to obtain image data from the absorbed, scattered, or emitted light from the at least one of particles or droplets while the at least one of particles or droplets propagate through the gel; and a computing device configured to receive and process the image
(Continued)

data to provide information concerning a size distribution of the at least one of particles or droplets.

20 Claims, 16 Drawing Sheets

(51) Int. Cl.
   *G01N 15/02* (2006.01)
   *G01N 15/00* (2006.01)
(52) U.S. Cl.
   CPC . *G01N 27/44778* (2013.01); *G01N 27/44726* (2013.01); *G01N 2015/0038* (2013.01)

(56) References Cited

U.S. PATENT DOCUMENTS

| | | | |
|---|---|---|---|
| 4,999,340 | A | 3/1991 | Hoffman et al. |
| 5,013,420 | A | 5/1991 | Schuette |
| 5,455,344 | A * | 10/1995 | Harper ............... C08L 5/00 536/123.1 |
| 5,748,491 | A * | 5/1998 | Allison ............ G06K 9/00503 702/190 |
| 2005/0148100 | A1 | 7/2005 | Su et al. |
| 2007/0278102 | A1 | 12/2007 | Hayashida et al. |
| 2009/0277791 | A1 | 11/2009 | Vu et al. |
| 2010/0140090 | A1* | 6/2010 | Kelly .................... B01D 57/02 204/461 |

OTHER PUBLICATIONS

Eychmüller et al., Photochemistry of Semiconductor Colloids. 35. Size Separation of Colloidal CdS by Gel Electrophoresis, Langmuir 1990, 6, 1605-1608.*
Corredig et al., "Characterization of the interface of an oil-in-water emulsion stabilised by milk fat globule membrane material," Journal of Diary Research (1998) 65, 405-477.*
Roy et al., "Size dependent optical characterization of semiconductor particle: CdS embedded in polymer matrix," Indian J. Phys. 84 (19), 1405-1411 (2010).*
Adamson, N. J.; Reynolds, E. C., Rules Relating Electrophoretic Mobility, Charge and Molecular Size of Peptides and Proteins. J. Chromatogr. B 1997, 699, 133-147.
Amann, W. Ludwig, K.H. Schleifer, Microbiol. Rcv. 59 (1995) 143.
Amsterdam, Z. Erel, S. Shaltiel, Arch. Biochem. Biophys. 171 (1975) 673.
Araki, Bull. Chem. Soc. Jpn. 29 (1956) 543.
Arnott, A. Fulmer, W.E. Scott, I.C.M. Dea, R. Moorhouse, D.A. Rees, J. Mol. Biol. 90 (1974) 269.
Attwood, B.J. Nelmes, D.B. Sellen, Biopolymers 27 (1988) 201.
Aymard, D.R. Martin, K. Plucknett, T.J. Foster, A.B. Clark, 1.T. Norton, Biopolymers 59 (2001) 131.
Behrens, S. II.; Christi, D. I.; Emmerzael, R.; Schurtenberger, P.; Borkovec, M., Charging and Aggregation Properties of Carboxyl Latex Particles: Experiments Versus Dlvo Theory. Langmuir 2000, 16, 2566-2575.
Blake, K.H. Johnston, G.J. Russelljones, E.C. Gotschlich, Anal. Biochem. 136 (1984) 175.
Boffey, in J.M. Walker, Methods in Molecular Biology, Humana, Totowa, NJ, 1984, p. 333.
Brody, J. R.; Kern, S. E., History and Principles of Conductive Media for Standard DNA Electrophoresis. Anal. Biochem. 2004, 333, 1-13.
Burnette, Anal. Biochem. 112 (1981) 195.
Calladine, C.M. Collis, H.R. Drew, M.R. Mott, J. Mol. Biol. 221 (1991) 981.
Cebron A Fau—Coci, J. Coci M Fau—Gamier, H.J. Gamier J Fau—Laanbroek, H.J. Laanbroek, Appl. Environ. Microbiol. 70 (2004) 6726.
Chevallet, S. Luche, T. Rabilloud, Nat. Protoc. 1 (2006) 1852.
Chui, R.J. Phillips, M.J. McCarthy, J. Colloid Interface Sci. 174 (1995) 336.
Clark, J.H. Lunacek, G.B. Benedek, Am. J. Phys. 38 (1970) 575.
Connolly, M. Singh, C.E. Buckley, Physica B: Condens. Matter 350 (2004) 224.
de Boer, C. de Weerd, D. Thoenes, H.W.J. Goossens, Part. Part. Syst. Charact. 4 (1987) 14.
DeBlois, C.P. Bean, Rcv. Sci. Instrum. 41 (1970) 909.
DePhillips, A.M. Lenhoff, J. Chromatogr. A 883 (2000) 39.
Derjaguin, B.; Landau, L., Theory of Stability of Highly Charged Liophobic Sols and Adhesion of Highly Charged Particles in Solutions of Electrolytes. Zhurnal Eksperimentalnoi Teor. Fir. 1945, 15, 663-682.
Derjaguin, B.; Landau, L., Theory of Stability of Strongly Charged Liophobic Sols and of the Adhesion of Strongly Charged-Particles in Solutions of Electrolytes. Prog. Surf. Sci. 1993, 43, 30-59.
Diez, J. Anton, N. Guixa-Boixereu, C. Pedros-Alio, F. Rodriguez-Valera, Int. Microbiol. 3 (2000) 159.
Djabourov, A.H. Clark, D.W. Rowlands, S.B. Rossmurphy, Macromolecules 22 (1989) 180.
Fangman, Nucleic Acids Res. 5 (1978) 653.
Fatin-Rouge, K. Starchev, J. Buffle, Biophys. J. 86 (2004) 2710.
Gisler, T.; Schulz, S. F.; Borkovec, M.; Sticher, H.; Schurtenberger, P.; D,A6Aguanno, B.; Klein, R., Understanding Colloidal Charge Renormalization from Surface Chemistry: Experiment and Theory. J. Chem. Phys. 1994, 101, 9924-9936.
Granzier, K. Wang, Electrophoresis 14 (1993) 56.
Griess, K.B. Guiseley, P. Serwer, Biophys. J. 65 (1993) 138.
Guarrotxena, G. Braun, J. Nanopart. Res. 14 (2012) 1199.
Hanauer, S. Pierrat, I. Zins, A. Lotz, C. Sonnichsen, Nano Lett. 7 (2007) 2881.
Hasenoehrl, C.M. Alexander, N. N. Azzarelli, J.C. Dabrowiak, Electrophoresis 33 (2012) 1251.
Hasse, F. Scholz, J. Solid State Electrochem. 10 (2006) 380.
Hjerten, Arch. Biochem. Biophys. 99 (1962) 466.
loannidis. Manufacturing of Agarose-Based Chromatographic Media with Controlled Pore and Particle Size. Ph.D. Thesis, University of Birmingham, Birmingham, 2009.
Johnson, L.I. Grossman, Biochemistry 16 (1977) 4217.
Klodzinska, B. Buszewski, Anal. Chem. 81 (2008) 8.
Knox, H.J. Ritchie, J. Chromatogr. 387 (1987) 65.
Kostal, E.A. Arriaga, Electrophoresis 29 (2008) 2578.
Kowalczyk, I.n. Lagzi, B.A. Grzybowski, Curr. Opin. Colloid Interface Sci. 16 (2011) 135.
Kremser, D. Blaas, E. Kenndler, Electrophoresis 30 (2009) 133.
Kusukawa, M.V. Ostrovsky, M.M. Garner, Electrophoresis 20 (1999) 1455.
Lahaye, C. Rochas, Hydrobiologia 221 (1991) 137.
Laing, J. Immunol. Methods 92 (1986) 161.
Lee, A.R. Bahaman, Trop. Biomed. 27 (2010) 351.
Li, R.J. hill, J. Colloid Interface Sci. 394 (2013) 1.
Maaloum, N. Pernodet, B. Tinland, Electrophoresis 19 (1998) 1606.
Mackintosh, H.Y. Choi, S.H. Bac, D.A. Veal, P.J. Bell, B.C. Ferrari, D.D. Van Dyk, N. M. Verrills, Y.K. Paik, P. Karuso, Proteomics 3 (2003) 2273.
Mason, J.N. Wilking, K. Meleson, C.B. Chang, S.M. Graves, J. Phys.: Condens. Matter 18 (2006) R635.
Mason, S.M. Graves, J.N. Wilking, M.Y. Lin, Eur. Phys. J. B: Condens. Matter Phys. 9 (2006) 193.
Meleson, S. Graves, T.G. Mason, Soft Mater. 2 (2004) 109.
Merril, Methods Enzymol. 182 (1990) 477.
Mohammed, M.W.N. Hember, R.K. Richardson, E.R. Morris, Carbohydr. Polym. 36 (1998) 15.
Narayanan, X. Jun-Ying, L. Xiang-Yang, J. Phys.: Conf. Ser. 28 (2006) 83.
Nedelec, J.-P.E. Grolier, M. Baba, J. Sol-Gel Sci. Technol. 40 (2006) 191.
Nucci, J.M. Vanderkooi, J. Mol. Liq. 143 (2008) 160.
Pellegrino, R.A. Sperling, A.P. Alivisatos, W.J. Parak, J. Biomed. Biotechnol. (2007) 26796.
Pernodet, M. Maaloum, B. Tinland, Electrophoresis 18 (1997) 55.
Pluen, P.A. Netti, R.K. Jain, D.A. Berk, Biophys. J. 77 (1999) 542.

(56) References Cited

OTHER PUBLICATIONS

Pollard in: J. Walker, Ed. The Protein Protocols Handbook; Humana Press, 1996, p. 121.
Rees, Biochem. J. 126 (1972) 257.
Ruchel, R.L. Steere, E.F. Erbe, J. Chromatogr. 166 (1978) 563.
Schagger, G. Vonjagow, Anal. Biochem. 166 (1987) 368.
Serwer, S.A. Khan, G.A. Griess, J. Chromatogr. A 698 (1995) 251.
Shapiro, E. Vinuela, J.V. Maize], Biochem. Biophys. Res. Commun. 28 (1967) 815.
Sparks, D. L.; Phillips, M. C., Quantitative Measurement of Lipoprotein Surface Charge by Agarose Gel Electrophoresis. J. Lipid Res. 1992, 33, 123-130.
Subir, M.; Liu, J.; Eisenthal, K. B. Protonation at the Aqueous Interface of Polymer Nanoparticles with Second Harmonic Generation. J. Phys. Chem. C 2008, 112, 15809-15812.
Surugau, P.L. Urban, J. Sep. Sci. 32 (2009) 1889.
Tako, S. Nakamura, Carbohydr. Res. 180 (1988) 277.
Tung, J. S.; Knight, C. A., Effect of Charge on the Determination of Molecular Weight of Proteins by Gel Electrophoresis in Sds. Biochem. Biophys. Res. Commun. 1971, 42,1117-1121.
Unlu, M.E. Morgan, J.S. Minden, Electrophoresis 18 (1997) 2071.
Verwey, E. J. W.; Overbeek, J. T. G., Theory of the Stability of Lyophobic Colloids; Elsevier: Amsterdam, 1948.
Vincent, B.W. Marisa, A. Kramer, K. Kroy, M.A.K. Williams, New J. Phys. 15 (2013) 035002.
Voytas, N. Ke, in: Current Protocols in Molecular Biology; John Wiley & Sons, Inc., 2001.
Waki, J.D. Harvey, A.R. Bellamy, Biopolymers 21 (1982) 1909.
Waring, J. Mol. Biol. 13 (1965) 269.
Weber, M. Osborn, J. Biol. Chem. 244 (1969) 4406.
Weiss, H.N. Frock, Powder Technol. 14 (1976) 287.
Williams, Biotech. Histochem. 76 (2001) 127.
Wray, T. Boulikas, V.P. Wray, R. Hancock, Anal. Biochem. 118 (1981) 197.
Yao, A.M. Lenhoff, J. Chromatogr. A 1037 (2004) 273.
Zhao, M.; Sun, L.; Fu, X.; Gong, X., Influence of Ionic Strength, Ph, and Sds Concentration on Subunit Analysis of Phycoerythrins by Sds-Page. Appl. Biochem. Biotechnol. 2010, 162, 1065-1079.
Zhu, S.; Panne, U.; Rurack, K., A Rapid Method for the Assessment of the Surface Group Density of Carboxylic Acid-Functionalized Polystyrene Microparticles. Analyst 2013, 138, 2924-2930.
Zhu, T.G. Mason, "Passivated Gel Electrophoresis of Charged Nanospheres by Light-Scattering Video Tracking", J. Colloid Interface Sci. (accepted).
Zweig, S. Barban, N.P. Salzman, J. Virol. 17 (1976) 916.

\* cited by examiner $t = 0$ s    $t = 900$ s    $t = 1800$ s $t = 0$ s    $t = 900$ s    $t = 1800$

PARTICLE SIZE DISTRIBUTION MEASUREMENTS OF PARTICLES AND DROPLETS USING OPTICAL GEL ELECTROPHORESIS

CROSS-REFERENCE OF RELATED APPLICATION

This application is a National Stage Application of International Application No. PCT/US2014/042378, filed on Jun. 13, 2014, which claims priority to U.S. Provisional Application No. 61/834,632 filed Jun. 13, 2013, the entire contents of each of which are hereby incorporated by reference.

BACKGROUND

1. Field of Invention

The field of the currently claimed embodiments of this invention relates to systems, methods and compositions for the separation of nanoparticles and droplets through a gel and the visualization of such.

2. Discussion of Related Art

Gel electrophoresis (gel-EP) is a common technique used for separating, identifying, and purifying charged biopolymers, such as DNA [1-7], RNA [8], and proteins [9-19]. Gel-EP has been applied to a wide variety of other small-scale structures, including organelles, micro-organisms, bacteria [20-22], viruses [23-25], and nanoparticles [26-33]. For certain biological particles that are larger than the characteristic pore size of the gel, capillary electrophoresis [34-36] has been used rather than classical gel-EP. The most commonly used gel-EP methods include polyacrylamide gel-EP (PAGE) [37] and agarose gel-EP. Polyacrylamide gels are formed when monomers are polymerized and chemically cross-linked using a cross-linking agent, such as methylenebisacrylamide. PAGE is commonly used to separate protein molecules to a high degree of purity [38], because polyacrylamide gels typically have a suitably small pore size. By contrast, agarose gel-EP [39, 40] is more useful for separating larger biological molecules, but it typically offers less resolving power because the pore sizes are larger and more polydisperse. Despite this higher polydispersity, among commonly available gel materials, agarose can produce gels that have larger pore sizes that could be suitable for separating a wider range of larger nanoscale and colloidal objects.

Agarose is a linear polysaccharide polymer having a molecular weight of about 120,000 g/mol. In seaweed-derived agarose, small numbers of methyl, sulfate, and pyruvate groups are found substituting the free hydroxyl groups; consequently, at neutral pH, the gel is populated with charges resulting from these substituents [41, 1]. Agarose powder dissolves in water at temperatures near 100° C. and solidifies into a gel (i.e. a "hydrogel") when it is cooled to room temperature [42]. During the gelation of agarose, the molecules change from random coils to double helices, which bundle together to form a rigid gel network [43-46]. The average pore size depends on the agarose type and various gelation conditions [47-49], such as ionic strength [48, 50] and thermal history [51], during and after gelation. To raise the average pore size, one can lower the agarose concentration, increase the ionic strength, and slow down the cooling rate. Interestingly, beyond its use in biochemistry and microbiology, agarose is also used as a clarifying (i.e. "fining") agent in brewing because of its ability to bind and trap certain kinds of small particulates that scatter light. While desirable in clarifying applications, such particle-gel binding could prevent the use of agarose in gel-EP of fine particles, such as nanoparticles.

The structures and pore size distributions of a wide range of agarose gels have been studied extensively by transmission electron microscopy [52-54], atomic force microscopy [50, 55], scanning electron microscopy, small angle neutron scattering [56, 57], small angle x-ray scattering [58], absorbance [59], nuclear magnet resonance [60], size-exclusion chromatography [61], inverse size exclusion chromatography [62, 63], templated electrodeposition[64], and thermoporosimetry [65]. Thus, methods of forming agarose gels having highly specific compositions and pore-size distributions are well known.

After electrophoretic separation, biological molecules are typically visualized using a variety of different staining agents and methods. For example, fluorescence from DNA molecules labeled using ethidium bromide can be seen when illuminated with ultraviolet (UV) light. Radioactive isotopes [66, 67] are also used to label biological macromolecules, yielding autoradiographs. Additionally, colorimetric dyes (e.g. Coomassie brilliant blue [68-73] and silver [74, 75]) and other fluorescent dyes have been used to visualize protein molecules. However, because most biological molecules in aqueous solution have relatively small optical scattering cross-sections, simple optical scattering from these molecules does not provide an easily measureable signal, especially given the significant background scattering from the gel. Yet, nanoscale particles that have a refractive index difference with respect to the buffer solution and also large enough overall dimensions, still adequately scatter visible light that could be readily detected. Dynamic light scattering (DLS) relies upon this scattering and is commonly used to measure average hydrodynamic diameters of monodisperse colloids, yet DLS faces a difficult ill-posed problem in turning time-dependent correlation functions into polydisperse distributions.

One would expect that the electrophoretic mobility of a compact, rigid, spherical particle propagating through a porous gel could be significantly different than that of an extensible, flexible, non-spherical biopolymer [76, 31]. Although gel-EP has been previously used to separate a variety of nanoscale objects under certain conditions, separations of model synthetic, monodisperse, charge-stabilized, spherical, polymer nanoparticles using passivated large-pore gel-EP has not been systematically studied. Interactions between the nanospheres and the gel can be important in gel-EP, not just in producing an effective viscous resistance that depends on the sizes of objects propagating through the gel, but also in elastic interactions between the gel and the particles, both in a quiescent condition and when driven. Whereas highly charged biopolymers, such as DNA, do not bind to common agarose gels at typical conditions in standard buffers, nanoparticles, which have a much larger size and a comparatively smaller overall charge density, could bind strongly to the gel. Moreover, sysetmatic measurements of how compact nanospheres having different radii and charges propagate in real-time through a porous gel during electrophoresis at different applied field strengths are still lacking.

SUMMARY

A device for measuring size distributions of particles and droplets according to some embodiments of the current invention includes a gel electrophoresis component that has a gel chamber that is suitable to receive a gel in which at least one of particles or droplets propagate in a liquid medium during operation; an illumination source arranged to illuminate said at least one of particles or droplets such that the at least one of particles or droplets absorbs, scatters or emits light; an imaging device configured to obtain image data from the absorbed, scattered, or emitted light from the at least one of particles or droplets while the at least one of particles or droplets propagate through the gel; and a computing device configured to receive and process the image data to provide information concerning a size distribution of the at least one of particles or droplets.

A device for separating particles or droplets in a bulk solution according to some embodiments of the current invention includes a gel electrophoresis component and a collection plate positioned at a surface of a gel that has a plurality of collection wells. The gel electrophoresis component includes a gel chamber that is suitable to receive the gel in which at least one of the particles or droplets propagates during operation. The gel electrophoresis component includes a first set of at least two electrodes opposing one another so as to create a first electric field following application of a first voltage, and a second set of at least two electrodes positioned opposing one another and perpendicular to the first set of at least two electrodes so as to create a second electric field following application of a second voltage wherein the second electric field is perpendicular to the first electric field.

A composition for producing a passivated gel according to some embodiments of the current invention includes a buffer, a polymer or amphiphilic surfactant to serve as a passivation agent, and a gel material.

A method for separating particles or droplets according to some embodiments of the current invention includes providing a passivated gel that has a well, loading the particles or droplets into the well of the passivated gel, and actuating the particles or droplets through the passivated gel by a device such that the particles or droplets propagate through the passivated gel.

BRIEF DESCRIPTION OF THE DRAWINGS

Further objectives and advantages will become apparent from a consideration of the description, drawings, and examples.

in 5 mM aqueous sodium borate buffer at pH=9.00. The gel is made of 0.195% (w/w) agarose and passivated by 3.25 mM PEG1000.

Figure 9:
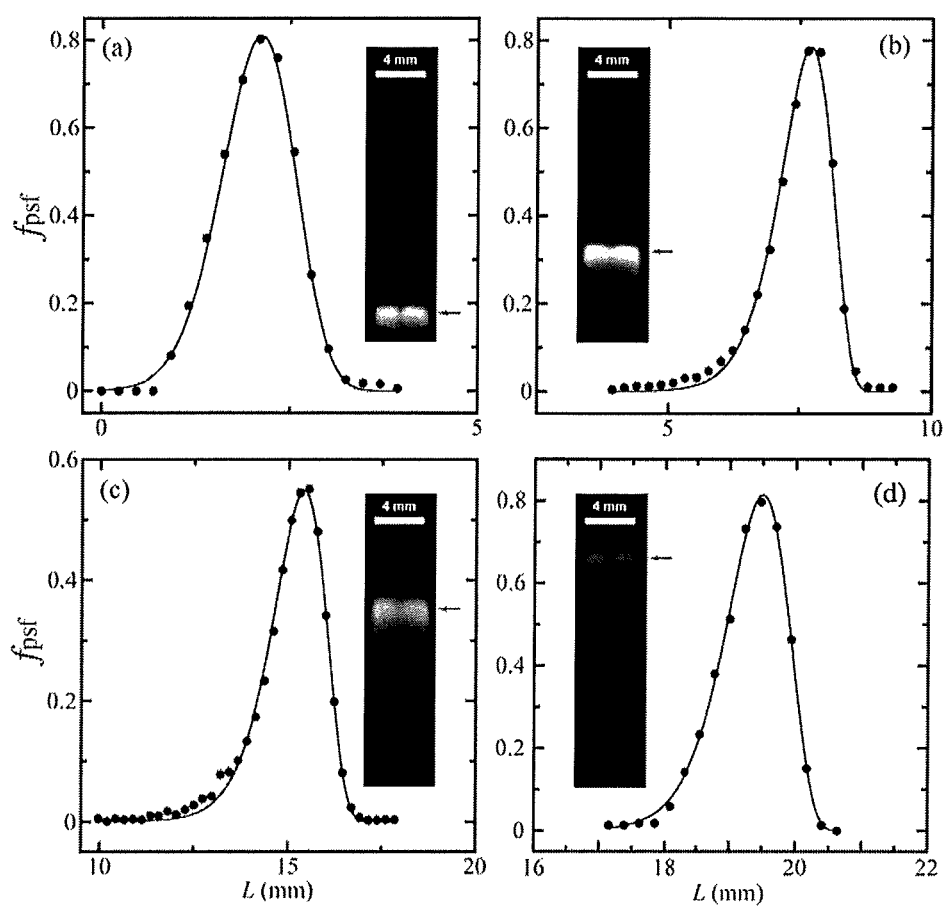

FIG. 9 shows measured normalized point-spread functions $f_{psf}$ for four different monodisperse sulfate-stabilized polystyrene nanospheres that have propagated through a PEG-passivated agaros gel after a time $t=1.5\times10^4$ s for average sphere radii <a> (nm)=(a) 105, (b) 70, (c) 42, (d) 18. Each measured $f_{psf}$ is fit to a reversed-log-normal function using Eq. (5) (lines); fit parameters are displayed in Table 1. Insets: images of corresponding lanes showing light scattered from individual bands (arrows) of monodisperse particles. The electric field is in the vertical direction; L=0 is the bottom of the inset. Conditions: 20° C., 5 mM sodium borate buffer (pH=9.0), [Agarose]=0.45% (w/w), [PEG1000]=7.5 mM, and $E=1.6\times10^{-4}$ statV/cm.

Figure 10:
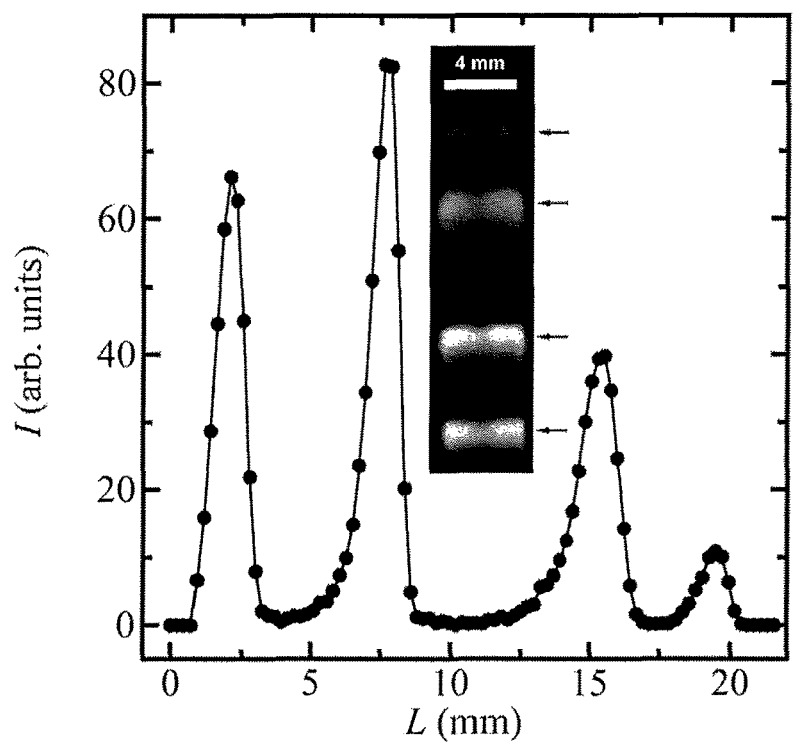

FIG. 10 shows measured scattered light intensity, I, averaged horizontally across a lane, versus distance of propagation distance, L, along a lane of a multi-modal mixture of sulfate-stabilized polystyrene nanospheres at a time $t=1.5\times10^4$ s after initiating gel-EP in a passivated agarose gel. Background light scattered from the gel has been subtracted to enhance contrast. A solid line guides the eye. Inset: corresponding measured image of an electrophoretically separated multi-modal mixture showing four individual bands (arrows), from which 4 peaks in I(L) can be readily identified. The electric field is in the vertical direction; L=0 is the bottom of the inset; L increases towards the top of the page. Conditions: 20° C., 5 mM sodium borate buffer (pH=9.0), [Agarose]=0.45% (w/w), [PEG1000]=7.5 mM, and $E=1.6\times10^{-4}$ statV/cm.

Figure 11:
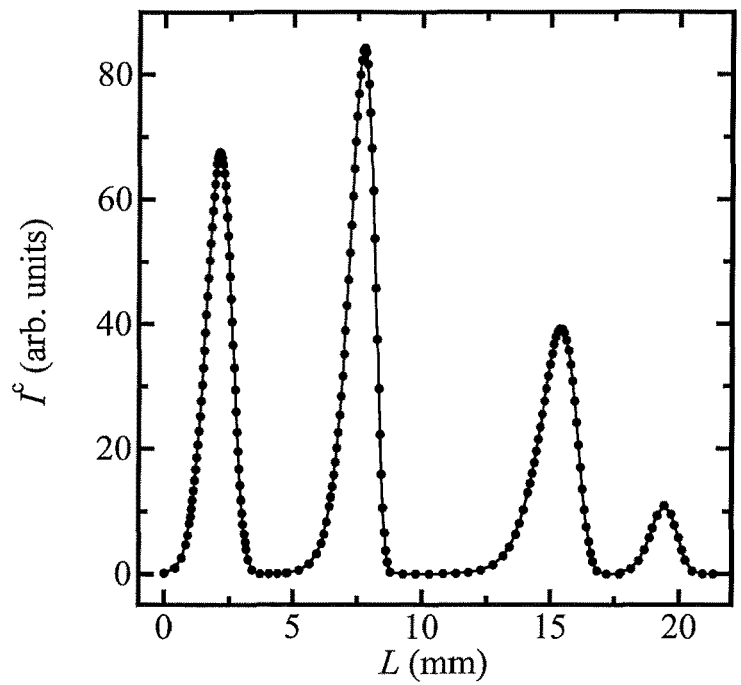

FIG. 11 shows forward-convolved scattered light intensity $I_c$ versus propagation distance L resulting from a 4-peak gaussian model of a multi-modal size distribution (see FIG. 12), convolved with the adaptive asymmetric point-spread function (AA-PSF) determined from FIG. 9. A solid line guides the eye. The resulting $I_c(L)$ closely matches the measured I(L) in FIG. 10, minimizing $\chi^2$ between these two functions.

Figure 12:
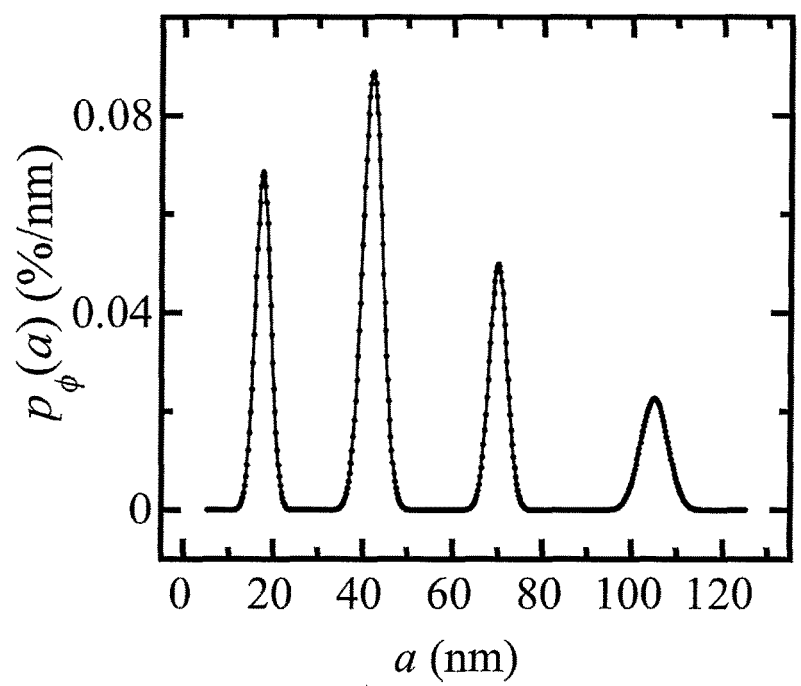

FIG. 12 shows deconvolved nanosphere radial size probability distribution $p_\phi(a)$, where $\phi$ is the nanoparticle volume fraction initially loaded into a well and a is the radius, obtained from I(L) of FIG. 10, using the adaptive asymmetric point-spread function (AA-PSF). The locations, widths, and heights of the four peaks shown in this $p_\phi(a)$ are in good agreement with the known radii, polydispersities, and absolute volume fractions of each dispersion added to make the mixture.

Figure 13:
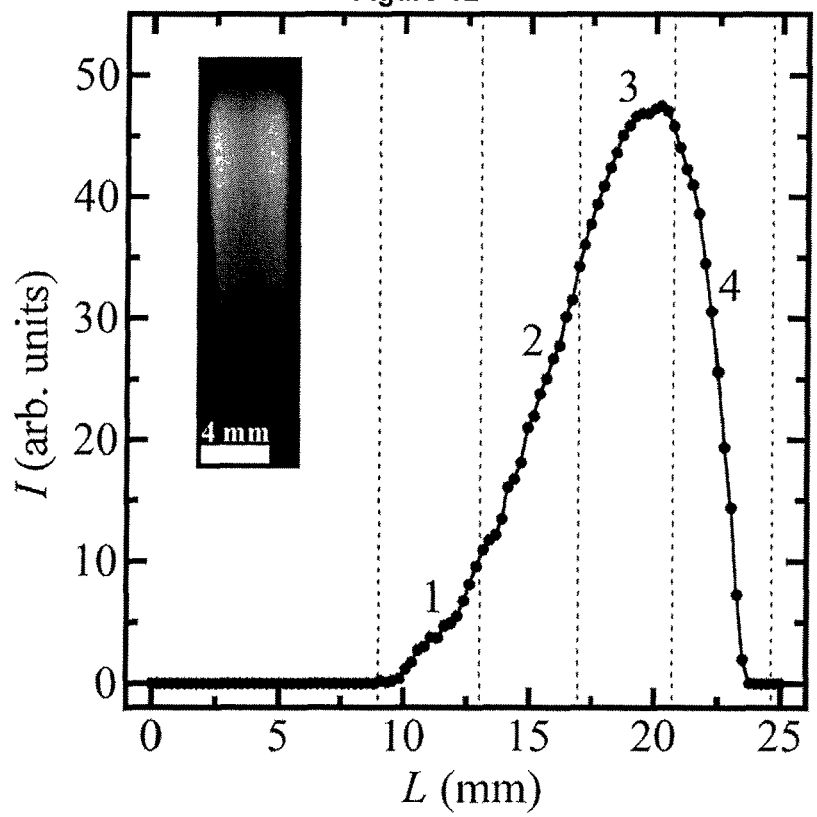

FIG. 13 shows measured intensity as a function of propagation distance, I(L), of an SDS-stabilized TPTMS silicone oil-in-water nanoemulsion using PEG-passivated agarose gel electrophoresis. Inset: background-subtracted image of the lane containing the nanoemulsion taken at a time of $t=1.8\times10^4$ s after applying the voltage. The wide, single peak in I(L) indicates that the distribution of droplet radii is broad and polydisperse, yet monomodal. Solid line: guides the eye. Vertical dashed lines: the gel is sliced after electrophoresis in order to recover the nanodroplets in regions 1-4 for further testing by dynamic light scattering (see Table 2). Conditions: 20° C., 5 mM SBB, pH=9.0, [Agarose]=0.45% (w/w), [PEG]=7.5 mM, and $E=1.6\times10^{-4}$ statV/cm.

Figure 14:
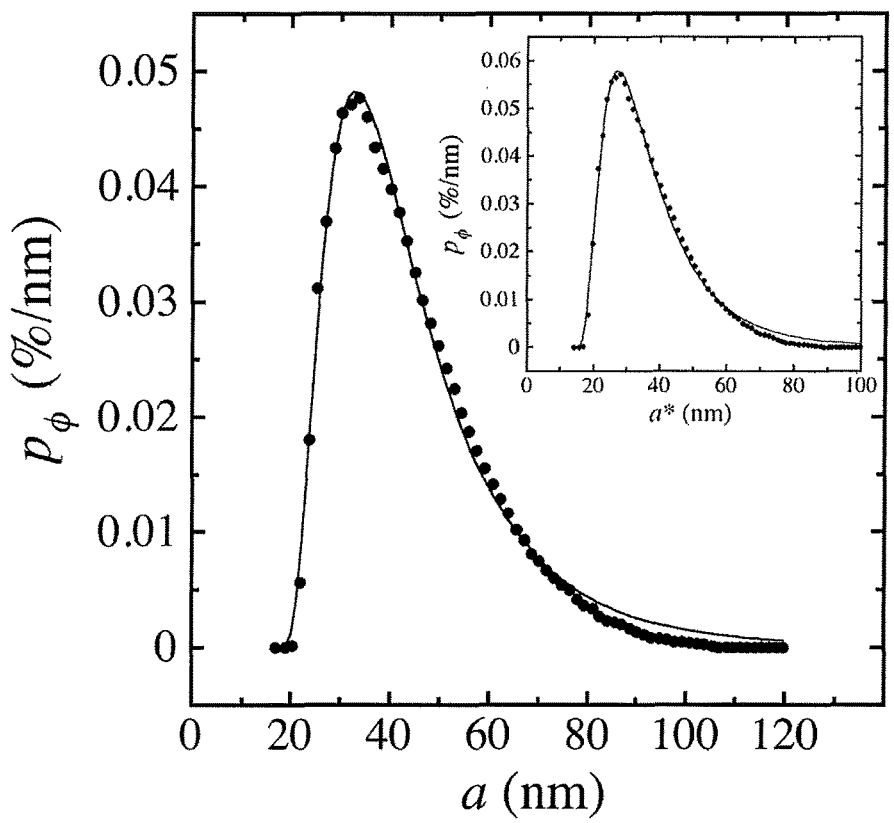

FIG. 14 shows deconvolved radial size distribution $p_\phi(a)$, of an SDS-stabilized silicone oil-in-water nanoemulsion, corresponding to I(L) shown in FIG. 13, resulting from the application of a deconvolution algorithm. Integration of $p_\phi(a)$ between an upper radius and a lower radius yields the volume fraction of droplets in that size range of the nanoemulsion loaded into the well. Inset: $p_\phi$ as a function of effective electrophoretic radius $a^*=a/(q_{NE}/q_{PS})$ corresponding to the relative electrophoretic mobility of nanoemulsion droplets compared to polystyrene nanospheres, accounting for the charge ratio $q_{NE}/q_{PS}$ of a nanoemulsion droplet to a polystyrene sphere having the same size. Solid lines: fits to log-normal distributions.

Figure 15:
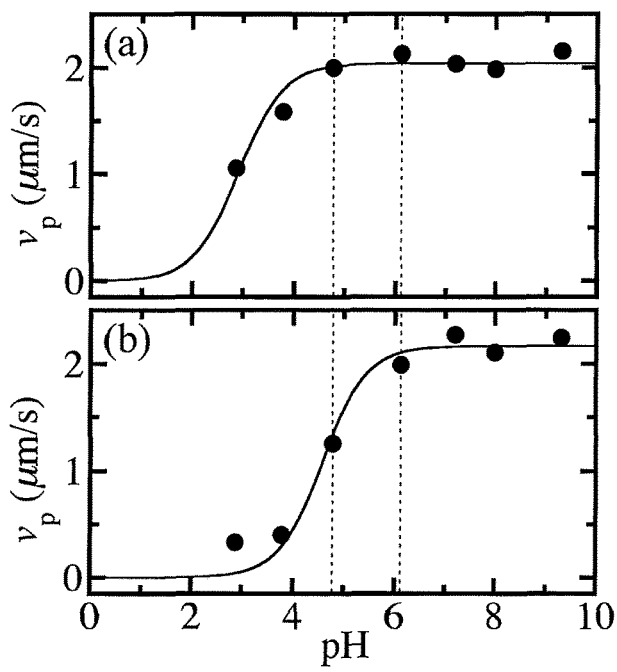

FIG. 15 shows pH dependence of the plateau velocity $v_p$ during electrophoresis for polystyrene nanospheres (PSNS) having similar radius a stabilized by different surface charge groups: (a) sulfate (a=42 nm) and (b) carboxyl (a=41 nm). Solid lines: fits based on protonation of surface charge groups, yielding good agreement with established $pK_a$'s of each group. Conditions: 20° C., $E=1.6\times10^{-4}$ statV/cm, 5 mM aqueous buffer solutions (see Table 2) at optimum buffering capacities. Gels (0.6% wt agarose and 10 mM PEG1000) are soaked in buffers for 2 days after casting before performing gel electrophoresis. The dashed vertical lines indicate the pH values used in measurements of FIG. 16: left corresponds to pH=4.76 and right corresponds pH=6.12.

Figure 16:
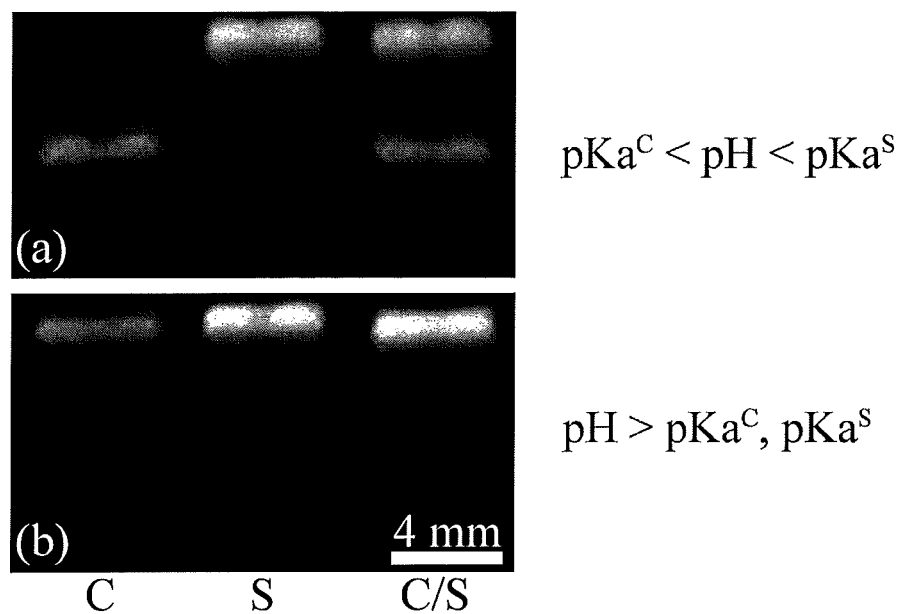

FIG. 16 shows gel electrophoresis images at $t=3.2\times10^4$ s showing separation of PSNS having the same radius and stabilized by carboxyl (C) and sulfate (S) surface charge groups at different pH: (a) pH=4.76, between the $pK_a$'s of C and S groups, where separation of a mixture of C and S is observed since C propagates more slowly; (b) pH=6.12, above the $pK_a$'s of both groups, so C and S propagate at the same velocity and no separation of C from S occurs. Bands are labeled C (a=41 nm), S (a=42 nm), and C/S for a 1:1 mixture of C and S. Lowest edges of the images in (a) and (b) represent the starting locations of bands before the electric field is applied. Conditions: 20° C., $E=1.6\times10^{-4}$ statV/cm, 5 mM aqueous buffer solutions at their optimum buffering capacity. Gels (0.6% wt agarose and 10 mM PEG1000) are soaked in buffers for 2 days after casting to ensure complete buffer exchange and a uniform pH everywhere in the gels.

Figure 17:
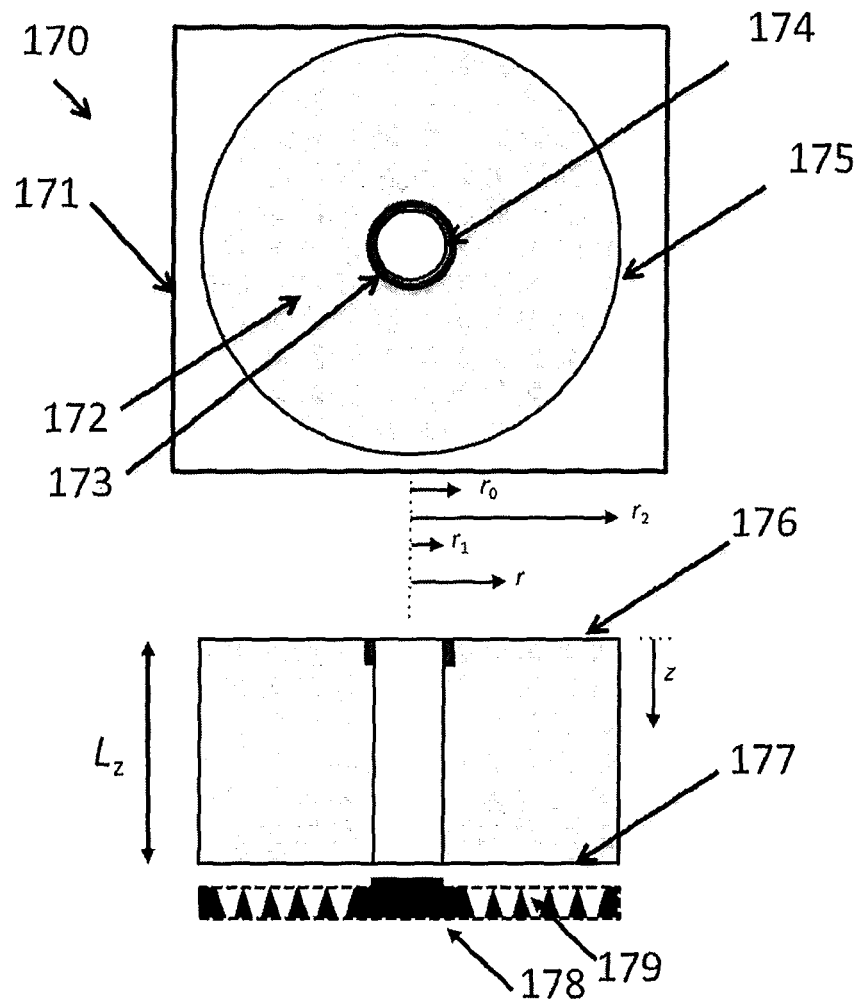

FIG. 17 is a schematic diagram of an embodiment of a colloidal separator with a top view (top panel) and a side cross-sectional view (bottom panel).

Figure 18:
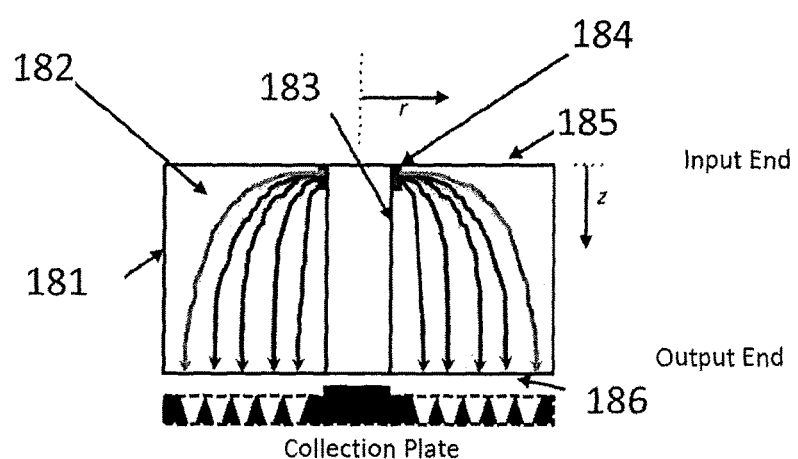

FIG. 18 is an example of propagation trajectories of small-scale objects in the passivated gel of a continuous colloidal separator. Distance of the small scale objects from the central radial electrode (183) is dependent upon the electrophoretic mobilities of the individual objects such that those with larger electrophoretic mobilities move further away from the central radial electrode in a given time. Small-scale objects have anionic charge as shown.

Figure 19:
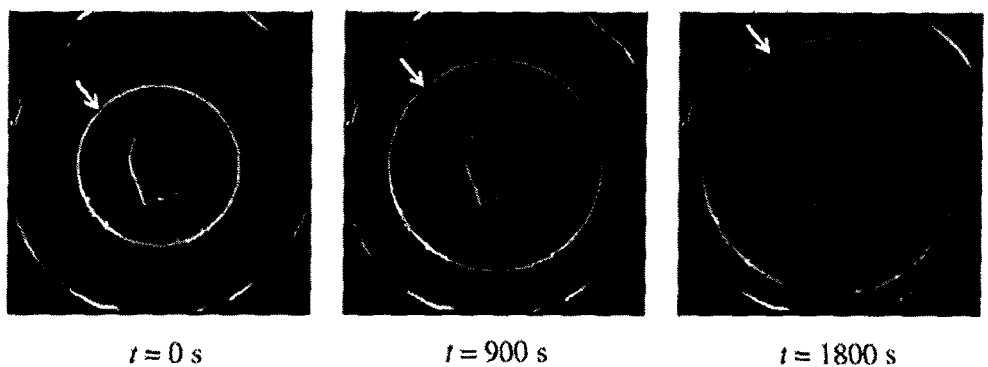

FIG. 19 shows images at successive times t after applying a voltage to create a radial electric field, showing an outward propagating ring (arrows) of carboxyl-stabilized polystyrene spheres (a=42 nm) in a large pore passivated agarose gel. Images have been background subtracted to enhance contrast. Other features in the images arise from scattering from the rest of the annular-cylindrical gel-EP apparatus.

Figure 3:
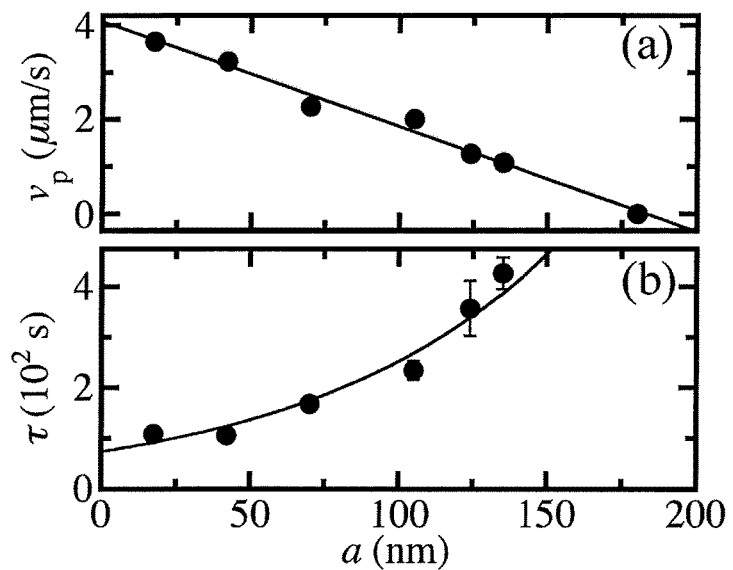
FIG. 3 shows the fitting parameters extracted from FIG. 2 as a function of sphere radius a: (a) plateau velocity $v_p$ and (b) rise time τ required for the particles to accelerate to $v_p$. The parameter corresponding to acceleration in the plateau region is very small $a_p \cong 10^{-5}$ μm/s² and is independent of radius a within experimental uncertainty.
Figure 20:
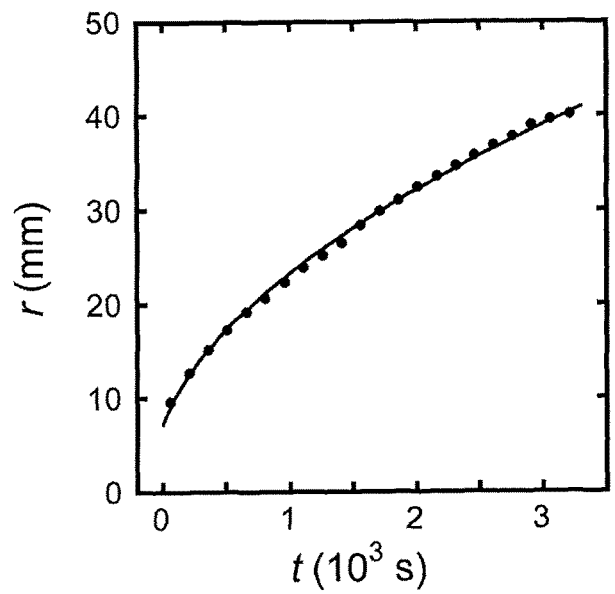

FIG. 20 shows measured time-dependent radius r(t) of an outward propagating ring of carboxyl-stabilized polystyrene spheres (a=42 nm) in a large pore passivated agarose gel, as obtained from background-subtracted images shown in FIG. 3. The solid line is a fit to the functional form $r_0(1+0)^{1/2}$.

Figure 21:
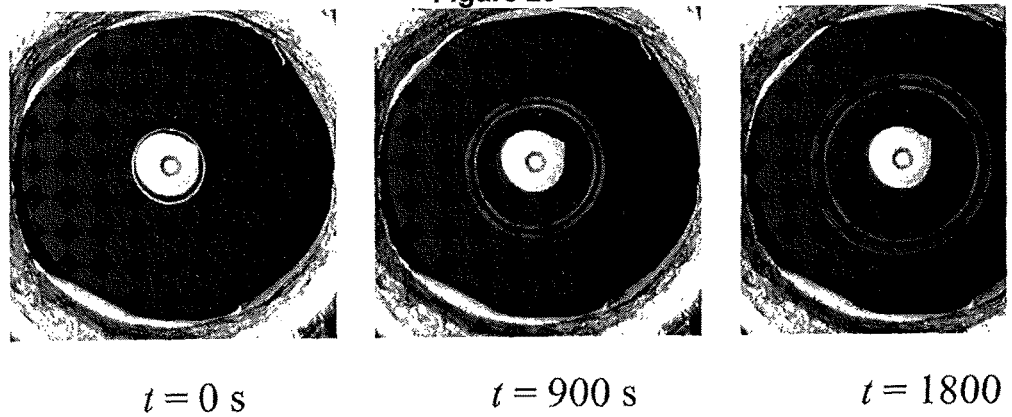

FIG. 21 shows images at successive times t after applying a voltage to create a radial electric field, showing separating outward propagating rings of polystyrene spheres (radii a=42 nm, 55.5 nm, and 70 nm) in a large pore passivated agarose gel. Other features in the images arise from scattering from the rest of the annular-cylindrical gel-EP apparatus.

Figure 5:
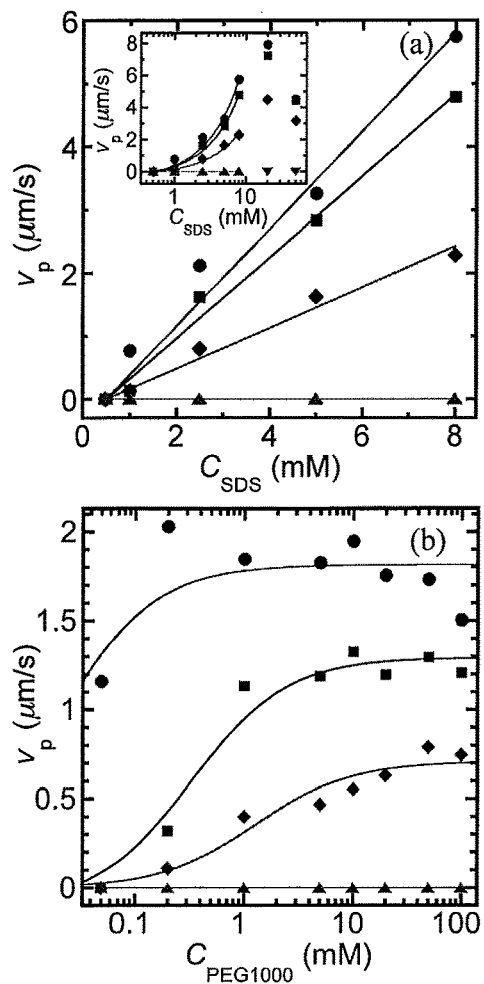
FIG. 5 shows dependence of nanosphere propagation velocity on surfactant type and concentration. The plateau propagation velocity $v_p$ of SSPSNS is plotted as a function of the concentration of passivation agent: (a) sodium dodecyl sulfate $C_{SDS}$ and (b) poly(ethylene glycol) having an average molecular weight of 1000 g/mol $C_{PEG1000}$, for particle radii a (nm)=17.5 (●) 42 (■), 70 (♦), 105 (▼), and 124 (▲). The inset in (a) is the same plot in a linear-log format showing the non-linear region at higher $C_{SDS}$. Conditions: 20° C., 5 mM SBB, pH=9.00, [Agarose]=0.600% (w/w), and E=1.6×10⁻⁴ statV/cm.
Figure 22:
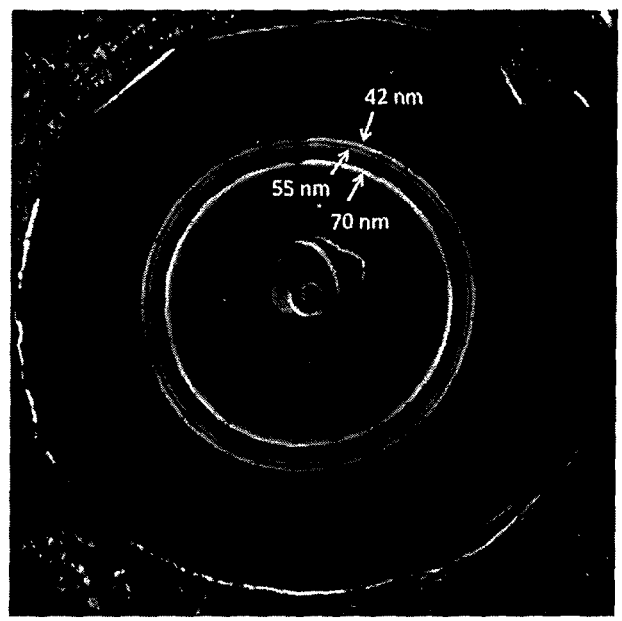

FIG. 22 shows background-subtracted image at t=1800 s (taken from the rightmost panel of FIG. 5) after applying a voltage to create a radial electric field, showing three distinct, separated rings of monodisperse polystyrene spheres (radii a=42 nm, 55.5 nm, and 70 nm: see arrows) in a large pore passivated agarose gel.

Figure 23:
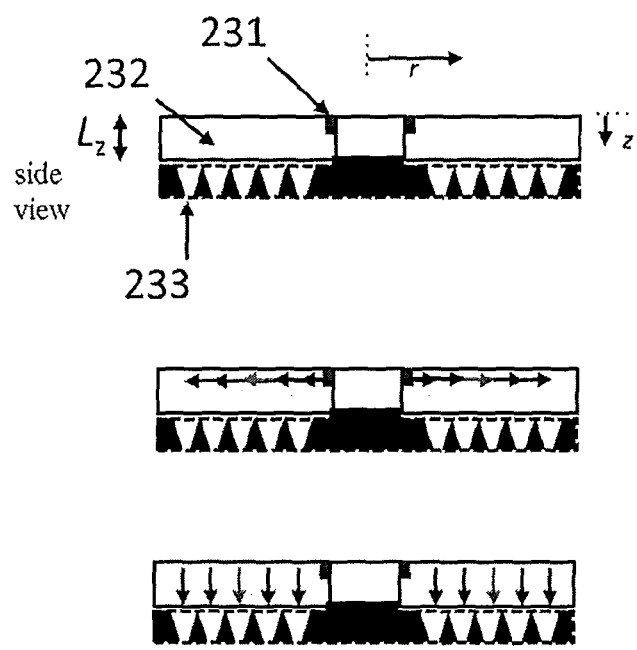

FIG. 23 shows a schematic of a continuous colloidal separator wherein separated nanoscale objects can be transported from collection wells by fluidic output lines connected to the collection wells.

Figure 24:
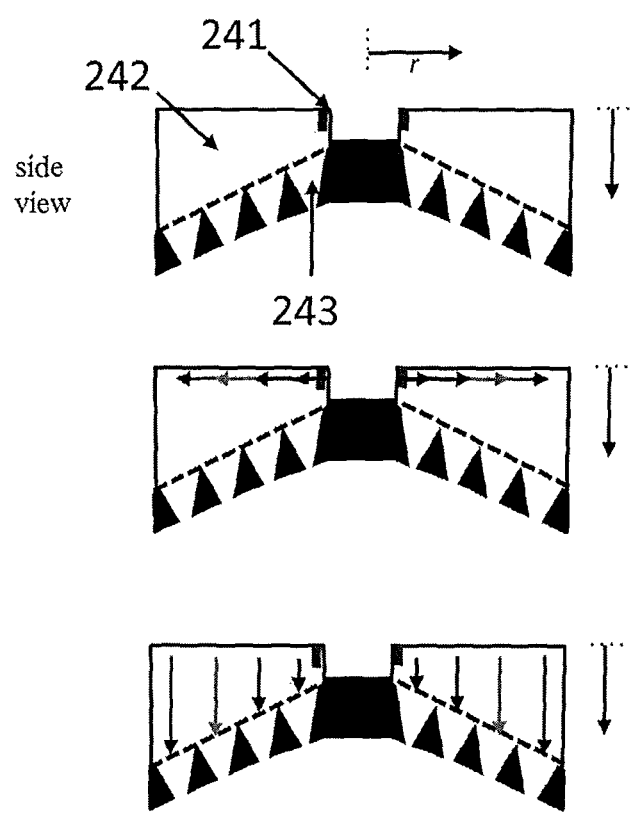

FIG. 24 shows a schematic of a continuous colloidal separator with an optimized annular slab geometry.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figure 1A:
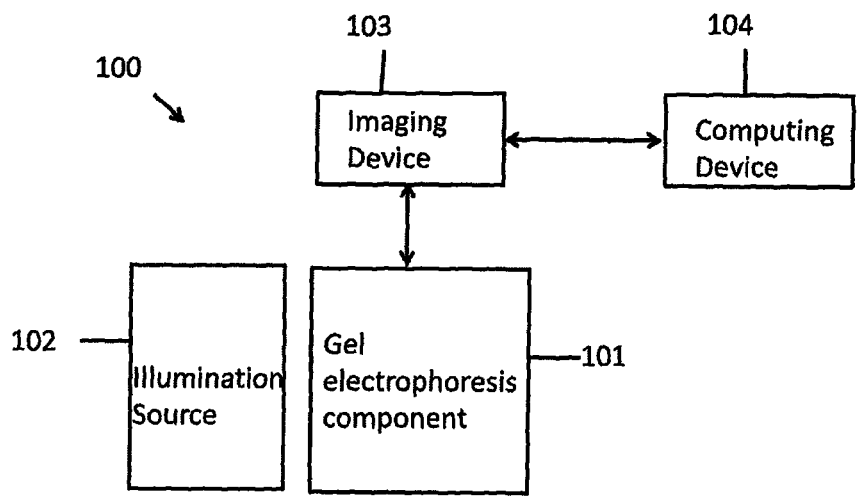
FIG. 1 shows schematics of embodiments of the invention. A) shows a schematic of a device for measuring size distributions of particles and droplets. B) is a Schematic of an optical video band-tracking electrophoresis apparatus for separating and measuring size distributions of nanoparticles using scattered light.

FIG. 1A shows a device for measuring size distributions of particles and droplets (100) according an embodiment of the invention. Device 100 may include a gel electrophoresis component (101) that may include a gel chamber that is suitable to receive a gel in which particles or droplets may propagate during operation. An illumination source (102) may also be arranged to illuminate propagating particles and a result the particles or droplets absorb, scatter or emit light. Device 100 may also include an imaging device (103) configured to obtain image data from the light absorbed, scattered, or emitted from the propagating particles or droplets. A computing device (104) may also be configured in device 100 to receive and process the image data so to provide information concerning a size distribution of the propagating particles or droplets.

Gel electrophoresis component 101 may include a gel suitable to mediate propagation of particle(s) or droplet(s) when the at least one of the particles or droplets have an ensemble average maximum spatial dimension greater than 1 nm, greater than 1 nm and less than about 10 µm, or greater than 20 nm and less than about 5 µm. The gel can also be passivated. Passivation can be done with a polymer (such as polyethylene glycol) or an amphilic surfactant (such as sodium dodecyl sulfate).

Illumination source 102 can be positioned along a side of gel electrophoresis component 101. In addition, illumination source 102 can emit white incoherent light. In some embodiments, the illumination source can provide a light that is scattered by the particles or droplets with an intensity as a function of the spatial positioning the particles or droplets within the gel.

Computing device 104 can be further configured to determine distribution of sizes of said at least one propagating particle or droplet. Computing device 104 can also be configured to model the distribution of sizes of the propagating particles or droplets. This model can include an adaptive asymmetric point-spread function to deconvolve mobility and size distributions. Computing device 104 can also be configured to measure a size distribution the particles or droplets from the spatial distribution of scattered light from the particles or droplets. Furthermore, computing device 104 can be configured to determine a point-spread function from image data of the particles or droplets. In some cases, this point spread function is determined by fitting a reversed log-normal function to the image data.

FIG. 17 shows a device for separating particles or droplets in a bulk solution (170). Device 170 may include a gel electrophoresis component with a chamber suitable to receive a gel (171). Gel electrophoresis component with a chamber 171 may include a gel (172) in which at least one of the particles or droplets propagates during operation. Gel electrophoresis component 171 may also include a first set of at least two electrodes (174 and 175) opposing one another so as to create an electric field following application of a voltage. Gel electrophoresis component 171 may also include a second set of at least two electrodes (176 and 177) positioned opposing one another and perpendicular to the first set of the at least two electrodes (174 and 175) so as to create a second electric field following application of a second voltage wherein the second electric field is perpendicular to the first electric field. Device 170 can also include a collection plate (178) positioned at a surface the gel with plurality of collection wells (179).

Gel electrophoresis component 171 may include a gel (172) suitable to mediate propagation of particle(s) or droplet(s) when at least one of the particles or droplets has an ensemble average maximum spatial dimension greater than 1 nm, greater than 1 nm and less than about 10 µm, or greater than 20 nm and less than about 5 µm. The gel can also be passivated. Passivation can be done with a polymer (such as polyethylene glycol) or an amphilic surfactant (such as sodium dodecyl sulfate).

In the above embodiments, particles or droplets may or may not have a uniform or symmetric geometric shape. In these instances, the maximum spatial dimension refers to the largest width of the particle or droplet. In other words, the particle or droplet would be able to fit entirely within a sphere having the maximum dimension, inclusive of touching the sphere.

EXAMPLES

Example 1: Passivated Gel Electrophoresis of Charged Nanospheres by Light-Scattering Video Tracking In this embodiment we disclose a a method of passivating gels to inhibit binding of nanoparticles to the gel network, and we use this method to study passivated agarose gel-EP of monomodal and multimodal mixtures of highly monodisperse, sulfate-stabilized, spherical, polystyrene nanoparticles using real-time, optical video-tracking analysis to detect bands of scattered visible light. To inhibit undesirable binding in gel-EP experiments, we treat the agarose gel using a molecular passivation agent, such as a polymer or amphiphilic surfactant, that has an affinity for the gel network, yet confers a short-range repulsive interaction between the network and the particles. Gel passivation overcomes the common problem of nanoparticles strongly adhering to the gel immediately when they enter it after an electric field is applied and they leave the loading well. Moreover, by side-illuminating an optically transparent gel-EP apparatus with visible light and taking advantage of the light scattered at ninety degrees from the nanospheres in the gel, as detected using a video camera, we track in real-time and record movies of bands of scattered light from the nanoparticles, reflecting their motion as they electrophoretically propagate in the gel. We extensively explore conditions that affect the electrophoretic propagation of sulfate-stabilized polystyrene (SSPS) nanospheres, and we measure their propagation distances and velocities as a function of particle radius a though large-pore agarose gels. Our measurements provide insight into the effective electrophoretic mobilities of compact, charged spherical particles in passivated gels over a wide range of conditions.

Materials and Methods

In this embodiment, we make agarose gels using common agarose (type I-A, low electroendosmosis (EEO), Sigma-Aldrich). Although more complex buffers also are suitable, we typically make a simple sodium borate buffer (SBB, pH=9.0 at 5 mM) using sodium borate decahydrate ($Na_2B_4O_7 \cdot 10H_2O$, Fisher Scientific). We use the following passivation agents: polyethylene glycol (PEG, Scientific Polymer Products), having a range of molecular weights $M_w$(g/mol)=300 (PEG300), 1,000 (PEG1000), and 10,000 (PEG10000), and sodium dodecyl sulfate (SDS, Sigma-Aldrich). All chemicals are used without further purification. A set of monodisperse, surfactant-free, sulfate-stabilized polystyrene (SSPS) nanospheres (Invitrogen) have radii and polydispersities, as measured using electron microscopy and reported by the manufacturer (in nm), of: 18±2.5, 42±2.5, 70±1.5, 105±5.5, 135±4.5, and lastly 180 nm, which has an estimated polydispersity of ±7 nm based on other similar products in that size range.

Figure 1B:
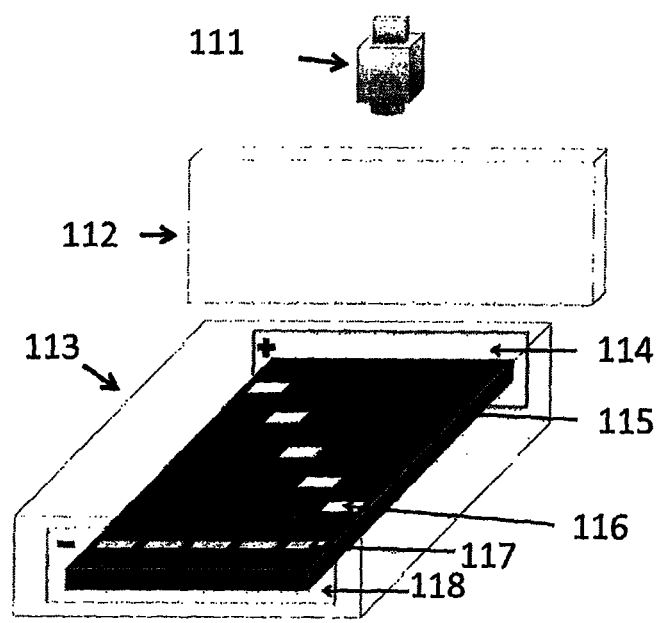

All experiments are carried out in a common gel-EP apparatus equipped with positive and negative platinum (Pt) wire electrodes (NeoSCI Electrophoresis #55-1094, 20 cm×10 cm×9 cm) using a simple DC power supply capable of generating voltages up to 125 V (Whatman/Biometra Electrophoresis DC Power Supply #125). This power supply is typically set at a lower 57 V (measured) for most experiments. This apparatus is ideal for illuminating and imaging the propagating nanoparticles in the gel because the plastic walls of the gel-EP chamber are optically transparent. In FIG. 1B, 111=a digital camera, 112=a light box, 113=an electrophoresis chamber, 114=a+electrode, 115=a polymer gel (slab) in a buffer solution containing a passivation agent, 116=bands of light scattered from charged particles propagating in gel into digital camera, 117=wells, and 118=a− electrode.

As shown in FIG. 1B, we illuminate the gel-EP apparatus from the side with white incoherent light using a large light box (GLOW BOX, Instrument for Research and Industry, Cheltenham Penna, Model No. GB11-17, 30 Watts, 53 cm×30 cm×10 cm). This light box provides very uniform side-lighting over a large spatial area. As shown in FIG. 1B we illuminate the gel-EP apparatus from the side with white incoherent light using a large light box (GLOW BOX, Instrument for Research and Industry, Cheltenham Penna, Model No. GB11-17, 30 Watts, 53 cm×30 cm×10 cm). This light box provides very uniform side-lighting over a large spatial area. In FIG. 1B, nanoparticles (e.g. nanospheres, nanodroplets, and nano-objects) are loaded into wells in a slab of gel, such as an agarose gel, that is immersed in an aqueous solution. The gel is supported by a transparent solid support (e.g. plastic baseplate) that is part of the electrophoresis chamber. The aqueous solution is typically a buffer solution at a fixed pH, and the aqueous solution typically contains a passivation agent that passivates the gel, enabling propagation of the loaded species. A voltage, produced by an electric power supply (not shown), is applied between two electrodes, designated as +electrode and −electrode, which are typically made of platinum wire and are mounted at opposite ends of the electrophoresis chamber beyond the ends of the gel slab. This applied voltage produces an electric field E that predominantly lies in the plane of the slab. Nanoparticles propagate through the gel along the direction of the electric field at different speeds that depend on their sizes, shapes, and charges. In the image shown, nanoparticles have anionic charge, so they propagate towards the +electrode. The positions of the nanoparticles which were loaded into one or more wells are detected using a camera and lens having an optical axis normal to the plane of the gel slab. The gel and particles are illuminated from the side by a light box that creates uniform diffuse light (which has a range of wavelengths suitable for detection by the camera); the camera detects light scattered from the nanoparticles. The scattered light appears as narrow bands, identifying the locations of the nanoparticles, if all of the nanoparticles loaded into a particular well are highly uniform in size, shape, and charge. The camera is connected to a digital computer equipped with a suitable digital camera interface. Not shown: a first piece of lint-free cloth is immersed in the buffer solution between the gel and the +electrode, and a second piece of lint-free cloth is immersed in the buffer solution between the gel and the −electrode. These pieces of cloth prevent gas bubbles generated near the electrodes from moving into the viewing region and obscuring the imaging by the digital camera.

We image the light scattered from the propagating particles at ≈90° angle using a Point Grey Flea2 camera (FL2-08S2C, 8 bit, 30 fps max, 1024×768, IEEE-1394) equipped with a suitable lens that provides a high-resolution view of the entire gel slab. Using a custom-written computer program in LabVIEW, we independently control the shutter speed and acquisition rate of this camera to optimize the images of the particles without any pixel saturation and thereby record high-resolution, time-lapse movies having good signal-to-background. Gas bubbles generated during electrophoresis near the Pt electrodes can interfere with imaging if they enter the imaging field of view, so we prevent this by mounting washed lint-free cloth (Fisher Scientific, No. 06-667-14) between the electrodes and the gel slab at both ends of the gel-EP apparatus. To reduce the width of the wells, where particles are loaded into the gel, we make a non-standard fine-width comb out of thin non-stick 50 µm-thick Teflon tape and use this when casting the gel; typical dimensions of a single well are about 5 mm wide×50 µm thick×2.5 mm high. We observe that, when the thickness of the well that originally holds the particles is narrower, propagating bands of monodisperse particles in the gel are also narrower, which is advantageous. We fix the electrophoresis chamber, the light box, and the camera rigidly on an optical table to prevent changes in their relative positions, and the entire apparatus is cloaked using a dense black cloth.

We image the light scattered from the propagating particles at about a 90° angle using a Point Grey Flea2 camera (FL2-08S2C, 8 bit, 30 fps max, 1024×768, IEEE-1394) equipped with a suitable lens that provides a high-resolution view of the entire gel slab. Using a custom-written computer program in LabVIEW, we independently control the shutter speed and acquisition rate of this camera to optimize the images of the particles without any pixel saturation and thereby record high-resolution, time-lapse movies having good signal-to-background. Gas bubbles generated during electrophoresis near the Pt electrodes can interfere with imaging if they enter the imaging field of view, so we prevent this by mounting washed lint-free cloth (Fisher Scientific, No. 06-667-14) between the electrodes and the gel slab at both ends of the gel-EP apparatus. To reduce the width of the wells, where particles are loaded into the gel, we make a non-standard fine-width comb out of thin non-stick 50 μm-thick Teflon tape and use this when casting the gel; typical dimensions of a single well are about 5 mm wide×50 μm thick×2.5 mm high. We observe that, when the thickness of the well that originally holds the particles is narrower, propagating bands of monodisperse particles in the gel are also narrower, which is advantageous. This is an important difference when measuring particle size distributions, because wells that have larger widths exhibit a higher degree of smearing of peaks in I(L), and this smearing is not indicative of the true polydispersity in the size of the particles. The smearing of I(L) caused by using a well that is not so fine cannot easily be distinguished from the smearing of I(L) caused by propagation of particles through the gel during electrophoresis, so it is usually advantageous to use a very fine width, such as 50 μm, such as that given by the custom comb, when making wells in the gel. We fix the electrophoresis chamber, the light box, and the camera rigidly on an optical table to prevent changes in their relative positions, and the entire apparatus is cloaked using a dense black cloth. To prepare a passivated agarose gel, we typically add 30 mL of 5 mM SBB to agarose powder and a selected passivation agent, such as PEG1000 or SDS, at a desired concentration in a flask. We heat the solution for several short intervals (15-30 s) using a microwave oven and swirl the flask to prevent the solution from boiling out of the flask. We repeat this heating and swirling process until all of the agarose dissolves completely and the solution becomes clear. We let the solution cool to about 50° C. in a hot water bath. We seal both ends of the gel-casting tray with tape. We pour the melted agarose solution into the sealed tray, used as a mould, to produce a slab of gel (10 cm length×7 cm width×0.4 cm height). We place a comb in a pre-designed set of slots on the side-walls of the tray near one end of the agarose slab, so that the comb is inserted normal to the plane of the agarose slab, typically near one end of the slab. We allow the gel to cool to room temperature (about 20° C.) until it solidifies. We pull out the comb and remove the tape. Then we place the gel and the tray into the electrophoresis chamber filled with running buffer solution. If SDS is used as passivation agent in the gel, the running buffer also contains the same [SDS]. We avoid trapping any bubbles between the tray and the bottom of the chamber, because such bubbles scatter light and interfere with imaging. The most commonly used agarose gels used in our experiment ([agarose]=0.195% w/w) are predicted to have average pore radii of around 300 nm [55]. This average pore radius roughly sets an upper limit on the largest diameters of compact charged spheres that can propagate through passivated gels during gel-EP. Manipulating gels that have less than about 0.1% wow agarose becomes difficult using the simple transfer process because the gel is not as rigid and can easily become highly deformed during the transfer process from the fabrication tray into the gel-EP apparatus. However, it is possible to create and use agarose gels having even lower concentrations and larger pore sizes if a rigid plastic framework baseplate having a large-pore framework and very high porosity is inserted into the gel tray prior to adding the hot agarose solution and then cooling to cause the gelation. This framework enables transfer of weaker gels into the gel-EP apparatus without significantly impeding the progress of particles as they propagate.

To load a prepared gel with nanoparticles, we pipette about 4 μL of a $D_2O$-diluted dispersion of SSPS nanoparticles at a particle volume fraction ϕ into the wells created by the comb. This increased density caused by the $D_2O$ inhibits particles from leaving the gel region before gel-EP is started. The refractive index of the polystyrene nanospheres is n≈1.59 at 590 nm. Thus, the refractive index difference is Δn≈0.26 with respect to an aqueous solution. For most dispersions having an average radius in the range 40 nm<a<200 nm, we dilute ϕ to be in the range from 0.2% to 0.4%. For smaller particles having a<40 nm, higher ϕ (e.g. 2%) is more optimal in order to generate enough scattering intensity from the particles (relative to the scattered intensity from the gel) to record an adequate scattering intensity from the camera.

To eliminate background light scattering from the gel and to enhance the signal-to-background ratio of the propagating bands of monodisperse spheres that are imaged during gel-EP, we subtract each frame during gel-EP by an initial background image taken of only the gel itself. The average background scattering intensity from a gel slab having an agarose concentration between about 0.1% w/w and about 0.6% w/w in a typical illumination and detection configuration is in the range between about 15 and 30 intensity units on an 8-bit scale from 0 to 255 intensity units. Thus, the background scattering from the gel, while small, is not negligible. Consequently, we have written an automated band-tracking software program in LabVIEW to extract the intensity profile along lines parallel to the direction of propagation of particles within the width of each band for the background subtracted images. We measure intensity I as a function of distance L from a well along the axis corresponding to the direction of the electric field for a variety of conditions and times of observation t. For a given band, peak detection routine is used to analyze the intensity profile I(L) to determine the peak location along each line of pixels. The program then averages all peak locations detected for lines of pixels within the width of each band to generate an average peak location of a single band. For each frame, the difference between the location of the band and the well is defined as the propagation distance L(t) of this band at certain time point t, which is calculated by multiplying the frame number N by the acquisition time interval $t_0$ between consecutive frames. In each frame, the area under each peak is locally integrated to generate the total scattering intensity I from all particles associated with the corresponding band.

Computer for image storage, image processing, and implementing deconvolution routine: Dell Precision 490 Workstation loaded with LabVIEW software and Image acquisition and analysis virtual instruments.

Example of parameters used during a typical measurement of a size distribution: The measured output voltage of the Whatman/Biometra Electrophoresis DC Power Supply is 57.5 V. The buffer solution is 5 mM sodium borate buffer (SBB). The passivation agent is 10 mM PEG1000. A typical volume fraction of particles loaded into a well is about 0.5%. The time between consecutive frames of the recorded time-lapse movie is typically $t_0$=15 seconds. In our customized software package, we increase $t_0$ if the bands move slowly (i.e. if we use high agarose concentration or lower applied field strength) and we decrease $t_0$ if the bands move fast. We run the gel electrophoresis experiment and record images of the particles propagating in the gel until the particles of different sizes are completely separated. The duration of each electrophoresis experiment is determined by the agarose concentration [Agarose], the applied field strength E, and many other factors including the particle sizes. For example, when running polystyrene spheres having a between 18 nm and 135 nm using 0.195% agarose at E=1.6×10−4 statV/cm, with PEG1000 stabilizer in SBB, we waited roughly until at least after 5×10³ s in order to achieve adequate separation. If the observation time is too short, not enough separation of different particle sizes has occurred, and the extracted size distribution does not accurately reflect the true size distribution. However, if the observation time is too long, the scattered light intensity from any bands containing smaller particles can become too small to be captured by the camera, or smaller particles can even migrate beyond the observation region or total length of the gel. Thus, an optimum observation time is between these two limits, and we find that for the above conditions, the observation time of t≈1×10⁴ s is near optimal.

Steady-state deconvolved size distribution remains essentially constant over a range of times: Size distributions obtained by deconvolution at different observation times are effectively independent of observation time, provided the observation time is near optimal. If the observation time is chosen to be very small (i.e. very soon after the electric field has been turned on), then the resulting size distribution will not be as accurate and may contain features that do not truly reflect the size distribution accurately. A near-optimal time of observation is an observation time around which the extracted deconvolved size distribution of particles remains substantially the same.

Results and Discussion

We passivate the agarose gel using a molecular passivation agent, which can be either uncharged or charged, so that anionic nanoparticles do not bind to the agarose gel, since we observe that such nanoparticles do not propagate as a result of attractive interactions with even a larger-pore agarose gel if no passivation agent is used. Gel passivation enables untreated particles to propagate electrophoretically in a reproducible manner when the characteristic pore size of the agarose gel is physically large enough to allow particle propagation. For the vast majority of our studies, we use an uncharged PEG passivation agent that enables particle propagation in a standard low-EEO large-pore agarose gel, yet has no capacity to affect the overall charge on particle's surfaces through possible mechanisms such as adsorption.

Figure 2:
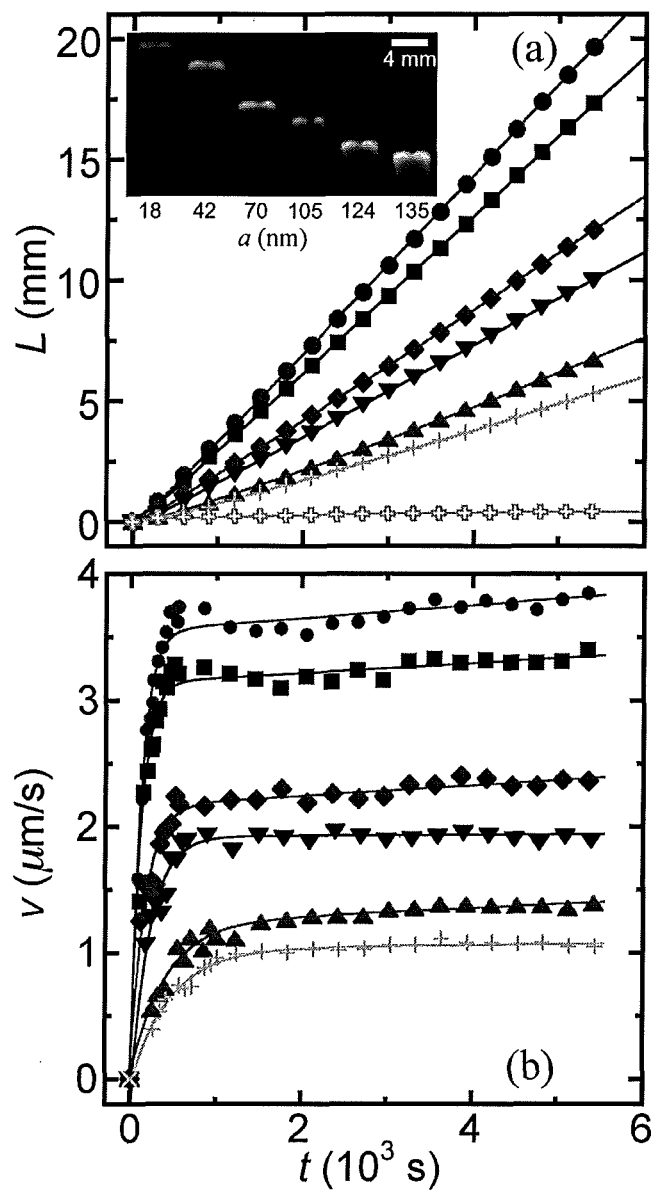
FIG. 2 shows video band-tracking analysis of SSPS nanospheres undergoing electrophoresis in 0.195% (w/w) agarose gel for different sphere radii a (nm)=17.5 (●), 42 (■), 70 (♦), 105 (▼), 124 (▲), 135 (+), and 180 (✦) (a) propagation distance L of a band and (b) the instantaneous band propagation velocity v=dL/dt are plotted as functions of time t after initiating electrophoresis. Lines are fits to the data using equations in the text. The inset in (a) is an example of a gel image at t=4.8×10³ s, after scattering from the gel (measured in an image from the digital camera taken before the voltage is applied) has been removed through background subtraction to enhance contrast. The lower edge of the inset represents the initial location of the bands before the electric field is applied (i.e. L=0 and t=0). Conditions: temperature is 20° C., 5 mM SBB, pH=9.00, [Agarose]= 0.195% (w/w), [PEG1000]=3.25 mM, and E=1.6×10⁻⁴ statV/cm.

The propagation distances L, measured from the boundary of the wells with the gel, of different discrete bands of SSPS nanospheres having radii a as a function of time t after turning on the electric field in a PEG-passivated agarose gel are shown in FIG. 2(a) (see caption for conditions). An image of the scattering from bands of nanospheres in the gel at t=4.8×10³ s is shown in FIG. 2(a)-inset. Smaller nanospheres propagate more rapidly than larger nanospheres; for a≥180 nm, we do not observe propagation and the nanospheres appear to be elastically trapped by the gel. From L(t), we calculate the instantaneous velocity of each band v(t) by taking a smoothed derivative, shown in FIG. 2(b). A rapid initial rise in v(t) is followed by a plateau in the velocity. In the plateau region, there is also a slight upward drift in the velocity, corresponding to a small acceleration. The measured v(t) of each isolated band can be fit to a simple model of propagation of charged nanospheres in a passivated gel, which has a size-dependent dissipative viscous resistance that increases for larger particle radii. Neglecting random thermal forces and particle inertia, we solve an equation of motion for a single sphere in a simple viscous liquid subjected to a constant electrophoretic force, and also empirically account for a small long-term drift in the velocity. The solution of this differential equation is an initial exponential rise, having a time scale τ, to a plateau velocity $v_p$ and an additional drift term involving a long-term acceleration $a_p$:

$$v(t)=v_p[1-\exp(-t/\tau)]+a_p t. \quad (1)$$

Fits to the measurements using Eq. (1) are shown by lines in FIG. 2(b). Integration of the v(t) curves yields high-quality fits to L(t) that have the same parameters, as shown by lines in FIG. 2(a). From these fits, we extract $v_p$(a) and τ(a), as shown in FIGS. 3(a) and 3(b), respectively. A linear fit to $v_p$(a)=(d$v_p$/da)(a*−a) exhibits good agreement, yielding a slope d$v_p$/da=22.3 1/s and a critical radius a*=180 nm, beyond which the SSPS nanospheres do not readily propagate in the gel. In FIG. 3(b), we empirically fit the values of τ(a)=τ*/(1−a/a*), where a*=180 nm is consistent with the velocity fit and τ*≈90 s, causing a divergence in the entrance time when the particles become larger than the largest pore sizes in the gel network and cease to propagate. Values of the acceleration $a_p$ from the fits are quite small (of order $10^{-5}$ μm/s²) and do not show any systematic trend. The observed minor acceleration effects could arise from slight evolution in the buffer and gel over long periods of time after the voltage is applied.

Figure 4:
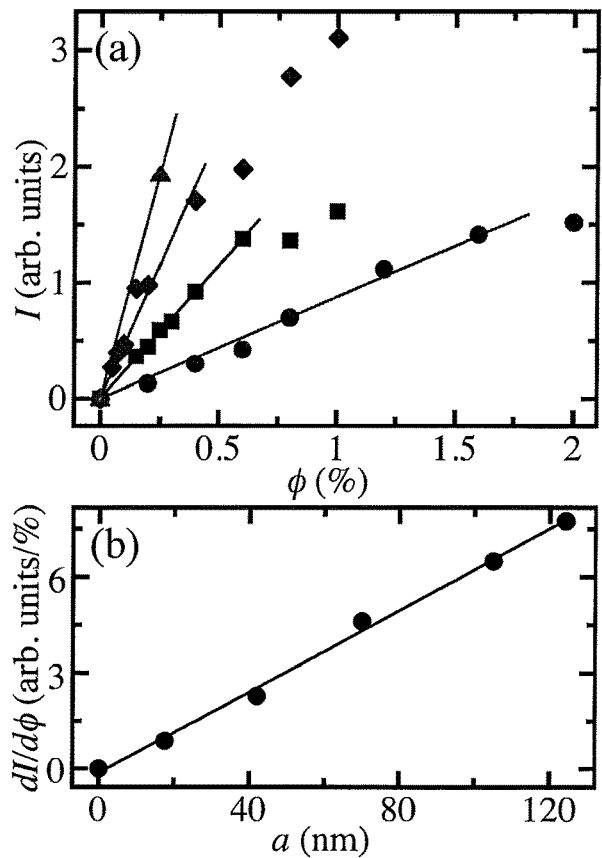
FIG. 4 shows Dependence of measured intensity I of SSPS nanospheres in agarose gel on sphere radius a and volume fraction φ. (a) Averaged and integrated intensity of scattered light from a band is plotted as a function of φ for SSPSNS having different a (nm)=17.5 (●) 42 (■), 70 (♦), 105 (▼), and 124 (▲). Lines are linear fits to the data. I(φ) becomes non-linear at larger φ; at least in part arising from multiple scattering. (b) The slopes dI/dφ at small φ in (a) depend linearly on a (the slope in (b) is 0.062 arb. units/%). Conditions: 20° C., 5 mM SBB, pH=9.00, [Agarose]= 0.195% (w/w), [PEG1000]=3.25 mM, and E=1.6×10⁻⁴ statV/cm. Although I and dI are reported in arbitrary units, to calibrate the intensity to the volume fraction of particles of a particular size originally loaded into the well, it is necessary to keep all illumination and detection geometries and parameters fixed to be the same as this calibration during experiments using passivated gel electrophoresis to determine a size distribution of particles in an unknown dispersion for which the size distribution is not known in advance.

In FIG. 4, we report measurements of the integrated intensity I of bands of SSPS nanospheres in the background-subtracted images as a function of the particle volume fraction ϕ and radius a. In FIG. 4(a), we show a series of data for I(ϕ) at different a. At a given a, for small ϕ, there is a linear region in which I is proportional to ϕ, and the response becomes non-linear for larger ϕ. The relationship between I and ϕ deviates from linearity because multiple scattering emerges at high volume fractions. In FIG. 4(b), we plot the dependence of the slope of the linear region, dI/dϕ, at low ϕ as a function of a. This slope dI/dϕ exhibits a linear dependence on a.

The intensities in FIG. 4 can also be used to determine the optimum ϕ at loading for the various particle radii to obtain the best optical signal-to-noise ratio. For each a, the optimum ϕ for tracking purposes is a balance between detecting adequate scattered light intensity from the particles and yet remaining in the linear response region, so that the intensity can be used to obtain ϕ in the gel. If the particle radii are very small (e.g. a<10 nm), then the light scattering intensity cannot be readily differentiated from the light scattered by the gel, making detection of the propagating bands by optical scattering very difficult, even after background subtraction.

We have studied in detail the performance of two different types of molecular passivation agents, neutral poly-(ethylene glycol) (PEG1000, $M_w$=1,000 g/mol), and SDS, an anionic surfactant, in agarose gels. Because PEG1000 is neutral, it cannot affect the charge on particles, and the particle's electrophoretic mobility and velocity. By contrast, SDS could influence the charge on the nanoparticles through adsorption, thereby complicating the interpretation of the gel-EP experiments, so we mainly study short-chain PEG-passivated agarose gels.

We show $v_p(C_{SDS})$ and $v_p(C_{PEG})$, where $C_{SDS}$=[SDS] and $C_{PEG}$=[PEG1000], for different SSPS nanosphere radii a in FIGS. 5(a) and 5(b), respectively. Interestingly, for SDS, a linear response in $v_p(C_{SDS})$ is observed below the critical micelle concentration (CMC) at around 8 mM; the response becomes non-linear and the velocity decreases for larger $C_{SDS}$. By contrast, for PEG1000, the response is not uniformly linear for all a, and the smallest nanospheres propagate readily when only very small quantities of PEG1000 above a threshold are present. Strikingly, for 1 mM≤$C_{PEG}$≤10 mM, the plateau velocity is nearly independent of PEG1000 concentration, and, thus, this appears to be an ideal range in which to perform physical gel-EP experiments involving nanoparticles. Even at very high $C_{PEG}$ approaching 100 mM, the plateau velocity does not decrease as significantly as it does for SDS. In either case, in the absence of any passivation agent, i.e. when $C_{SDS}$=0 mM and $C_{PEG}$=0 mM, none of the nanospheres propagate, regardless of a; the bands appear to be fixed at the point where the nanospheres just begin to enter the gel. Thus, we find that adequate concentrations of passivation agents are necessary when performing nanoparticle gel-EP experiments in standard agarose gels. The complexity of the electrophoretic response when using SDS, embodied in $v_p(C_{SDS})$, as compared to the ideal range for short-chain PEG, embodied in the nearly concentration independent range of $v_p(C_{PEG})$, indicates that using PEG as a gel passivation agent considerably simplifies interpretations of the measurements.

To survey which passivation agents are effective in passivating an agarose gel for anionic SSPS nanoparticles, we have repeated the same experiments, replacing PEG1000 and SDS with the same concentrations of sodium borate, sodium sulfate ($Na_2SO_4$), PEG300, PEG10000, or pure water when forming the gel. All other conditions (e.g. [agarose], T, E) being the same, except for PEG10000, the particles do not propagate through the gel for any of these other potential agents. We speculate that PEG300 does not passivate the gel because it has a shorter chain length and thus a lessened enthalpic attraction to the gel network, which relative to entropy, is insufficient to passivate the gel. As the molecular weight of PEG increases, its hydroscopic power and solubility in water deceases. For instance, PEGs having $M_w$≤800 g/mol are completely miscible with water at standard conditions, whereas the water solubility of PEG1000 is about 80% by weight. Consequently, although PEG10000 does function adequately as a passivation agent, we typically use PEG1000 because of its lower molecular weight and higher aqueous solubility. We speculate that the molecular weight of PEG1000 is large enough to ensure good binding to the gel relative to entropy but small enough so that its solubility in water is still very high so it can become very uniformly distributed throughout the gel network.

Figure 6:
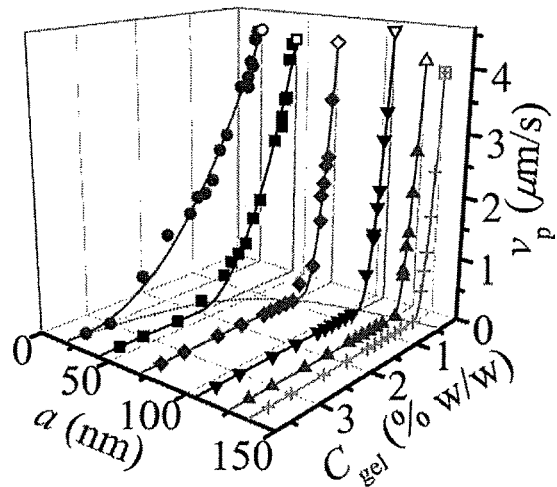
FIG. 6 shows Steady-state plateau propagation velocity $v_p$ is plotted as a function of $C_{gel}$ (% w/w) for SSPSNS having different radii a (nm)=17.5 (●) 42 (■), 70 (♦), 105 (▼), and 124 (▲), and 135 (+). Open symbols represent the extrapolated velocity at $C_{gel}=0$. The dotted curve in the a–$C_{gel}$ plane is a fit to the critical $C_{gel}$ (at which the velocity is zero) as a function of a. Conditions: 20° C., 5 mM SBB, pH=9.00, and E=1.6×10⁻⁴ statV/cm. The concentration ratio PEG1000:agarose is fixed as 10 mM PEG1000:0.6% (w/w) agarose.

In FIG. 6, we show how the gel concentration influences the measured plateau velocities of bands of nanospheres having different radii: $v_p(C_{gel},a)$. The concentration of the gel affects the effective pore size distribution of the gel network, and as $C_{gel}$ increases, the average of the pore size distribution shifts towards smaller pore sizes. When the nanoparticles cease to propagate, i.e. $v_p$=0 when $C_{gel}>C_{gel}^*$, a characteristic pore size of the gel associated with electrophoretic transport becomes too small for the nanoparticles to pass through, even after the gel has been passivated. In the a–$C_{gel}$ plane, we empirically fit these data to an inverse relationship $C_{gel}^*$~$a^{-1}$ (dotted line) that captures the observed trend. The measured values of particle diameters at which propagation ceases in PEG-passivated gels are near but somewhat smaller than other reported average pore sizes for the same agarose gel concentrations [55, 59, 56, 60]. The observed scaling $C_{gel}^*$~$a^{-1}$ implies that the passivated gel behaves as a random network of barriers and interconnected passageways which offers a heterogeneous environment that neither completely traps the compact spherical nanoparticles nor permits them to move unimpeded up to radii corresponding to a*. In addition, for each fixed a, we fit $v_p(C_{gel})$ to a quadratic form $v_p(C_{gel})=v_0(1-C_{gel}/C_{gel}^*)^2$ for $C_{gel}≤C_{gel}^*$, as shown by the solid lines in FIG. 6. All quadratic fits are constrained to be zero when intercepting the a–$C_{gel}$ plane;

the fit values agree well with the measured zero-velocity $C_{gel}^*(a)$. Extrapolation of these quadratic fits as $C_{gel}$ vanishes yields estimated values for the propagation velocities in the absence of gel, $v_0$, which are observed to be almost independent of a.

Figure 7:
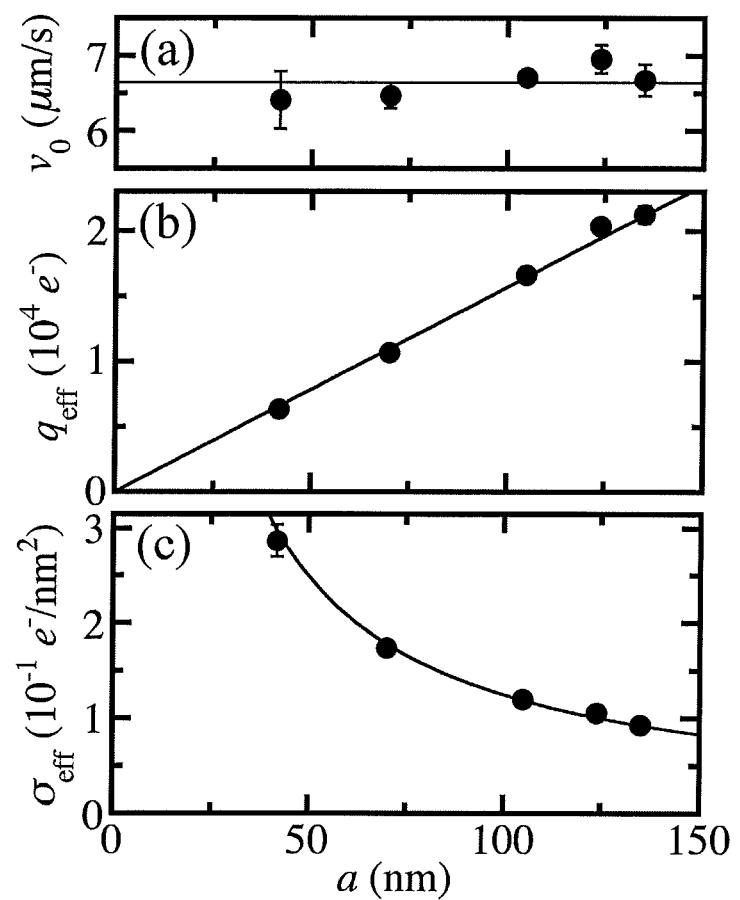
FIG. 7 shows nanosphere electrophoresis in the absence of agarose gel. Video tracking analysis of sulfate-stabilized polystyrene nano-spheres (SSPSNS) yields the following as a function of sphere radius a: (a) Stead-state particle propagation velocity $v_0$ (at zero gel concentration), (b) effective particle charge $q_{eff}$ determined using $v_0$, and (c) effective particle surface charge density $\sigma_{eff}$ calculated from $q_{eff}$. Conditions: 20° C., 0.5 mM SBB, pH=9.00, and E=1.6×10⁻⁴ statV/cm.

To characterize the surface charges on the nanospheres and their bare electrophoretic mobilties, we have measured the plateau velocity of nanospheres in the absence of any gel, yet in the same aqueous buffer environment and driving field as when the gel is present. Measurements of $v_p$ of regions of uniform nanospheres, deposited in the buffer using a micropipette, after turning on the electric field E, yield the measured zero-gel-concentration propagation velocities $v_0$, shown in FIG. 7(a). These velocities are larger than when the gel is present, and the measured values of $v_0(a)$ are nearly independent of radius. Since a is known, the viscosity of water, $\eta_0$≈$10^{-2}$ Poise, and the electric field strength E, we estimate the effective charge per particle:

$$q_{eff}(a)=6\pi\eta_0 a v_0(a)/E \tag{2}$$

which rises linearly, as shown in FIG. 7(b). We calculate E=D/$\varepsilon_\square$≈V/($\varepsilon_\square$d), where V and d are the voltage difference and distance between the two electrodes, respectively, and $\varepsilon_\square$=80.1 is the relative dielectric permittivity of water. We also report the effective surface charge density:

$$\sigma_{eff}(a)=q_{eff}(a)/(4\pi a^2), \tag{3}$$

as displayed in FIG. 7(c). These values of $q_{eff}$ and $\sigma_{eff}$ are within an order of magnitude of, but not the same as, values are reported by the manufacturer using a charge-titration method in a different aqueous environment, so there is reasonable agreement.

Figure 8:
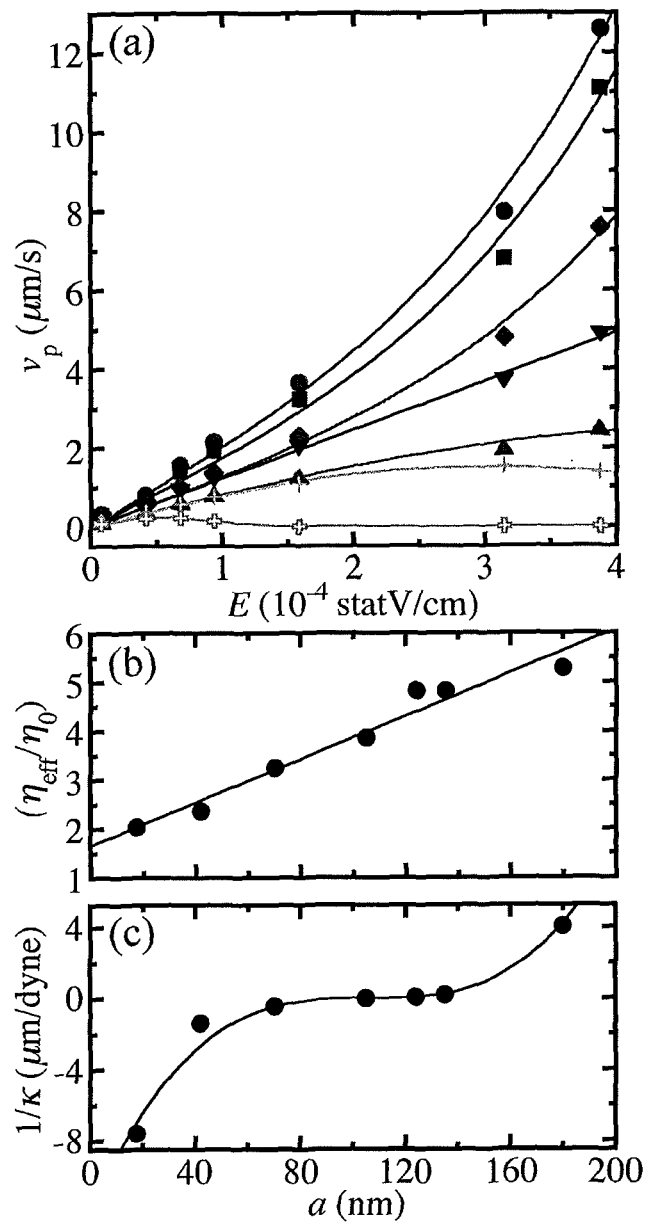
FIG. 8 shows The relationship between the applied field strength E and the plateau velocity $v_p$ is shown in part (a) for agarose gel electrophoresis of SSPSNS having different radii a (nm)=17.5 (●) 42 (■), 70 (♦), 105 (▼), and 124 (▲), 135 (+), and 180 (✦) Lines are fits to data (see text). The fitting parameters are plotted as functions of a in part (b) (the reduced effective viscosity $\eta_{eff}/\eta_0$) and (c) (1/κ). These gel electrophoresis experiments have been carried out at 20° C.

In FIG. 8(a), we report the propagation velocity $v_p$ as a function of the electric field strength E (in electrostatic cgs units) for SSPS nanospheres having different radii a. Reported values of E may somewhat overestimate the true field strength acting on the nanoparticles, since these values neglect complex effects related to ionic content in the buffer and also aspects of geometry that are non-ideal, such as the gel slab being raised somewhat above the plane containing the two Pt wires. Interestingly, using very high field strengths can actually inhibit propagation of particles that have larger radii. By contrast, the smallest particles propagate increasingly more rapidly as E is raised, leading to a response of $v_p(E)$ that is super-linear.

We fit all measurements of $v_p(E)$ using a single equation, which is motivated by a model of thermally-driven local hopping of charged particles driven by the electric field out of smaller pores that block passage of the particles (i.e. blind holes) into larger pores that permit passage through the gel (i.e. open holes) for a certain distance until the next obstruction is encountered:

$$v_p = \frac{qE}{6\pi\eta_{eff}a}\exp\left[-\kappa^{-1}(qE)^2/(k_BT)\right], \tag{4}$$

where q is the charge on a sphere, $k_B$ is Boltzmann's constant, $\eta_{eff}$ is an effective viscosity, and $\kappa^{-1}$ is a nanoscopic effective mechanical compliance reflecting average properties of gel-particle interactions, which include the local elastic response of the gel to the driven particle.

The size-dependence of the fitting parameters $\eta_{eff}(a)/\eta_0$ and $\kappa^{-1}(a)$ are shown in FIGS. 8(b) and 8(c), respectively. The mobility of nanoparticles in the gel matrix is primarily dictated by the particle size with respect to the gel mesh size.

Thus effective viscosity increases linearly with radius; larger particles experience increasing dissipative resistance. By contrast, the effective compliance changes from positive and large for the largest radii (i.e. strongly inhibiting propagation of the particles which are driven so forcefully that they can't be thermally activated out of blind holes), decreases through zero, and it actually becomes negative for smaller radii (i.e. suggesting that the gel network actually offers less resistance, possibly through changes in its morphology induced by the particle being driven through the gel or by the field on the gel itself, thereby allowing very small particles to propagate more easily at higher field strengths). Because the response of the velocity to applied field strength at values of $E>2\times10^{-4}$ statV/cm is nonlinear, we have chosen to set the applied voltage and therefore E for most of our experiments to be near the upper end of the linear response regime. Since a negative value of a compliance effectively corresponds to a gel which becomes less resistant to particle propagation at even larger applied field strengths, one would expect that a more refined model could capture this behavior by determining how strongly driven particles may cause local yielding of the gel network. Certainly, one would not expect the model of Eq. (4) to predict velocities at electric field strengths much greater than those we have explored accurately, since it diverges without bound towards higher field strengths when K is negative. In effect, a yield property of the gel network driven by particles exerting a range of forces, not just a compliance related to linear elastic response, would be worth including in future models that are less empirical in origin.

Performing gel-EP using uniformly passivated agarose gels, whether gels that are formed in the presence of the passivation agent or gels that are formed and later treated with a passivation agent, offers certain advantages over passivating the surfaces of nanoparticles. For certain types of passivation agents, desorption of the passivating molecules from the surfaces of the nanoparticles as the nanoparticles propagate through the gel can lead to non-uniform mobility that depends on the distance of propagation of the nanoparticles into the gel. If enough desorption occurs, then the nanoparticles could even become trapped in the gel and would cease to propagate. In other cases, it would be undesirable to modify the surfaces of the nanoparticles, since such modifications could influence the particle mobilities either through increased hydrodynamic drag or steric interactions with the gel network. By contrast, if the gel is homogeneously pre-passivated before nanoparticles are driven into it, modification of the nanoparticle surfaces becomes unnecessary, and nanoparticles propagate readily and uniformly throughout the entire length of the gel. Our comparative studies of PEG1000 and SDS as passivation agents show that non-ionic PEG passivation agents tend to produce passivated gels in which nanoparticle velocities depend only weakly on passivation agent concentration above a threshold, which can be desirable. Although standard agarose gels do not need to be passivated in order to perform nice separations of highly negatively charged biological poly-anions, we nevertheless anticipate that the synthesis of hybrid agarose-PEG polymers would create ideal large-pore gels suitable for electrophoresis of many kinds of nanoscopic charged objects.

Conclusion

By passivating common large-pore agarose gels and using natural scattering of visible light from charged nanoparticles, we have demonstrated that optical-scattering, real-time, video-tracking gel-EP is useful for conducting a quantitative systematic study of the separation of multi-modal dispersions of monodisperse charged SSPS nanospheres. We have measured how the agarose gel concentration, passivation agent type and concentration, and electric field strength affect the electrophoretic mobility of nanoparticles during gel-EP. Our results provide a means of optimizing passivated agarose gel-EP experiments for separating spherical charged SSPS nanoparticles that have radii ranging up to about 150 nm. It is likely that even larger radii can be separated using passivated gel-EP by further reducing the gel concentration and also using additional rigid structural supports for weaker gels.

Interestingly, we find that the response of the velocity of a propagating band of monodisperse particles can become nonlinear in different ways at large E. Larger nanoparticles that are strongly driven at high applied voltages can become trapped in the gel, whereas the same particles still propagate slowly at lower field strengths. However, the smallest nanospheres can have a velocity that becomes super-linear, exhibiting the opposite behavior. Surprisingly, a single semi-empirical equation, based on a simple model of thermally activated barrier hopping, which includes an effective compliance related to a driven particle in a porous elastic gel that has a polydisperse pore-size distribution, can be used to explain $v_p(E)$ from the linear to the non-linear response regions over a wide range of a.

The success of this model, while overly simplistic in terms of lumping many complex effects into a nanoscopic compliance, indicates that further theoretical work is warranted in developing a more sophisticated and rigorous theory of nanoparticle gel-EP. In addition, such a theory, if developed, could potentially explain other observed empirical relationships, such as the inverse dependence $C^*_{gel}(a) \sim a^{-1}$ and the quadratic dependence $v_p(C_{gel}) = v_0 (1 - C_{gel}/C^*_{gel})^2$. These studies of compact objects such as solid nanospheres, which do not have any capacity for internal structural reorganization, in passivated gel-EP may help simplify the theoretical problem of describing gel-EP of biomolecules that can reconfigure internally and change shape.

In order to investigate nanospheres having radii less than 15 nm, ultraviolet light scattering or fluorescence imaging of dye-laden nanospheres could be used to detect bands of uniform particles, since scattering of light at visible wavelengths becomes difficult to detect. In addition, we anticipate that such passivated large-pore agarose gels can be used to separate and determine mobilities of other non-spherical particle types and shapes having overall dimensions similar to those of the SSPS nanospheres we have studied. Although our focus has been on passivated gel-EP of anionic nanoparticles in this work, we also anticipate that large-pore gel-EP using non-ionic or cationic molecules (e.g, such as PEG or cationic surfactants) as passivation agents will also be amenable for separations of positively charged cationic nanoparticles having the same size range. Similarly, while agarose has been used as the gel for these studies, we anticipate that other gel materials that are capable of forming large-pore electrophoretic gels will be useful in separating nanoscale objects.

References for Discussion of Related Art and Example 1

[1] S. Magdeldin, *Gel Electrophoresis—Principles and Basics*. InTech, Rijeka, Croatia, 2012.
[2] J. R. Brody, S. E. Kern, Anal. Biochem. 333 (2004) 1.
[3] S. A. Boffey, in J. M. Walker, *Methods in Molecular Biology*, Humana, Totowa, N.J., 1984, p 333.

[4] W. L. Fangman, Nucleic Acids Res. 5 (1978) 653.
[5] C. R. Calladine, C. M. Collis, H. R. Drew, M. R. Mott, J. Mol. Biol. 221 (1991) 981.
[6] P. H. Johnson, L. I. Grossman, Biochemistry 16 (1977) 4217.
[7] S. V. Lee, A. R. Bahaman, Trop. Biomed. 27 (2010) 351.
[8] D. Rickwood, B. D. Hames, *Gel Electrophoresis of Nucleic Acids: A Practical Approach*. IRL Press Ltd, Washington D.C., 1982.
[9] M. S. Blake, K. H. Johnston, G. J. Russelljones, E. C. Gotschlich, Anal. Biochem. 136 (1984) 175.
[10] W. N. Burnette, Anal. Biochem. 112 (1981) 195.
[11] H. Schagger, G. Vonjagow, Anal. Biochem. 166 (1987) 368.
[12] A. L. Shapiro, E. Vinuela, J. V. Maizel, Biochem. Biophys. Res. Commun. 28 (1967) 815.
[13] M. Unlu, M. E. Morgan, J. S. Minden, Electrophoresis 18 (1997) 2071.
[14] K. Weber, M. Osborn, J. Biol. Chem. 244 (1969) 4406.
[15] R. Westermeier, *Electrophoresis in Practice: A Guide to Methods and Applications of DNA and Protein Separations*. 4th ed., Wiley-VCH Verlag GmbH & Co., 2005.
[16] D. E. Garfin in R. R. Burgess, M. P. Deutscher, Eds. *Guide to Protein Purification*, 2nd ed., 2009, p 497.
[17] H. L. M. Granzier, K. Wang, Electrophoresis 14 (1993) 56.
[18] T. Wehr, R. Rodriguez-Diaz, M. Zhu, *Capillary Electrophoresis of Proteins*. CRC, Boca Raton, 1998.
[19] B. D. Hames, *Gel Electrophoresis of Proteins: A Practical Approach*. Oxford University Press, Oxford, 1998.
[20] M. Cebron A Fau-Coci, J. Coci M Fau-Garnier, H. J. Garnier J Fau-Laanbroek, H. J. Laanbroek, Appl. Environ. Microbiol. 70 (2004) 6726.
[21] R. I. Amann, W. Ludwig, K. H. Schleifer, Microbiol. Rev. 59 (1995) 143.
[22] S. Hjerten, Arch. Biochem. Biophys. 99 (1962) 466.
[23] M. Zweig, S. Barban, N. P. Salzman, J. Virol. 17 (1976) 916.
[24] P. Serwer, S. A. Khan, G. A. Griess, J. Chromatogr. A 698 (1995) 251.
[25] B. Diez, J. Anton, N. Guixa-Boixereu, C. Pedros-Alio, F. Rodriguez-Valera, Int. Microbiol. 3 (2000) 159.
[26] T. Pellegrino, R. A. Sperling, A. P. Alivisatos, W. J. Parak, J. Biomed. Biotechnol. (2007) 26796.
[27] C. Hasenoehrl, C. M. Alexander, N. N. Azzarelli, J. C. Dabrowiak, Electrophoresis 33 (2012) 1251.
[28] N. Surugau, P. L. Urban, J. September Sci. 32 (2009) 1889.
[29] N. Guarrotxena, G. Braun, J. Nanopart. Res. 14 (2012) 1199.
[30] F. Li, R. J. Hill, J. Colloid Interface Sci. 394 (2013) 1.
[31] M. Hanauer, S. Pierrat, I. Zins, A. Lotz, C. Sonnichsen, Nano Lett. 7 (2007) 2881.
[32] B. Kowalczyk, I. n. Lagzi, B. A. Grzybowski, Curr. Opin. Colloid Interface Sci. 16 (2011) 135.
[33] G. A. Griess, K. B. Guiseley, P. Serwer, Biophys. J. 65 (1993) 138.
[34] L. Kremser, D. Blaas, E. Kenndler, Electrophoresis 30 (2009) 133.
[35] E. Klodzinska, B. Buszewski, Anal. Chem. 81 (2008) 8.
[36] V. Kostal, E. A. Arriaga, Electrophoresis 29 (2008) 2578.
[37] B. D. R. Hames in: *Gel Electrophoresis of Proteins: A Practical Approach*.; IRL Press, Oxford, 1987.
[38] A. M. Guilliatt in: B. D. M. Theophilus, R. Rapley, Eds., *PCR Mutation Detection Protocols*; Humana Press Inc., Totowa, N.J., 2002, p 1.
[39] M. Lahaye, C. Rochas, Hydrobiologia 221 (1991) 137.
[40] C. Araki, Bull. Chem. Soc. Jpn. 29 (1956) 543.
[41] N. Ioannidis. Manufacturing of Agarose-Based Chromatographic Media with Controlled Pore and Particle Size. Ph.D. Thesis, University of Birmingham, Birmingham, 2009.
[42] M. Tako, S. Nakamura, Carbohydr. Res. 180 (1988) 277.
[43] S. Arnott, A. Fulmer, W. E. Scott, I. C. M. Dea, R. Moorhouse, D. A. Rees, J. Mol. Biol. 90 (1974) 269.
[44] D. A. Rees, Biochem. J. 126 (1972) 257.
[45] A. Amsterdam, Z. Erel, S. Shaltiel, Arch. Biochem. Biophys. 171 (1975) 673.
[46] R. R. R. Vincent, B. W. Mansel, A. Kramer, K. Kroy, M. A. K. Williams, New J. Phys. 15 (2013) 035002.
[47] Z. H. Mohammed, M. W. N. Hember, R. K. Richardson, E. R. Morris, Carbohydr. Polym. 36 (1998) 15.
[48] N. V. Nucci, J. M. Vanderkooi, J. Mol. Liq. 143 (2008) 160.
[49] N. Kusukawa, M. V. Ostrovsky, M. M. Garner, Electrophoresis 20 (1999) 1455.
[50] M. Maaloum, N. Pernodet, B. Tinland, Electrophoresis 19 (1998) 1606.
[51] P. Aymard, D. R. Martin, K. Plucknett, T. J. Foster, A. H. Clark, I. T. Norton, Biopolymers 59 (2001) 131.
[52] R. Ruchel, R. L. Steere, E. F. Erbe, J. Chromatogr. 166 (1978) 563.
[53] T. K. Attwood, B. J. Nelmes, D. B. Sellen, Biopolymers 27 (1988) 201.
[54] S. Waki, J. D. Harvey, A. R. Bellamy, Biopolymers 21 (1982) 1909.
[55] N. Pernodet, M. Maaloum, B. Tinland, Electrophoresis 18 (1997) 55.
[56] N. Fatin-Rouge, K. Starchev, J. Buffle, Biophys. J. 86 (2004) 2710.
[57] J. Connolly, M. Singh, C. E. Buckley, Physica B: Condens. Matter 350 (2004) 224.
[58] M. Djabourov, A. H. Clark, D. W. Rowlands, S. B. Rossmurphy, Macromolecules 22 (1989) 180.
[59] J. Narayanan, X. Jun-Ying, L. Xiang-Yang, J. Phys.: Conf. Ser. 28 (2006) 83.
[60] M. M. Chui, R. J. Phillips, M. J. McCarthy, J. Colloid Interface Sci. 174 (1995) 336.
[61] J. H. Knox, H. J. Ritchie, J. Chromatogr. 387 (1987) 65.
[62] P. DePhillips, A. M. Lenhoff, J. Chromatogr. A 883 (2000) 39.
[63] Y. Yao, A. M. Lenhoff, J. Chromatogr. A 1037 (2004) 273.
[64] U. Hasse, F. Scholz, J. Solid State Electrochem. 10 (2006) 380.
[65] J.-M. Nedelec, J.-P. E. Grolier, M. Baba, J. Sol-Gel Sci. Technol. 40 (2006) 191.
[66] J. W. Pollard in: J. Walker, Ed. *The Protein Protocols Handbook*; Humana Press, 1996, p 121.
[67] D. Voytas, N. Ke, in: *Current Protocols in Molecular Biology*; John Wiley & Sons, Inc., 2001.
[68] M. J. Waring, J. Mol. Biol. 13 (1965) 269.
[69] L. R. Williams, Biotech. Histochem. 76 (2001) 127.
[70] P. Laing, J. Immunol. Methods 92 (1986) 161.
[71] J. A. Mackintosh, H. Y. Choi, S. H. Bae, D. A. Veal, P. J. Bell, B. C. Ferrari, D. D. Van Dyk, N. M. Verrills, Y. K. Paik, P. Karuso, Proteomics 3 (2003) 2273.
[72] C. R. Merril, Methods Enzymol. 182 (1990) 477.

[73] T. H. Steinberg in: R. R. Burgess, M. P. Deutscher, Eds. *Guide to Protein Purification*, 2nd ed.; Elsevier Academic Press Inc., San Diego, 2009, p 541.

[74] M. Chevallet, S. Luche, T. Rabilloud, Nat. Protoc. 1 (2006) 1852.

[75] W. Wray, T. Boulikas, V. P. Wray, R. Hancock, Anal. Biochem. 118 (1981) 197.

[76] A. Pluen, P. A. Netti, R. K. Jain, D. A. Berk, Biophys. J. 77 (1999) 542.

Example 2: Nanoparticle Size Distributions Measured by Optical Adaptive-Deconvolution Passivated-Gel Electrophoresis In this example embodiment, we image visible light scattered from dispersions of charged spherical nanoparticles propagating through a passivated agarose gel during electrophoresis. By analyzing one-dimensional light intensities along different lanes, we measure the mobility distributions of the nanoparticles and thereby infer their size distributions, which become time-independent after adequate propagation and separation have occurred. For a given large-pore passivated agarose gel, experiments using monodisperse, surfactant-free, sulfate-stabilized, polystyrene nanopheres establish the propagation distance as a function of time for a range of different sphere radii having known surface charges. As bands of monodisperse nanospheres propagate through the gel, the bands become smeared, developing asymmetric tails as some nanospheres experience additional delays compared to others of the same size. After background subtraction, these bands, including their tails, can be fit well using a modified log-normal distribution, yielding deconvolution parameters that vary with propagation distance and transit time. To demonstrate the approach for complex nanosphere dispersions, such as a multi-modal mixture or a broadly polydisperse nanoemulsion, we measure scattered light intensities as a function of propagation distance and time during gel-EP. Iterative deconvolution using a modified log-normal point-spread function, which changes shape according to propagation distance and time, directly yields unsmeared, high-resolution electrophoretic mobility distributions, from which detailed particle size distributions are inferred.

Introduction

A very important characteristic of a colloidal dispersion is its particle size distribution (PSD). The PSD of a dispersion of spherical particles can be expressed as a radial size distribution of the ensemble; this distribution is typically either number-weighted or volume-weighted. The shape of a PSD can affect many properties of the dispersion, such as jamming point in its rheology and degree of optical scattering at different light wavelengths. Thus, precisely characterizing the PSD of a dispersion is typically essential because the PSD can greatly influence the processing and physical properties of a desired final product. For instance, the volume fraction associated with disordered packing or jamming of spheres, $\phi_J$, (i.e. random close packing or maximal random jamming) important for many soft colloidal materials can depend on characteristics of the size distribution. Disordered polydisperse emulsions of spherical droplets are known to have a higher values of $\phi_J \approx 0.71$ associated with the onset of an elastic shear modulus, compared to disordered monodisperse emulsions, which have been shown to have $\phi_J \approx 0.64$. Such differences in $\phi_J$ can be attributed to additional packing efficiency of spheres that can be present in broadly polydisperse emulsions.

Many standard techniques for measuring size distributions of nanoparticles exist; these include: dynamic light scattering (DLS) (B. J. Berne et al., N. A. Clark et al., C. S. Johnson et al.), static light scattering (SLS) (C. S. Johnson et al., C. B. J. de Boer et al., E. L. Weiss et al.), transmission electron microscopy (TEM) (E. M. Slayter et al.), scanning electron microscopy (SEM) (E. M. Slayter et al.), atomic force microscopy (AFM) (P. Eaton et al), and electrical impedance changes via Coulter counting (R. W. DeBlois et al.). Real-space electron microscopy methods are direct and especially well-suited for providing precise size measurements of nanoparticles, independent of their surface charges and hydrodynamic mobilities. Moreover, beyond size, electron microscopy provides access to particle shapes. However, accumulating enough statistics to measure a highly detailed number-weighted size distribution can be difficult and represents a practical limitation of electron microscopy. Other drawbacks of electron microscopy methods include high up-front instrument cost, limited user access, low throughput resulting from sample preparation, and considerable post-acquisition processing of many images is required to obtain adequate statistics for generating a PSD that has reasonably high resolution.

For a number of other methods mentioned above, especially those involving scattering, many particles are sampled to probe a large ensemble, yet determining the size distribution amounts to solving a complicated ill-posed inverse problem that may not have a unique solution or may be biased by the choice of an assumed model. If accurate optical parameters are known, DLS and SLS can generate accurate particles size distribution results for monodisperse spherical particles. However, for SLS, the reported distribution can be skewed towards particles of smaller sizes if the distribution is wide. The accuracy of light scattering methods also strongly depends on knowing in advance the optical parameters of the particles, such as refractive index and light absorption characteristics. Smoothness criteria, which are often part of regularization methods of solving such ill-posed problems when interpreting light scattering results, can hide abrupt irregularities in the size distribution that might be present.

Thus, developing a low-cost, easily accessible, versatile, high-throughput, direct method of determining high-resolution distributions of nanoparticles by a non-microscopic method is still desirable, even given the other existing methods. Real-time optical video tracking of visible light scattering from charged nanoparticles or nanodroplets during passivated agarose gel electrophoresis (gel-EP) (X. Zhu et al.) can potentially be turned into a high-resolution technique for measuring the mobility and size distributions of dispersions of charged nanoparticles.

In this embodiment, we show that images obtained while performing passivated gel-EP separation and imaging, when analyzed using an appropriate and sophisticated deconvolution method, can be used to measure high-resolution, complex size distributions of charged nanospheres and nanodroplets. Since the index of refraction of the nanospheres is known and is significantly different than that of the buffer solution, particle propagation can be easily detected by imaging scattered light from the nanoparticles as they undergo passivated gel-EP. The evolution of the scattered light intensity as a function of distance along the field direction, $I(L,t)$, in a lane corresponding to a well at different observation times t after turning on the electric field is measured, recorded, and converted into an electrophoretic mobility distribution and then a size distribution. We develop and apply an advanced deconvolution algorithm that removes smearing of the size distribution that is a consequence of the complex transport process of the particles moving through the passivated gel in the presence of an applied electric field. Because of the separating power of large-pore passivated gel electrophoresis, this method is especially useful for dispersions that are multimodal mixtures containing several different monodispersed spherical nanoparticles each having different volume fractions. Likewise, as we show, it can be used to measure the broad mobility and size distribution of nanoscale droplets in nanoemulsions, and even broad distribution of a nanoemulsion that has an abrupt peak caused by mixing into it a monodisperse dispersion of polystyrene nanospheres. Because several different dispersions can be loaded in different wells, corresponding to lanes in the gel, imaged, and analyzed simultaneously during electrophoresis, it is possible to obtain multiple size distributions of many different dispersions in parallel, yielding higher throughput. Since the gel electrophoresis apparatus is a common, low-cost device available in many research laboratories, and since digital cameras are also readily available, this passivated gel-imaging-deconvolution method can potentially replace much more expensive approaches.

Materials and Methods

To make a complex multi-modal dispersion of nanospheres, we mix monodisperse dispersions of surfactant-free, sulfate-stabilized, polystyrene (SSPS) nanospheres having several different average number-weighted bare radii and standard deviations in radius: $<a>\pm\delta a$ (nm)=18±2.5, 42±2.5, 70±1.5, and 105±5.5, as determined using electron microscopy (Invitrogen/Interfacial Dynamics Co.). The electrophoretic surface-charge characteristics of each of these nanospheres in aqueous sodium borate buffer (SBB) at pH=9.0 in the absence of any agarose gel and in passivated large-pore agarose gels have previously been measured (X. Zhu et al.). The total effective charge per SSPS nanosphere in the buffer rises approximately linearly with particle radius, with $q_{PS} \approx 10^4$ $e^-$ for $<a>=70$ nm.

We make stable oil-in-water nanoemulsions (T. G. Mason et al.) using a high-refractive index silicone oil, 1,1,5,5-Tetraphenyl-1,3,3,5-tetramethyltrisiloxane (TPTMS, $C_{28}H_{32}O_2Si_3$, $M_w$=484.82 g/mol from Gelest). We first create a polydisperse microscale premix oil-in-water emulsion by mixing TPTMS into an aqueous sodium dodecyl sulfate (SDS) solution using a rotary mixer. This emulsion is passed 9 times through a high-pressure homogenizer (Microfluidizer 110P, 30,000 psi liquid pressure, 75 µm channel size) to rupture the microscale emulsion droplets down to nanoscale and reduce the size polydispersity (T. G. Mason et al, K. Meleson et al.). After emulsification, the TPTMS nanoemulsion droplets are stable against coarsening via Ostwald ripening because the solubility of TPTMS in the aqueous SDS solution is extremely low. Prior to loading into an electrophoresis well, the final SDS concentration of the nanoemulsion is set to be ≈2 mM, below the critical micelle concentration. The refractive index of TPTMS ($n_{TPTMS} \approx 1.56$) is very close to that of the polystyrene nanospheres ($n_{PS} \approx 1.59$). Since water has n=1.33, the refractive index differences are: $\Delta n \approx 0.26$ for SSPS nanospheres and $\Delta n \approx 0.23$ for TPTMS silicone oil nanodroplets. Therefore, because these values of $\Delta n$ are nearly the same, the calibration intensities obtained for monodisperse SSPS nanospheres can be used to a good approximation for TPTMS nanoemulsions as well.

Performing image analysis of scattered light from bands of propagating particles during passivated gel-EP of individual monodisperse dispersions of polystyrene nanospheres has been previously described in detail (T. G. Mason et al.) and above in Example 1.

When performing electrophoresis to measure a particle size distribution, we choose an electric field strength E that is small enough to remain in the linear propagation regime, where steady-state propagation velocities $v_p$ are proportional to E, yet large enough so that clear separation of particles having different sizes occurs over a reasonably short time of about two to three hours. For SSPS nanospheres in PEG-passivated agarose gels in a standard horizontal gel-EP apparatus, this linear region typically extends up to applied voltages of ≈50 V. Although electrophoretic separation can be induced more rapidly at higher voltages, using such high voltages are typically not advantageous because they create complex non-linear behavior in the propagation velocity which can significantly complicate interpretation and deconvolution analysis. Dispersions of nanoparticles or nanodroplets are loaded into separate wells in the passivated large-pore agarose gel. Time-lapse movies of electrophoretically propagating and separating nanoparticles, taken by an overhead digital camera while side illuminating a transparent electrophoresis apparatus using white incoherent light, are recorded. After performing background subtraction of light scattered from the gel, using an initial image of the gel before loading particles into wells, we extract the scattered light intensity from the nanoparticles as a function of distance along the field direction, I(L,t), in each lane corresponding to a well at different observation times t (i.e. after applying the voltage and therefore the electric field). Subsequently, for images at sufficiently large t (e.g. 2 to 3 hours) we perform a advanced form of asymmetric adaptive deconvolution analysis, described below, that has been specifically tailored to correct for asymmetric smearing of I(L) that results from electrophoretic transport of nanoparticles through the gel in the linear velocity-field response regime. In this range of times, the resulting size distributions that are extracted are essentially time-independent. Total volume fractions $\phi_T$ of nano-objects are kept below about 3%, so they are dilute but not highly dilute, in order to assure an adequate light scattering signal but to avoid φ-dependent effects.

Results and Discussion

We perform calibration experiments using highly monodisperse nanospheres in a PEG-passivated large-pore agarose gel to obtain sets of deconvolution parameters which enable us to create what we call an adaptive asymmetric point-spread function (AA-PSF). This AA-PSF is later used to deconvolve mobility and size distributions of nanosphere dispersions that have unknown distributions. The AA-PSF can depend on many factors, including: gel type and concentration, passivation agent type and concentration, buffer type and concentration, conditions of gel solidification, gel porosity and pore size distribution, well dimensions, ionic strength, electric field strength and homogeneity, as well as the shapes, dimensions, volume fractions, and charges of nano-objects to be probed. Here, as an example, we demonstrate the creation of a suitable AA-PSF for charged nanospheres that can be used to deconvolve measured I(L) of a dispersion of nanospheres to obtain ensemble-averaged mobility and size distributions.

There are sound physical reasons why we have developed the AA-PSF analysis method, rather than use a standard, simple, fixed PSF for deconvolving the measured electrophoretic I(L). First, the propagation rate of individual electrophoretically driven nano-objects in a dilute dispersion through a porous gel per length of gel involves stochastic aspects related to collisions of the nano-objects with the gel structure. While being driven, these nano-objects are also thermally excited in a random manner, and such thermal excitations can enable the nano-objects to escape blind alleys and to find porous passageways that are large and/or flexible enough for them to traverse. In principle, this transit problem can be mapped onto a statistical problem related to a time of first passage, $\tau_p$, of driven nano-objects per unit length of gel. For instance, for ideally monodisperse charged spherical nanospheres at dilute concentrations, the vast majority traverse a certain length of the gel over the time of first passage, but a small percentage will require two, three, or more times $\tau_p$, in order to traverse the same distance, as a result of additional collisions with the gel and/or local inhomogeneities in the gel. Thus, a band of monodisperse nanospheres propagating in a lane in the gel is smeared asymmetrically, leading to a trailing tail that is a result of spheres that have required additional time, beyond the typical time of first passage, to traverse the same length of the gel. Residual charge and size polydispersity of the nanospheres could increase the width of a band, associated with a peak in I(L), but the asymmetric skew, leading to noticeable tails associated with the bands, appears to arise from the physical transport process of the nanospheres through the random passageways within the disordered porous gel. Likewise, for similar reasons, the total distance that particles have traversed the gel can affect the width and asymmetry of the point-spread function, so these parameters must be adapted for the distance from the initial starting point in the well (i.e. the width and skew in I(L) increase as L becomes larger and the particles have propagated a greater distance through the gel).

Thus, a useful AA-PSF would effectively correct for different amounts of asymmetric smearing of the measured I(L) that can occur as a result of the complex transport process of the differently-sized particles moving through the porous passivated gel over a distance L, which itself depends on the observation time after applying a voltage and also on average particle radius. Many different functional forms could be used to capture a peak that has an asymmetric tail. For monodisperse SSPS nanospheres propagating in PEG-passivated large-pore agarose gels, we find that a reversed and translated log-normal function can capture the detailed peak structures in the measured I(L) of highly monodisperse SSPS nanospheres, including the asymmetric tails, well over a wide range of <a>. We express this normalized reversed-log-normal AA-PSF as follows:

$$f_{psf}(L) = \frac{1}{\sqrt{2\pi}(L_p + L_m - L)\sigma} \exp(-[\ln((L_p + L_m - L)/L_m)]^2 / 2\sigma^2) \quad (5)$$

for $L < L_p + L_m$ and zero for $L \geq L_p + L_m$, where $L_p$ is a band's peak location relative to the entering edge of a well, a is the band's effective dimensionless width, and $L_m$ is the distance from the peak to the function's zero. Although not explicitly shown, the parameters $L_p$, $L_m$, and a are dependent on <a> and on the time of observation after applying the voltage, t, which can be directly linked to $L_p$ if the steady-state electrophoretic propagation velocity associated with the peak of the band intensity, $v_p$, is known: $t \approx L_p/v_p$ (X. Zhu et al). When used to fit a single narrow monomodal peak in I(L), corresponding to a dispersion of monodisperse spheres, we multiply $f_{psf}(L)$ with a total intensity, $I_{tot}$, which adjusts the height of the normalized function to the intensity scale and has been previously calibrated to the initial loaded SSPS nanosphere volume fraction $\phi$(X. Zhu et al).

We load four individual dispersions of highly monodisperse SSPS nanospheres, having radii ranging from 18 nm to 105 nm, into separate wells in a PEG-passivated large-pore agarose gel. We then perform gel-EP at a temperature of 20° C. in 5 mM sodium borate buffer (pH=9.0), [Agarose]= 0.45% (w/w), [PEG1000]=7.5 mM, and electric field $E=1.6\times10^{-4}$ statV/cm. After starting the electrophoresis and waiting $t=1.5\times10^4$ s, the four different bands of particles have traveled different distances in separate lanes, yet they all remain within the gel in the imaging region, as shown in FIGS. 9(a)-(d):insets. Using the digital camera, we determine the measured I(L) of bands in each lane by averaging the 2D intensity signal perpendicular to the direction of propagation. Also in FIGS. 9(a)-1(d), we plot these measured I(L), averaged horizontally across a lane, along with solid-line least-squares fits, using Eq. (5). The parameter values from the fits are shown in Table 1. Spline interpolation between these fit parameter values for this fixed time t and at these specific electrophoretic conditions for monodisperse spheres enables us to fully express the normalized AA-PSF corresponding to a continuous range of nanoparticle radii that might be present in any arbitrary dispersion, provided charge conditions on the nanoparticles are the same and do not significantly alter their mobilities.

TABLE 1

Fit parameters of the reversed log-normal point spread functions shown in FIG. 9.

| <a> ± δa (nm) | $I_{tot}$ (arb. units) | $L_p$ (mm) | $L_m$ (mm) | σ |
| --- | --- | --- | --- | --- |
| 18 ± 2.5 | 14 | 19.4 | 3.7 | 0.33 |
| 42 ± 2.5 | 72 | 15.2 | 2.7 | 0.28 |
| 70 ± 1.5 | 107 | 7.6 | 1.8 | 0.25 |
| 105 ± 5.5 | 85 | 2.0 | 1.3 | 0.12 |

To demonstrate a method of obtaining a high-resolution, deconvolved, radial particle size distribution, we use the AA-PSF to deconvolve the measured I(L) of a 4-component multi-modal mixture of monodisperse polystyrene nanospheres. By performing PEG-passivated large-pore agarose gel electrophoresis on this multi-modal colloidal mixture at exactly the same conditions, we measure the background-subtracted I(L) at exactly the same time $t=1.5\times10^4$ s that had been used to obtain the AA-PSF. Using a peak detection routine, we detect N discrete peaks, and determine initial estimates of the distance to the centers of the peaks, $L_{p,i}$, peak widths $\delta L_i$, and peak heights intensities $H_i$, where i is an integer index ranging from 1 to N referring to a particular peak. We assume that the deconvolved radial size distribution, and thus deconvolved intensity profile $I_d(L)$, which corrects for the asymmetric tails and broadening resulting from nanoparticle propagation through the gel, can be represented by a sum of N symmetric Gaussian peaks. These initial estimates, together with a prior calibration, which connects the average integrated scattered light intensity to the initial volume fraction $\phi$ of a particular sphere size (i.e. absolute $\phi$ of a monodisperse dispersion loaded into a well) (X. Zhu et al.), provide a starting point for the multi-modal deconvolution analysis.

We update the initial estimate of the deconvolved intensity as a function of propagation distance, $I_d(L)$, iterating until we reach a minimal least-squares deviation between a forward-convolved intensity $I_c(L)$ and the measured intensity I(L). Different than conventional deconvolution (P. A. Jansson et al.), which typically uses a single non-adaptive PSF that does not depend on L, we use the AA-PSF, $f_{psf}(L)$, and convolve it using a custom-written non-standard software routine with a current estimate of the multi-peak deconvolved intensity profile $I_d(L)$: $I_c(L)=I_d(L)\otimes f_{psf}(L)$, recognizing that the convolution symbol here actually implies continuously adjusting parameters of $f_{psf}$, using spline interpolation of parameters obtained for highly monodisperse polystyrene spheres, that control the shape as the AA-PSF is flipped horizontally and moved through different L during the multiplication-integration of the forward convolution. This customized adaptive direct convolution method, not based on Fourier transforms, provides a forward-convolved intensity profile $I_c(L)$, which is only an approximation of the measured I(L) that is smeared out as a result of the stochastic aspect of electrophoretic transport of charged spheres through the random gel. Next, we compare this $I_c(L)$ to the measured I(L), calculating chi-square, $\chi^2$, for a particular discretization in L as we vary $L_{p,i}$, $\delta L_i$, and $H_i$ in the deconvolved distribution. When $\chi^2$ is minimized with respect to these parameters, we report a final convolved intensity profile, $I_c(L)$, as shown in FIG. 11, which closely resembles the measured I(L). Using the known I($\phi$,a), we then convert the deconvolved $I_d(L)$ into a deconvolved probability distribution of nanosphere radii, $p_\phi(a)$, as shown in FIG. 12. This probability density, when integrated with respect to a between $a_1$ and $a_2$, yields the volume fraction of particles in the dispersion loaded into a well (in %) having radii between $a_1$ and $a_2$.

We have obtained a high-resolution radial size distribution by analyzing an image taken at a time t within an optimal range, such that the obtained distribution is effectively steady-state and does not depend on t. If the observation time had been chosen to be too short (i.e. very soon after the electric field has been turned on), not enough separation of different particle sizes would have occurred, and extracting a high-resolution size distribution would have been hampered by inadequate separation. However, if the observation time has been chosen to be too long, bands containing smaller particles may have propagated beyond the observation region or the total gel length. Thus, a near-optimal time of observation for obtaining a high-resolution size distribution corresponds to a time between these two limits such that the deconvolved size distribution of particles remains substantially the same, independent of t. For the multi-modal distribution, the obtained distribution matches well with the actual particle size and volume fraction in the mixture of polystyrene nanospheres that we have created and loaded into the well.

As a second demonstration of using the AA-PSF approach to obtain a high-resolution size distribution, we also determine the size distribution of a broadly polydisperse silicone oil-in-water nanoemulsion, made through high-flow microfluidic emulsification. We perform PEG-passivated agarose gel-EP, using the same conditions as previously described, on a SDS-stabilized silicone oil-in-water nanoemulsion. The nanoemulsion's I(L), obtained from a background-subtracted image, at a near-optimal observation time t=1.8×10$^4$ s is shown in FIG. 13. Rather than observing a set of sharp bands as in the prior multi-modal example, we instead observe a continuous distribution of intensities over a wide range of L. This indicates broad and continuous polydispersity in the mobility and size distribution of nanoscale droplets.

To perform the deconvolution analysis, we use the AA-PSF and I(a,$\phi$) calibration measurements obtained from individual monodisperse SSPS nanospheres. Since the nanodroplets have the same sulfate charge groups as the SSPS nanospheres (which are typically made using emulsion polymerization in a sulfate-surfactant solution) and nearly the same $\Delta n$, to within about 15%, this is a reasonable starting point. Because the surface charge per nanodroplet, $q_{NE}$, may not be exactly the same as the charge on the SSPS nanospheres, $q_{PS}$, even if the nanodroplet and polystyrene nanospheres have exactly the same radius, the electrophoretic mobilities $v_p \sim q/a$ may be somewhat different as a consequence of having differently charged surfaces. Thus, we define an effective nanodroplet radius $a^*=a/(q_{NE}/q_{PS})$ that is not a true bare radius, but rather includes differences in surface charges of the droplets relative to SSPS nanospheres used in the calibrations. We show the AA-PSF deconvolved $p_\phi(a^*)$ of the nanoemulsion in FIG. 14 (inset); the broad distribution can be captured by a log-normal function. In essence, $p_\phi(a^*)$ expresses a deconvolved electrophoretic mobility distribution, which depends both on the sizes and charges of spherical nano-objects. The nanodroplets in each slice of gel are recovered by electrophoretically elute the nanodroplets from the gel into buffer solution in a mini-gel electrophoresis system. By recovering nanodroplets from slices of the gel (marked in FIG. 13) using electrophoretic elution, and measuring average hydrodynamic radii of droplets from each slice using DLS (see Table 2), we determine that $q_{NE}/q_{PS}\approx 1.2$, resulting in a 20% correction of a relative to $a^*$ because of charge differences. We show the resulting nanodroplet size distribution $p_\phi(a)$ in FIG. 14; it is asymmetric and has features that directly correlate with the shape of the measured I(L). We fit the nanoemulsion's measured radial size distribution to a log-normal distribution, given by:

$$p_\phi(a) = \frac{p_\phi^{sc}}{\sqrt{2\pi}\,(a-(a_p-a_w))\sigma_a}\exp(-[\ln((a-(a_p-a_w))/a_w)]^2/2\sigma_a^2) \quad (6)$$

for $a \geq a_p - a_w$ and zero for $a<a_p-a_w$, as shown by the solid line in FIG. 14. The fit yields a peak radius $a_p=40.7\pm0.2$ nm, a lower cutoff in radius $a_w=23.4\pm0.4$ nm, a dimensionless width $\sigma_a=0.64\pm0.02$, and an overall probability scale $p_\phi^{sc}=1.47\pm0.02\%$. Thus, this measured high-resolution deconvolved size distribution clearly demonstrates that a simple nanoemulsion produced through repetitive high-flow emulsification has a broad and nearly log-normal distribution. Because of the separating power of the passivated gel and use of the AA-PSF, the nearly log-normal shape of the nanodroplet size distribution can be unambiguously attributed to the multi-pass high-flow emulsification process. While we have shown an example for an anionic nanoemulsion stabilized by SDS, we have also measured similar log-normal mobility and radial size distributions of cationic nanoemulsions stabilized by dodecyltrimethylammonium bromide (DTAB), made using the same high-flow microfluidic method, by reversing the polarity of the applied voltage on the electrophoresis apparatus.

TABLE 2

Average measured DLS radii <a> of nanodroplets recovered by elution from gel slices after performing passivated gel electrophoresis.

| | Gel Slice No. | | | |
|---|---|---|---|---|
| | 1 | 2 | 3 | 4 |
| <a> (nm) | 88.7 | 66.9 | 43.5 | 32.1 |

Conclusions

By combining three changes to standard gel electrophoresis, namely gel passivation to enable nanoparticle propagation, direct optical measurement of light scattered by propagating particles in separate lanes, and specialized deconvolution using the AA-PSF, while remaining in the linear field-velocity regime, we have demonstrated that it is possible to obtain high-resolution mobility and size distribution measurements of compact nano-object, such as spherical nanoparticles and nanodroplets. We have shown that this approach is useful for measuring high-resolution particle size distributions of dispersions that are multimodal mixtures of several different monodisperse spherical nanoparticles, each having different volume fractions, as well as a broad size distribution of nanoscale droplets in nanoemulsions. While much of the resolution of the resulting size distributions can be attributed to differences in propagation velocities arising from the relative size of the nanoscale objects compared to the larger average pore size, the specialized deconvolution using the AA-PSF enables a further refinement of the measurements to reduce smearing of the distribution by asymmetric tails in I(L) that arise simply from the stochastic nature of the propagation of the charged nano-objects through the passivated gel, not from their true particle size distribution. The combination of high spatial resolution enabled by passivated gel-EP, a high degree of ensemble-averaging over many nano-objects inherent in the scattered light imaging approach, the ability to measure size distributions of many dispersions in parallel in a single experiment, and adaptive asymmetric deconvolution to further refine the size distribution, can make this approach of measuring mobility and size distributions advantageous compared to others.

As with any measurement technique, proper calibrations and care in running the experiments are necessary in order to obtain accurate and precise results. Performing initial calibrations using monodisperse charged nanospheres, which have known surface charge and refractive index, are necessary in order to interpret the measured I(L) optimizing the loaded nanoparticle volume fraction may be necessary, and fabricating of the passivated agarose gel in a highly controlled manner are required to ensure reliable results. These calibrations provide information about the separating power of the gel at a particular agarose concentration and passivation agent type and concentration, as well as yielding parameters for the AA-PSF and the conversion from the background-subtracted I(L) into absolute $p_\phi(a)$. To extend this approach of obtaining absolute size distributions to dispersions of non-absorbing nanoparticles that have $\Delta n$ significantly different than the value used in these studies, other calibration measurements of I(L, $\phi$, a, $\Delta n$) for monodisperse spheres would be needed. If $\Delta n$ is not known but all nanoparticles have the same $\Delta n$, then it is still possible to obtain relative mobility and size distributions p(a) using AA-PSF deconvolution of scattered light signals.

Although this combined approach has proven to be quite versatile for spherical nanoparticles and nanodroplets, it is nevertheless limited in some respects. Thus far, we have obtained size distributions of compact nano-objects up to a maximal spatial dimension of about 300 nm, limited by the pore size of the gel (i.e. lowest gel concentration that can be readily made and manipulated with this type of gel material). However, this value should not be taken as a maximum limit, since we readily anticipate that even larger pore gels, whether made of agarose or not, could be used to extend the approach to measure size distributions up to a micron or larger. Moreover, there are also some practical limitations related to the effective charge per particle; if this becomes too low and the particles are near-neutral, then their propagation will not be rapid enough for the approach to be time-efficient. This could potentially be overcome by loading the nanoparticles into a surfactant solution that could provide an adsorbed surface charge, but the ultimate charge per nanoparticle as a function of nanoparticle size would then require characterization. Furthermore, non-spherical nano-objects that are not highly compact can interact with the porous gel in a manner that is different than compact spherical objects, so further studies would be required to determine how various shapes influence the electrophoretic mobility. Obviously, since this electrophoretic approach is not a direct real-space method, such as SEM and TEM, it cannot provide an exact description of distributions that may contain a wide diversity of shapes, and is instead better suited for dispersions in which a limited number of different types of shapes of the nano-objects is limited and known in advance. However, there are many types of nano-objects for which this limitation is not a major drawback, so this electrophoretic approach still has the potential for wide utility.

The optical imaging approach that we have developed to measure the background-subtracted I(L) in a lane after an adequate temporal period of electrophoresis is appropriate for non-absorbing nanoparticles that have a significant refractive index difference with respect to the buffer solution and are loaded at volume fractions that are large enough that the detected optical signal is significantly larger than the scattering from the gel. It may be necessary to either concentrate or dilute the dispersion prior to loading, as well as adjust the shutter speed of the camera, in order to optimize the scattering signal relative to the gel background and yet still prevent saturation of the intensity in image pixels. Obviously, a transmission or near-backscattering illumination-detection geometry could be used to image strongly optically absorbing nanoparticles. In this case, the regions rich in absorbing nanoparticles will appear darker than regions that are not. Alternatively, fluorescent nanoparticles could be detected by illuminating using shorter wavelength light and detecting only longer wavelength emitted fluorescent light from the nanoparticles. Certain types of plasmonic nanoparticles and quantum dots scatter or emit light that is sensitive to the size and shapes of such nanoparticles, so color imaging of light emanating from particles in a lane can also be used in more accurately determining the deconvolved size distribution.

The asymmetric tail that we observe in the measured I(L) of highly monodisperse nanospheres can be attributed to the stochastic nature of propagation of the nanospheres through a passivated, random, porous gel during electrophoresis. Collisions of the particles with the gel, a distribution of effective pore sizes within the gel, deformation of the flexible gel network by electrophoretically driven particles, and thermal excitations that enable particles to move in directions other than along the field direction could be important factors in determining the exact shape of the tail.

It would be useful to systematically investigate how the structure of the gel, such as the average porosity, pore size distribution, local gel flexibility, and gel-particle interactions affect the average electrophoretic transport and also the parameters of the AA-PSF. It would furthermore be useful to improve theories of compact nanoparticle propagation through passivated gels to predict this asymmetric tail.

Overall, adaptive deconvolution analysis of optical images taken after electrophoretically separating charged nanoparticles can provide high-resolution mobility and size distributions that are quite detailed. Because it is inexpensive and the distributions of many different dispersions can be determined in parallel in the same time period, this approach could potentially rival or even surpass other methods for determining nanoparticle size distributions.

References for Example 2

B. J. Berne, R. Pecora, Dynamic Light Scattering: With Applications to Chemistry, Biology, and Physics. Dover Publications, New York, 2000.
N. A. Clark, J. H. Lunacek, G. B. Benedek, Am. J. Phys. 38 (1970) 575.
C. S. Johnson Jr., D. A. Gabriel, *Laser Light Scattering*. CRC Press, Toronto, 1981.
G. B. J. de Boer, C. de Weerd, D. Thoenes, H. W. J. Goossens, Part. Part. Syst. Charact. 4 (1987) 14.
E. L. Weiss, H. N. Frock, Powder Technol. 14 (1976) 287.
E. M. Slayter, H. S. Slayter, *Light and Electron Microscopy*. Cambridge Univ. Press, New York, 1992.
P. Eaton, P. West, *Atomic Force Microscopy*. Oxford Univ. Press, New York, 2010.
R. W. DeBlois, C. P. Bean, Rev. Sci. Instrum. 41 (1970) 909.
X. Zhu, T. G. Mason, "Passivated Gel Electrophoresis of Charged Nanospheres by Light-Scattering Video Tracking", J. Colloid Interface Sci. (accepted).
T. G. Mason, J. N. Wilking, K. Meleson, C. B. Chang, S. M. Graves, J. Phys.: Condens. Matter 18 (2006) R635.
T. G. Mason, S. M. Graves, J. N. Wilking, M. Y. Lin, Eur. Phys. J. B: Condens. Matter Phys. 9 (2006) 193.
K. Meleson, S. Graves, T. G. Mason, Soft Mater. 2 (2004) 109.
P. A. Jansson ed., *Deconvolution of Images and Spectra*. 2nd ed., Dover, N.Y., 2012.

Example 3: Colloidal Separations by Surface Charge Group Using pH-Controlled Passivated Gel Electrophoresis Because charge-stabilized nanoparticles in an aqueous dispersion have a net charge that depends on pH, it is possible, in principle, to separate mixtures of nanoparticles having identical radii yet different surface charge groups using passivated gel electrophoresis. Here, we experimentally demonstrate this approach for a binary dispersion of two types of anionic polystyrene nanospheres that have nearly identical radii but different sulfate and carboxylate surface charge groups by adjusting the pH of the running buffer used in passivated gel electrophoresis to lie between the different $pK_a$ values of these surface charge groups. In addition, the measured steady-state propagation velocities of both types of anionic nanoparticles as a function of pH can be described well by an equilibrium model of protonation of the surface charge groups as the pH is decreased. Thus, pH-controlled passivated gel electrophoresis provides a powerful means of separating similarly-sized charged colloidal objects that are stabilized by different surface charge groups.

Introduction

Because the electrophoretic mobility of charged molecules and nanoparticles[1-3] that are dispersed in aqueous solutions can depend on the solution's pH, through the degree of protonation or deprotonation of stabilizing charge groups on their surfaces, it is possible, in principle, to separate charged nanoparticles that have identical shapes, sizes, and surface charge densities based simply on the chemistry of the attached surface charge groups. Many types of nanoparticles are stabilized by covalently linked charge groups, such as sulfate, carboxyl, and amidine. A screened short-range electrostatic repulsion between the same types of charge prevents the particles from aggregating[4-7]. The net charge on the nanoparticles depends on the total number, signs, magnitudes, and the percentage of ionization of charge groups on each particle[8]. By adjusting the manufacturing conditions, the surface density of charge functional groups on particles can be varied[9]. Moreover, tuning the percentage of ionization of charge groups, after particle production can ultimately change the net charge on the particles[9-11]. Aqueous dispersions of highly monodisperse polystyrene nanospheres that have different stabilizing surface charge groups, such as sulfate and carboxyl, are readily available in the same sizes and with approximately the same surface density of charge groups, so these would provide an idealized model for exploring pH-dependent electrophoretic colloidal separations.

Acidic groups on the surfaces of polystyrene nanospheres typically have larger $pK_a$ values than that in bulk aqueous solution. This can be attributed to a higher surface free energy of the charged particle-liquid interface[10]. In particular, the $pK_a$ value of the sulfate moiety on the surface of polystyrene nanospheres is around 2 whereas that of the carboxyl moiety is around 5. The substantial difference in hydronium ion concentrations [$H_3O+$] associated with these $pK_a$ values makes it possible for the two types of particles to have different surface charge densities at the same pH condition even for the same surface coverage. This difference would be most apparent when the pH is between the different $pK_a$ values of the different surface charge groups. A number of different buffer systems[12,13] can be used in gel electrophoresis to control the pH value of a dispersion and change the degree of ionization of the surface charge groups, which affects the net charge of each particle. Thus, by performing pH-controlled passivated gel-EP on a mixture of highly monodisperse nanospheres that have different surface charge groups but the same sizes and surface charge densities, it may be possible to demonstrate the separation of these nanoparticles stabilized solely by their stabilizing surface charge groups.

Experimental Methods

All polystyrene nanospheres used are surfactant free and manufactured by Invitrogen. The radii and polydispersities have been measured using electron microscopy by the manufacturer (Table 3). Within the polydispersity, the average radii of these two kinds of nanospheres are the same. All chemicals used to prepare buffer solutions (Table 4) have been purchased from Sigma Aldrich and are used without further purification. We set the pH of the electrophoresis experiment by choosing a buffer system that has a $pK_a$ close to the desired pH values, so the buffer is nearly balanced. We first prepare different types of 5 mM aqueous buffer solutions at their corresponding optimum buffer capacity, i.e. when the pH is equal to the $pK_a$ of the acid group HA-:

pH=pK$_{a(HA-)}$. We prepare PEG-passivated gels using PEG1000 in 5 mM SBB, and then we soak these gels in different 5 mM buffer solutions (which also contains the same PEG1000 concentration [PEG1000] as in the gel initially) for 48 hours to ensure complete buffer exchange. By preparing the gels this way, pH is the only variable, since we maintain the same gel structure and pore size distribution throughout this set of experiments.

TABLE 3

Average radius <a> and standard deviation δa of PS nanospheres having different surface charge groups

| Surface Charge Group | Carboxyl | Sulfate |
|---|---|---|
| <a> (nm) | 41 | 42 |
| δa (nm) | 8.6 | 2.5 |

TABLE 4

Buffer solutions used to set the pH while performing passivated gel-EP of nanospheres

| pH (measured) | Buffer Species | pKa* |
|---|---|---|
| 2.87 | Chloroacetic acid | 2.87 |
| 3.78 | Formic acid | 3.76 |
| 4.78 | Acetic acid | 4.78 |
| 6.12 | 2-(N-morpholino)ethanesulfonic acid (MES) | 6.12 |
| 7.20 | 3-(N-morpholino)propanesulfonic acid (MOPS) | 7.20 |
| 8.00 | 3-[4-(2-Hydroxyethyl)-1-piperazinyl]propanesulfonic acid (HEPPS) | 8.00 |
| 9.31 | N-Cyclohexyl-2-aminoethanesulfonic acid (CHES) | 9.30 |

We record time-lapse videos of bands of scattered light from monodisperse sulfate- and carboxyl-stabilized polystyrene nanospheres at a loaded total particle volume fraction of 0.4% propagating in passivated agarose gels in buffer solutions at different pH values in the linear propagation regime at an applied voltage (measured) of 57 V. Images of the gels are taken in real-time until the band propagation has reached a steady state. Digital band-tracking analysis provides the distance of propagation of bands of monodisperse particles from the starting well locations as a function of time, and fits of these band trajectories yield the particle's propagation velocity $v_p$ as a function of pH.

Results and Discussion

We change the buffer's pH and measure $v_p$(pH) in PEG-passivated large-pore agarose gels for separate individual dispersions of either sulfate- or carboxyl-stabilized nanospheres, as shown in FIGS. 15(a) and (b), respectively. At high pH, $v_p$ does not change, within the experimental uncertainty; however, as the pH is reduced, there is a noticeable decrease in $v_p$, reflecting increasing protonation (i.e. neutralization) of the surface charge groups on the nanospheres. The onset of this decrease in $v_p$ as pH is reduced is first apparent for carboxyl-stabilized nanospheres around pH≈5, and then it becomes noticeable for sulfate-stabilized nanospheres around pH≈3.

To capture the trends shown in FIG. 15, we consider the acid-base chemical equilibrium of a particular anionic surface charge group having a certain pK$_a$ value populating the surfaces of the polystyrene nanospheres. This effectively corresponds to the classic description of the pH-dependent percentage of ionization. The following reactions reflect the equilibrium between protonated (i.e. neutral) and deprotonated (i.e. charged) acidic surface groups: —COOH+ $H_2O$ ⇔ —COO$^-$+$H_3O^+$ and —OSO$_3$H+$H_2O$ ⇔ —OSO$_3^-$+$H_3O^+$. The plateau velocity as a function of pH is proportional to the percentage of ionization of surface charge groups:

$$v_p(pH) = v_{p,h}/(1+10^{pKa-pH}), \quad (7)$$

where the fit parameters are: pK$_a$ of the surface charge groups and $v_{p,h}$, the saturation plateau velocity in the limit of high pH (see FIG. 15 caption). The measured $v_{p,h}$ for both sulfate- and carboxyl-stabilized polystyrene nanospheres are about the same at high pH values (pH>7). Thus, because $v_{p,h}$ for these two types of polystyrene nanospheres are essentially the same within experimental uncertainty at high pH and their sizes are also essentially the same, we deduce that the density of sulfate and carboxyl surface charge groups are also the same. The values of pKa for the two different surface charge groups that we obtain from the fits are shown in Table 5.

TABLE 5

Measured pKa values of carboxyl (C) and sulfate (S) charge groups on monodisperse PS nanospheres.

| Surface Charge Group | pKa$^C$ | pKa$^S$ |
|---|---|---|
| Measured | 4.6 | 2.9 |
| Manufacturer* | ~5 | ~2 |

*These approximate pKa values are from the manufacturer Invitrogen.

To demonstrate that passivated gel-EP can be used to separate of a mixture of nanoparticles having two different surface charge groups, but identical sizes and surface charge densities, we make a 1:1 mixture of sulfate- and carboxyl-stabilized polystyrene nanospheres and perform passivated gel-EP at a pH that lies in between the pKa values of the two different surface charge groups. At a pH=4.76, between the pK$_a^S$ of the sulfate group and the pK$_a^C$ of carboxyl group, two bands can be clearly seen in the lane corresponding to the mixture (see rightmost lane in FIG. 16a). As a control experiment, we also examine the propagation of the mixture at higher pH≈6.2 above the pKa's of both charge groups, so both types of surface charge groups are effectively deprotonated. At this pH, there is only a single band that can be seen in the lane corresponding to the mixture after performing passivated gel-EP (see rightmost lane in FIG. 16b). Thus, colloidal separations of nanoscale objects based on charge group type can be made using passivated gel-EP, provided that the pH of the buffer is controlled and lies between the pKa's of the surface charge groups. Consequently, even if the types of surface charge groups are unknown for nano-objects in a dispersion, it is possible to perform passivated gel-EP at several different pH values to separate and collect differently stabilized nano-objects that have different surface chemistries (i.e. charge groups). This approach is most viable when the pKa values of different surface charge groups are well separated; it would be more difficult to separate if the pKa values of the surface charge groups differed by less than about 0.5.

Correspondingly, based on these results for a mixed dispersion of colloidal particles stabilized by two different anionic surface charge groups, we anticipate that similar separations can be made for a mixed dispersion of colloidal particles stabilized by two different cationic surface charge groups. In this case, the cationic particles would propagate well at higher pOH (i.e. lower pH), but when the pOH is reduced to near and below the pK$_b$ value of the surface charge group, then the electrophoretic velocity would be significantly reduced as a result of hydroxylation. In this case, for good separations of cationic particles, the pOH should be adjusted to lie between the $pK_b$ values of the different cationic surface charge groups.

In addition, regardless of the sign of the surface charge groups, by combining pH control with deconvolution analysis of images of the intensity distribution in a lane after performing passivated gel-EP, pH-dependent electrophoretic mobility distributions can be measured. One important aspect of a mobility distribution is the type of surface charge group used to stabilize the particles. A second important aspect is the density of surface charge groups, irrespective of the type of surface charge group. Thus, based on our results, we readily anticipate that charge-stabilized nanospheres that have widely different surface charge densities, yet the same radius and stabilizing charge group type, in a mixture can also be effectively separated and relative populations determined by image analysis even at a single pH.

Conclusion

We have demonstrated that pH-controlled passivated gel-EP can be used to efficiently separate mixed dispersions of colloidal nanoparticles that have different surface charge groups yet the same shapes, sizes, and surface charge densities. Such separations based on surface chemical functionality are typically difficult to acheive without introducing attractive interactions between the surfaces of colloids (e.g. using a binding agent) and then subsequently unbinding the colloids, which is more laborious.

References for Example 3

1. Adamson, N. J.; Reynolds, E. C., Rules Relating Electrophoretic Mobility, Charge and Molecular Size of Peptides and Proteins. *J. Chromatogr. B* 1997, 699, 133-147.
2. Sparks, D. L.; Phillips, M. C., Quantitative Measurement of Lipoprotein Surface Charge by Agarose Gel Electrophoresis. *J. Lipid Res.* 1992, 33, 123-130.
3. Tung, J. S.; Knight, C. A., Effect of Charge on the Determination of Molecular Weight of Proteins by Gel Electrophoresis in Sds. *Biochem. Biophys. Res. Commun.* 1971, 42, 1117-1121.
4. Israelachvili, J., *Intermolecular and Surface Forces*; 2nd ed.; Academic: San Diego, 1991.
5. Derjaguin, B.; Landau, L., Theory of Stability of Strongly Charged Liophobic Sols and of the Adhesion of Strongly Charged-Particles in Solutions of Electrolytes. *Prog. Surf. Sci.* 1993, 43, 30-59.
6. Derjaguin, B.; Landau, L., Theory of Stability of Highly Charged Liophobic Sols and Adhesion of Highly Charged Particles in Solutions of Electrolytes. *Zhurnal Eksperimentalnoi Teor. Fiz.* 1945, 15, 663-682.
7. Verwey, E. J. W.; Overbeek, J. T. G., Theory of the Stability of Lyophobic Colloids; Elsevier: Amsterdam, 1948.
8. Behrens, S. H.; Christi, D. I.; Emmerzael, R.; Schurtenberger, P.; Borkovec, M., Charging and Aggregation Properties of Carboxyl Latex Particles: Experiments Versus Dlvo Theory. *Langmuir* 2000, 16, 2566-2575.
9. Zhu, S.; Panne, U.; Rurack, K., A Rapid Method for the Assessment of the Surface Group Density of Carboxylic Acid-Functionalized Polystyrene Microparticles. *Analyst* 2013, 138, 2924-2930.
10. Subir, M.; Liu, J.; Eisenthal, K. B., Protonation at the Aqueous Interface of Polymer Nanoparticles with Second Harmonic Generation. *J. Phys. Chem. C* 2008, 112, 15809-15812.
11. Gisler, T.; Schulz, S. F.; Borkovec, M.; Sticher, H.; Schurtenberger, P.; D,ÄôAguanno, B.; Klein, R., Understanding Colloidal Charge Renormalization from Surface Chemistry: Experiment and Theory. *J. Chem. Phys.* 1994, 101, 9924-9936.
12. Brody, J. R.; Kern, S. E., History and Principles of Conductive Media for Standard DNA Electrophoresis. *Anal. Biochem.* 2004, 333, 1-13.
13. Zhao, M.; Sun, L.; Fu, X.; Gong, X., Influence of Ionic Strength, Ph, and Sds Concentration on Subunit Analysis of Phycoerythrins by Sds-Page. *Appl. Biochem. Biotechnol.* 2010, 162, 1065-1079.

Example 4: High-Throughput Electrophoretic Colloidal Separator

In many types of colloidal synthesis, whether via top-down or bottom-up approaches, the resulting dispersion of colloids has significant polydispersity in at least one of size, shape, charge, and electrophoretic mobility. Many naturally occurring colloidal dispersions also have a wide diversity of colloidal and molecular components and therefore polydispersity in the characteristics, too. In a few limited cases, it is possible to produce colloidal dispersions that have a high degree of monodispersity. However, these methods often require extremely fine control over an expensive synthetic procedure and apparatus. Typically, it is desirable to produce dispersions that are highly monodisperse, so that there is a very narrow distribution and the polydispersity is small. This monodispersity can increase the uniformity of product characteristics. Thus, it would be desirable to create a colloidal separator that operates continuously and separates a polydisperse dispersion that is continuously fed into the separator into a discrete set of highly uniform dispersions, wherein each uniform dispersion has a low polydispersity.

In this example embodiment, based on passivated gel electrophoresis of charged colloidal objects, we have developed a colloidal separator device that separates a polydisperse dispersion of colloidal objects using a passivated gel (e.g. a PEG1000-passivated large-pore agarose gel). We have demonstrated that colloidal objects contained in narrow bands (e.g. less than about several millimeters along the applied electric field direction) of one lane of the slab of passivated gel (e.g. after electrophoretic separation has been performed using a first electric field over an adequate temporal duration to separate objects having different mobilities and/or sizes), can be driven out of the slab using a second electric field that is perpendicular to the first electric field, yet limited in spatial region along the prior electrophoretic field direction, yielding a dispersion having higher monodispersity that is no longer in the passivated gel. Moreover, separation of charged nanoscale objects can be readily achieved by applying a first electric field to cause said objects to separate in a passivated gel, and either concurrently or subsequently applying a fluid flow of the buffer solution through the passivated gel in a direction that contains at least a velocity component that is perpendicular to the direction of the applied electric field to cause said nanoscale objects to propagate across electric field lines in said passivated gel to facilitate collection of separated nanoscale objects. Beyond homogeneous passivated gels that are cast using a uniform concentration of gel material (e.g. agarose), this approach can be applied to passivated gels that have been gelled to form a solid gel yet in which there is a spatial gradient in gel concentration and thus also a spatial gradient in pore size distribution in the gel. We describe several embodiments a device and method that continuously separates small-scale colloidal, nanoscale, and molecular-scale charged objects in a polydisperse input colloidal dispersion in a fluidic input stream into two or more output colloidal dispersions of subsets of said small-scale objects in a set of fluidic output streams in a manner that improves the uniformity of the small-scale objects in said output colloidal dispersions. Because of the continuous nature of the operation of this device, over time, it is possible to process large volumes of the input colloidal dispersions in order to obtain significant volumes of a discrete set of output colloidal dispersions that are more uniform in at least one of size, shape, charge, and electrophoretic mobility than said input colloidal dispersion. While our description is primarily based around a cylindrical geometry (e.g. having a radial direction r and an orthogonal axial direction z, assuming azimithal symmetry), mainly because this cylindrical geometry provides the advantage of reducing cost associated with the quantity of the passivated gel, the same approach could be carried out using at least two of three orthogonal directions in a Cartesian geometry (e.g. having orthogonal directions x, y, and z).

An annular-cylindrical slab of a passivated gel has a ring-like or tube-like form and it can be cast in a manner similar to the preparation of a rectangular slab passivated gel, except the mold used for casting the gel has an rigid inner tube size that sets the inner radius of the annular-cylindrical slab of passivated gel and an rigid out tube size that sets the outer radius of the annular-cylindrical slab of passivated gel. According to an embodiment of the current invention, a total electric field composed of two orthogonal electric fields, a first radial electric field $E_r$ along a radial direction r that decreases with |r| as $E_r(r) \sim 1/|r|$ which effectively separates small-scale colloidal objects in a passivated gel along r and a second electric field $E_z$ along an axial direction z that effectively drives small-scale colloidal objects out of a annular-cylindrical slab of passivated gel for collection by a discrete number of spatially segregated annular collection wells arranged at a surface of the annular-cylindrical slab of passivated gel. A continuous input feed of small-scale colloidal particles in an input dispersion is arranged in a narrow annular input well that has been fabricated in the opposite surface of the annular-cylindrical slab of passivated gel.

The decay in the field strength of the radial field $E_r(r) \sim 1/|r| \times$ where |r| is a radial distance from the axis of a cylinder at |r|=0, is a natural consequence of a solution of Maxwell's equations of electricity and magnetism when applying a radial voltage $V_r$ across a pair of a first radial electrode and a second radial electrode to produce an electric field $E_r$ along r. A first radial electrode is arranged on the inside (i.e. along the inner radius or axis) of the annular-cylindrical slab of passivated gel and a second radial electrode is arranged on the outside (i.e. along the outside of the curved body of the outer cylinder) of the annular-cylindrical slab of passivated gel) and $V_r$ is applied between said first and said second radial electrodes with a polarity that causes the small-scale colloidal objects to propagate electrophoretically outward along the +r direction. The velocity of propagation of particles having a size greater than a certain size in a gel vanishes for a certain value of field strength in a passivated gel having a certain gel concentration and passivation agent concentration, so this type of radial field, that possesses a gradient in radial field strength that decreases as r increases, will still force smaller colloidal objects to propagate out to larger radial distances, so separation of differently sized colloidal objects can occur, but these colloidal objects slow down as they propagate to larger values of r. By contrast, larger colloidal objects will remain at smaller radii under the same conditions of the applied radial electric field, and since the field strength is higher near the inner radius than near the outer radius of the passivated gel, these larger colloidal objects will continue to separate efficiently even as the smaller colloidal objects slow down towards the outer radius of the passivated gel.

In an embodiment of the current invention (FIG. 17), a radial field in the form of $E_r(r) \sim 1/|r|$ is combined with a uniform axial field $E_z$, where the magnitude of said axial field is large enough to drive all sizes of small-scale colloidal objects along the z-direction out of one end of the annular-cylindrical slab of passivated gel. Said axial field is produced by applying an axial voltage $V_z$ across a first axial electrode which is arranged proximate to a first input end of said annular-cylindrical slab of passivated gel and a second axial electrode, which is arranged proximate to a second output end of said annular-cylindrical slab of passivated gel. The voltages $V_r$ and $V_z$, as well as the axial length $L_z$, the inner radius $r_1$ of the inner electrode, the outer radius $r_2$ of the outer electrode, the radius $r_0$ associated with the annular loading well (which is typically is proximate to $r_1$), as well as the gel concentration $C_{gel}$, passivation agent concentration $C_{pass}$, and pH, are adjusted such that separation of the small-scale objects, which are introduced near the inner radius of said first input end of said annular-cylindrical along the radial direction caused by $E_r$ has substantially occurred before the radially separated small-scale objects are driven by $E_z$ along the axial direction out of the annular-cylindrical slab of passivated gel near said second output end into said discrete set of output annular collection wells arranged proximate to second output end. A schematic diagram of an embodiment of said colloidal separator is shown in FIG. 17. In FIG. 17, an input dispersion containing small-scale objects to be separated is continuously circulated by fluidic means (e.g. tubing) from an input reservoir into the region of the annular input well, so that small-scale objects in the input dispersion can move into the passivated gel at substantially the same input radius at the input end of the annular-cylindrical slab of passivated gel so that said small-scale objects are electrophoretically separated by a radial electric field. An axial electric field moves the radially separated small-scale objects through the gel into a discrete number of annular collection wells that are a part of an output collection plate. Each annular output collection well is connected by fluidic means (e.g. tubing) to a corresponding collection reservoir that holds each of the output dispersions of separated small-scale objects. In the FIG. 17, 173=an Annular Dispersion Input Well: proximate to radius $r_1$ and proximate to input end z=0, 174=an Inner Radial Electrode: Electrical conductor proximate to radius $r_1$, 175=an Outer Radial Electrode: Electrical conductor proximate to radius $r_2$, 176=a First Axial Electrode: Electrical conductor proximate to input end z=0, 177=a Second Axial Electrode: Electrical conductor proximate to output end z=$L_z$, and 178=a Collection Plate with a discrete # of annular collection wells (5 annular collection wells are shown in this example).

FIG. 18 shows a schematic diagram showing example propagation trajectories of small-scale colloidal objects having several different electrophoretic mobilities as they are separated and collected by a continuous colloidal separator operating according to the principles explained herein using an embodiment of a colloidal separator device. In FIG. 18, 181=a+Radial Electrode near r=$r_2$, 182=an Annular-Cylindrical Slab of Passivated Gel, 183=a−Radial Electrode near $r=r_1$, 184=an Annular Dispersion Input Well at $r=r_0$, 185=a−Axial Electrode: near $z=0$, and 186=a+Axial Electrode: near $z=L_z$.

Motion of a Sphere Driven in a Cylindrical Gel Electrophoresis Apparatus

In an embodiment of the current invention, we assume that a colloidal object to be separated is a sphere having a radius a and a total net charge q. The charge q can depend on the radius a of the sphere, for instance through a surface charge density on said sphere.

The cylindrical gel-EP geometry (e.g. an annular cylindrical container made of a plastic material that contains an annular-cylindrical volume of a passivated gel) has: an inner electrode having an inner radius, designated as $r_1$; an outer electrode having an outer radius, designated as $r_2$; and a location of an annular loading well, providing an initial radius, $r_0$, of said sphere loaded into said annular loading well. Here, we assume that $r_2 > r_1$ and $r_1 < r_0 < r_2$. An annular cylindrical slab of a passivated gel is placed to occupy the space between said inner and outer electrodes, and the apparatus is filled with a buffer solution. The relative dielectric permittivity of the combination of the gel and the buffer medium is $\varepsilon_r$, and, for these experiments in aqueous buffer solutions with agarose gels, $\varepsilon_r$ typically has a value near the dielectric permittivity of water, which is about 80.

A voltage $V_{app,r}$ is applied between said inner electrode and said outer electrode, creating a radially dependent voltage $V(r) = V_{app,r}[\ln(r/r_2) - \ln(r_1/r_2)]$, where r is the instantaneous radial position of the sphere at time t in the gel between the two electrodes, so the displacement field along the radial direction $D_r$, which is related to the radial component of the electric field $E_r$ by $D_r = \varepsilon_r E_r$, is given by $D_r(r) = -dV(r)/dr = -V_{app,r}/r$. Consequently, the electric field along the radial direction, which creates a force on a charged sphere, is $E_r(r) = -(V_{app,r}/\varepsilon_r)/r$. This applied voltage is typically a DC voltage; however, in some cases, it can be an AC voltage. Thus, the force $F_{el,r}$ along the radial direction associated with the radial electric field acting on the charged sphere in the dielectric medium in this cylindrical geometry is: $F_{el,r}(r) = qE(r) = -qV_{app,r}/(\varepsilon_r r)$.

The combination of the porous gel and buffer create an environment around the sphere that can be modeled as an effective viscosity $\eta_{eff}$ that depends on the radius of the sphere (i.e. relative to a length characterizing holes of a pore structure in the porous gel). Accordingly, the Stokes drag force $F_{d,r}$ on the sphere along the radial direction is $F_{d,r} = -6\pi\eta_{eff}a(dr/dt)$, where $dr/dt$ is the time derivative of the instantaneous radial position of the sphere.

For steady-state propagation of the sphere in the gel, we can ignore initial transitients arising from inertial effects. We also neglect random thermal forces explicitly, assuming any dependence from these is implicitly accounted for through the effective viscosity $\eta_{eff}$. Consequently, the equation of motion along the radial direction for the sphere resulting from force balance is: $0 = F_{el,r} + F_{d,r}$, yielding the following differential equation for r(t):

$$6\pi\eta_{eff}a(dr/dt) = -qV_{app,r}/(\varepsilon_r r).$$

Separation and integrating between an initial radius $r_0$ at initial time $t=0$ and a final radius r at time t then gives (using prime notation for variables of integration):

$$\int_{r_0}^{r} 6\pi\eta_{eff}ar'dr' = -q(V_{app,r}/\varepsilon_r)\int_0^t dt'.$$

Performing the integration and solving this for the time-dependent radial position of the sphere gives:

$$r(t) = [r_0^2 - qV_{app,r}t/(3\pi\varepsilon_r\eta_{eff}a)]^{1/2}.$$

Here, we note that if the voltage is applied in a manner such that the positive terminal is the outer electrode and the negative terminal is the inner electrode, for anionic spheres having a net negative charge, the sign of the second term inside the square root will be positive, and the spheres will propagate outward from $r_0$ towards $r_2$.

In order to simplify the equation, we define a characteristic time, $\tau$, which is positive, as:

$$\tau = r_0^2/[(|qV_{app,r}|)/(3\pi\varepsilon_r\eta_{eff}a)],$$

and the equation describing the time-dependent radial position r of a sphere in the gel at time t after the voltage has been applied can simply be written as:

$$r(t) = r_0(1 + t/\tau)^{1/2}.$$

Consequently, the instantaneous radial velocity $v_r$ of the sphere at time t is: $v_r(t) = dr/dt = (r_0/2\tau)/(1 + t/\tau)^{1/2}$. This instantaneous radial velocity decreases over time as the sphere propagates away from the inner radius. Because smaller spheres have lower $\eta_{eff}$ than larger spheres in the porous gel, the smaller spheres will slow down as they reach larger radii and not propagate out of the gel region as rapidly as if the spheres would be in a standard gel electrophoresis device where the electric field strength is roughly constant everywhere in the gel. This feature, which permits the total volume of the gel to be smaller and thus cost less, while still achieving useful separations of colloidal particles in the gel, is non-obvious and practically advantageous for performing separations.

If one desires the total propagation time for small spheres and large spheres to be the same before both types of spheres exit the gel region and enter the collection region of separate annular wells, then it can be desirable for an annular collection well for a larger sphere, which does not propagate as rapidly, to be placed axially closer to the annular loading well; and an annular collection well for a smaller sphere, which propagates more rapidly, to be placed axially further from the annular loading well. In some embodiments of the current invention, the radial width of an annular collection well is purposefully made to be different at different radii r measured from the axis of the annular-cylindrical separator device. Using different radial widths of annular collection wells facilitates the selection of different separating powers (i.e. how finely the particles are separated). Typically, larger radial widths of annular collection wells provide less separating power, whereas smaller radial widths of annular collection wells provide greater separating power. The number of particles collected per unit time, $dN(r)/dt$, in an annular collection well at a radius r having a radial width $\Delta r$ can be estimated by the product of the flux of separated particles (i.e. number of particles per unit time per unit area) arriving at the annular collection well at radius r, designated by $J(r)$, times the area of the annulus of the annular collection well, given approximately by $2\pi r\Delta r$, so $dN(r)/dt = 2\pi r\Delta r J(r)$. In some embodiments of the current invention, the radial widths of the annular collection wells at different radii of the annular-cylindrical device have been optimized to provide a combination of a desired separating power with a desired rate of collection of separated particles.

In FIG. 19, we present a time series of images showing the stable propagation of a circular band of monodisperse carboxyl-stabilized polystyrene nanospheres in a cylindrical gel apparatus having radius a=41 nm and approximate charge $q \approx 600$ e loaded at an initial volume fraction of 0.15% into the annular loading well. The passivated gel is a large-pore type I-A low EEO agarose gel at a 0.3% w/w concentration and the PEG1000 concentration is 5 mM. The buffer is sodium borate buffer (SBB) at 5 mM, corresponding to pH=9.0. The applied voltage is $V_{app,r}$=50 V, and the positive terminal is at the outer Pt-wire electrode at $r_2$=56 mm, whereas the negative terminal is at the inner Pt-wire electrode at $r_1$=4.4 mm. The annular loading well has a radius $r_0$=12.7 mm, and the thickness of the gel slab is $L_z$=12 mm. This experiment demonstrates that the outward-propagating ring is stable, which was not previously known for electrophoresis of a continuous ring of particles in a cylindrical-annular gel electrophoresis configuration. This is important and non-obvious, because the propagating ring could have become unstable as it expands in size, and such an instability would ruin the separating power of a separating device based on this kind of geometry.

In FIG. 20, we show data points for the radial position of the band of propagating spheres as a function of time, r(t), from FIG. 19. The measured r(t) is not linear, and this is very different than what is commonly observed in standard gel-EP devices for which propagation distance along a Cartesian direction is typically proportional to time. We fit the measured r(t) to the functional form $r_0(1+t/\tau)^{1/2}$, and the quality of the fit is excellent (i.e. the correlation coefficient R=0.999 is very close to unity). From the fit, we determine the fit parameters to be $r_0$=7.2±0.1 mm, which matches our experimental initial radius of the loading well, and $\tau$=106±3 s. This example demonstrates that the decreasing electric field strength as a function of radius away from the axis of the cylinder causes particles to propagate more slowly as they move outward towards the larger radius $r_2$ of the annular-cylindrical gel-EP device. Thus, the decrease in the strength of the electric field at larger radii r provides a means of slowing down particles that have higher electrophoretic mobilities and keeping them in the gel region at larger radii closer to $r_2$ while particles that have lower electrophoretic mobilities are given more time to separate at smaller radii, closer to $r_0$.

In FIG. 21, we show a time-sequence of top-view images taken with the camera above an annular-cylindrical electrophoresis apparatus made of a clear polymer (plexiglas), as described previously for FIG. 19. The loaded dispersion is a mixture of three types of monodisperse polystyrene spheres having particle radii a=42 nm (sulfate-stabilized), 55.5 nm (carboxyl-stabilized), and 70 nm (sulfate-stabilized). The gel is 0.3% w/w Benchmark Scientific molecular grade agarose with 5 mM PEG-1000 and 5 mM sodium borate buffer at pH=9. These images have not been background subtracted, so some scattering from the side walls of the apparatus, from the gel and from bubbles can also been seen. At time t=0 s, all of the input dispersion has been loaded into the annular loading well and the radial voltage of ≈50 V is applied to create an electric field along the radial direction. At time t=900 s, the 42 nm and 55.5 nm spheres have propagated more rapidly to larger radii and have been clearly separated from the 70 nm spheres. Later, at time t=1800 s, three distinct rings are clearly seen, so all three sizes of spheres have been separated into rings that scatter light at different radii. In FIG. 22, arrows point out the three distinct rings of scattering, which demonstrate that an annular-cylindrical geometry employing a passivated gel and circular wire electrodes placed at inner and outer radii can be used to electrophoretically separate a mixed dispersion that contains several different sizes of charged nanoscale objects.

To achieve enhanced separation of particles having different radii using DC fields in a gel electrophoresis device, including an annular-cylindrical device geometry, in some embodiments of the current invention, it is desirable to create a gradient in an electric field that is applied in a second direction that is orthogonal to an electric field applied in a first direction. For instance, in an annular-cylindrical geometry, where $E_r(r) \sim r^{-1}$, is advantageous to create an r-dependent gradient in the electric field along the axial z-direction, $E_z$. For example, the z-dependent electric field can be of the form: $E_z(r)=E_{app,z,0}(r/r_0)$ where $E_{app,z,0}$ is the electric field in the z-direction at the loading well where $r=r_0$. To stay in the linear propagation regime over the entire range of radial and axial displacements, it can be desirable to keep $E_{app,z,0}(r_2/r_0)$ less than the field strength where the onset of non-linear propagation velocity as a function of field strength occurs. The r-dependent gradient in the electric field in the z-direction can be implemented, for instance, by arranging two complementary sets of circular Pt conductors (e.g. wires) on the top and bottom plates, respectively, of the annular-cylindrical electrophoretic separator apparatus, such that independent controlled voltages, which increase linearly with the distance away from the axis of the cylindrical geometry, are applied between pairs of circular electrodes positioned on top and bottom annular plates that are arranged opposite to each other.

In this case, when a radial gradient in the electric field along the radial direction is present $E_r(r) \sim r^{-1}$ and a radial gradient in the electric field along the axial direction $E_z(r)$ is also present, for a given sphere radius a, the trajectory of a sphere, initially loaded into the annular loading well at z=0 and $r=r_0$ can be determined by solving for r(t) and z(t) for a set of different times t after applying voltages both along the r-direction and along the z-direction. As we have previously demonstrated, in the radial direction, $r(t)=r_0(1+t/\tau)^{1/2}$. Consequently, for a particular sphere radius, along its trajectory, $E_z(t)=E_{app,z,0}(1+t/\tau)^{1/2}$. Since z(t) is the time-integral of the z-component of the velocity of the sphere, $v_{p,z}(t)$, and $v_{p,z}(t)=-qE_z(t)/(6\pi\eta_{eff}a)$, through the balance of the resistive drag with the driving electric force, then:

$$z(t)=\int_0^t v_{p,z}(t')dt'=[(qE_{app,z,0}/(9\pi\eta_{eff}a)]\tau[(1+t/\tau)^{3/2}-1],$$

where $E_{app,z,0}=V_{app,z,0}/(L_z \varepsilon_r)$, $V_{app,z,0}$ is the voltage applied between the first set of circular electrodes arranged opposite each other on the top and bottom plates at a radius $r_0$, and $L_z$ is the distance between the top and bottom plates. Because the integration causes the additional factor of $\tau$ to appear in the expression for z(t), as compared to r(t), and since $\tau$ depends on a, then trajectories of spheres having different sizes will follow different electrophoretic streamline trajectories and can be readily separated by collection wells that are spatially arranged to collect particles that arrive in certain spatial ranges of (r, z) locations.

In an embodiment of the current invention, to achieve separations of colloidal objects that are supplied to the device using a fluidic input (either in a continuous or a pulsed manner) into a loading well, the separation and collection steps can be performed in a cyclic manner. An input dispersion containing small-scale objects to be separated is continuously circulated by fluidic means (e.g. plastic tubing) from an input reservoir into the region of the annular input well, so that small-scale objects in the input dispersion can move into the passivated gel at substantially the same input radius at the input end of the annular-cylindrical slab of passivated gel so that said small-scale objects are electrophoretically separated by a radial electric field. An axial electric field moves the radially separated small-scale objects through the gel into a discrete number of annular collection wells that are a part of an output collection plate. Each annular output collection well is connected by fluidic means (e.g. tubing) to a corresponding collection reservoir that holds each of the output dispersions of separated small-scale objects. A collection plate has a discrete number of annular collection wells.

According to an embodiment of the current invention a passivated porous gel electrophoresis device is operated in a manner to separate two or more charged nanoscale objects dispersed in a solution based on a difference in said nanoscale objects in at least one of a shape, a maximum dimension, a minimum dimension, a dimension relative to a pore-size dimension of a gel, a surface charge density, a net surface charge, a surface charge group, a surface functionalization, an electrophoretic mobility, an interaction with a porous gel, an adsorption of a passivation agent, and an effective viscous friction factor.

According to an embodiment of the current invention, a rectangular slab of a passivated porous gel is used to separate two or more nanoscale objects in a first set of nanoscale objects that have been loaded into a loading well in said passivated porous gel based on differences in their electrophoretic mobilities in said passivated porous gel, wherein a first electric field is created along a first Cartesian direction (e.g. x-direction) of said rectangular slab by applying a first voltage between a first set of two electrodes (e.g. Pt wires arranged parallel to each other just beyond opposite sides of said slab of said passivated porous gel in a manner to create said first electric field) so that said first set of nanoscale objects are separated spatially in said passivated porous gel along said first Cartesian direction after a certain first time period of application of said first electric field. Subsequently, said first electric field is turned off, and a second electric field is applied along a second Cartesian direction (e.g. z-direction) that is normal to said first Cartesian direction (e.g. by a pair of Pt wires or Pt plates that are arranged parallel to each other and on opposite sides of said slab in a manner to create said second electric field). Said second electric field is applied for a duration in time that is sufficient to cause electrophoretic propagation of predominantly all of said spatially separated first set of nanoscale objects out of said passivated porous gel along said second Cartesian direction into a set of separate fluidic receiving wells from which said spatially separated nanoscale objects can be collected individually from said set of separate fluidic receiving wells. In an alternative embodiment of the invention, a fluidic connection can supply a second set of nanoscale objects to be separated to said loading well, subsequent to collecting said separated first set of nanoscale objects, and the process of applying said first electric field for an identical first duration to cause substantially the same spatial separation of said second set of nanoscale objects, turning off said first electric field, applying said second electric field for a sufficient duration to cause electrophoretic propagation of all spatially separated second set of nanoscale objects for collection in receiving wells, in a cyclic manner.

According to an embodiment of the current invention, an annular slab of a passivated porous gel is used in an annular-cylindrical container geometry to separate two or more nanoscale objects in a first set of nanoscale objects that have been loaded into a loading well in said passivated porous gel, based on differences in their electrophoretic mobilities in said passivated porous gel. A first electric field is created along a radial direction (e.g. r-direction) of said rectangular slab by applying a first voltage between a first set of two electrodes (e.g. an inner Pt-wire electrode arranged as a smaller circular loop at the inner wall near the loading well and an outer Pt-wire electrode arranged as a larger circular loop near the outer wall; both Pt wires are in contact with buffer solution). Said first electric field exerts forces on charged nanoscale objects, causing said charged nanoscale objects to be separated spatially in said passivated porous gel along said radial direction after a certain first time period of application of said first electric field. Subsequently, said first electric field is turned off, and a second electric field is applied along an axial direction (e.g. z-direction) that is normal to said first electric field. Said second electric field is applied for a duration in time that is sufficient to cause electrophoretic propagation of predominantly all of said spatially separated first set of nanoscale objects out of said passivated porous gel into a set of separate fluidic receiving wells (e.g. which have an annular shape) from which said spatially separated nanoscale objects can be collected individually from said set of separate fluidic receiving wells. In an alternative embodiment of the invention, a fluidic connection can supply a second set of nanoscale objects to be separated to said annular loading well, subsequent to collecting said separated first set of nanoscale objects, and the process of applying said first electric field for an identical first duration to cause substantially the same spatial separation of said second set of nanoscale objects, turning off said first electric field, applying said second electric field for a sufficient duration to cause electrophoretic propagation of all spatially separated second set of nanoscale objects for collection in receiving wells, in a cyclic manner. This continuous-cyclic process is illustrated in FIG. 23 for a simple annular slab geometry of a passivated gel. This continuous-cyclic process is also illustrated in FIG. 24, wherein the annular solid passivated gel does not have a uniform slab thickness, but instead has a tapered slab thickness so that the thickness is smaller closer to the annular loading well and larger further away from the annular loading well. In FIG. 23, 231=an annular loading well, 232=a passivated gel, and 233=an annular collection well. In FIG. 24, 241=an annular loading well, 242=a passivated gel, and 243=an annular collection well. In FIGS. 23 and 24, the steps are: Step 1 (top panels): Load annular loading well with a volume of an input dispersion of nanoscale objects to be separated by a fluidic input line and pump; Step 2 (middle panels): Apply an electric field along the radial r-direction to cause electrophoretic propagation of said nanoscale objects (different sizes denoted by differently colored arrows) in a passivated gel at different velocities along said radial direction over a sufficiently long duration of time to yield spatially separated nanoscale objects; and Step 3: Remove said electric field along said radial r-direction and subsequently apply an electric field along the axial z-direction for a duration of time to cause electrophoretic propagation of all of said spatially separated nanoscale objects out of said passivated gel and into separate annular collection wells positioned in a manner to collect said separated nanoscale objects. These steps can be repeated to separate additional nanoscale objects into collection wells.

In an embodiment of the current invention, passivated gel electrophoresis for separating colloidal objects is employed in combination with a fluidic flow of a buffer solution through the passivated gel medium along a direction that is orthogonal to the direction of the applied electric field. Said fluidic flow provides a fluidic force on a colloidal object that does not depend on the charge properties of said colloidal object, whereas an electrophoretic force does depend on the charge properties of said colloidal object. Thus, an applied fluid flow (e.g. as can be produced by a fluidic flow produced by a fluidic pump and a fritted flow homogenizer) can cause a fluidic propagation of colloidal objects through a porous medium in a direction along at least a component of a fluid velocity of said applied fluid flow that is perpendicular to an applied electric field. Thus, a fluidic propagation of said colloidal object can be controlled independently of an electrophoretic propagation of said colloidal object. A combination of a fluidic fluid and an electric field provides an advantage of directing electrophoretically separated colloidal objects out of said passivated gel and into separate collection wells.

In an alternative embodiment of the current invention, a solid slab of a gel suitable for electrophoresis is moved in a buffer solution spatially by a mechanical actuator in a direction that is orthogonal to at least one of an applied electric field and an applied fluidic flow. Said mechanical actuator provides a means of moving said passivated gel in a manner that facilitates a separation of colloidal objects and a collection of colloidal objects that have been separated into a set of collection wells.

In an alternative embodiment of the current invention a solid shape of a passivated gel suitable for electrophoresis is fabricated by creating a spatial gradient in a gel concentration of a molten non-solid gel material in the presence of said depletion agent as said solid shape is being cast into an elastic solid using a rigid mold, thereby creating a spatial gradient in a pore size distribution that does not evolve in time after solidification of said solid shape of said passivated gel. Said time-independent gradient in said pore size distribution of said solid shape of said passivated gel is used to spatially Herein, the term "pore size distribution" is employed, as is common in the art of gel materials, yet it has been recognized that the interpretation of this term is not precisely defined. Various measures can be used to define the statistics of a porous material, such as an average and a standard deviation of a porosity, an average and a standard deviation of a pore volume, an an average and a standard deviation of a pore specific surface area, an average and a standard deviation of a pore diameter, an average and a standard deviation of a pore size of passage, and an average and a standard deviation of a density of a number of pores having at least a certain cross-sectional pore area per unit length that would permit passage of colloidal objects. In the herein discussion, as is common in the field, we refer to at least one of these characteristics when we use the terminology of "pore size distribution".

In an embodiment of the current invention, a passivated gel is used in combination with a computer-controlled feedback loop wherein a computer controls at least one of an electric field, a fluidic flow field, and a mechanical actuator to separate an input fluidic dispersion of a plurality of colloidal objects into at least two or more fluidic output streams of separated dispersions of colloidal objects based on a measured optical signal arising from at least one of optical scattering, absorption, and fluorescence from said colloidal objects.

Example 5: A Kit of Components and Software

We have shown that a customized kit can be added to an existing gel electrophoresis device in order to obtain accurate size distributions of dispersions of small-scale objects. This kit consists of the following: a PEG1000 passivation agent for passivating a gel; a customized comb for creating wells in a gel that have very thin design (e.g. about 50 µm); a light box and stand for providing uniform side lighting of the region where small-scale objects propagate in a gel; a digital camera, lens, and stand for imaging light scattered from small-scale objects in a gel; and a customized software package that enables time-lapse acquisition of background-subtracted movies of the scattered light from propagating particles in the gel and analyzes images of background-subtracted movies to obtain at least one of a mobility distribution and a size distribution of said small-scale objects using a method of deconvolution involving a point-spread function that has features which depend on at least one of a propagation distance, a time after applying an electric field, an applied electric field, a gel concentration, a passivation agent concentration, a pH of buffer solution, a dimension of a well, a particle volume fraction, a refractive index difference, a wavelength of detected light, an average pore size, and a viscosity of a buffer solution.

Other Embodiments of the Current Invention

We readily anticipate that the optical measurement of particles propagating in real-time can be extended to other methods of imaging the propagation of particles and molecules beyond light scattered from particles in the gel that are side-illuminated by white light emanating from a light box. These other methods include monochromatic illumination (including using laser illumination such as a scanned laser beam and a laser light sheet created by a cylindrical lens), detection of absorption of illuminating light by strongly absorbing particles, detection of longer-wavelength fluorescent light emitted from fluorescent particles and fluorescently labeled molecules that are illuminated by shorter-wavelength incident light where the shorter wavelength illuminating light is filtered out by a filter placed in front of the optical detector that permits the passage of fluorescent emitted light, detection of x-rays, and detection of emitted elementary particles (e.g. neutrons, beta particles, and alpha particles) if nanoparticles or labeled molecules contain certain radio-isotopes that emit such x-rays and emitted particles.

Likewise, we readily anticipate that magnetic fields can be used in place of electric fields for causing magnetically responsive small-scale objects (such as superparamagnetic nanospheres and nanoemulsion droplets containing ferrofluids) to propagate through a passivated gel at different rates, thereby enabling optical detection of size distributions. Since many such magnetically-responsive small-scale objects are optically absorbing, we anticipate that a camera can be used to image localized regions of absorption caused by magnetically-responsive small-scale objects (e.g. by positioning the light box underneath the electrophoresis apparatus so that the camera above the electrophoresis apparatus spatially captures the optical absorption caused by such small-scale objects).

It can be reasonably anticipated that other types of controlled micro- and nano-porous media, which have been treated with a passivation agent that inhibits particle binding, can be substituted for passivated agarose gels in performing passivated gel-EP. For instance, certain types of porous polymer gels (e.g. other than agarose), can require a crosslinking agent; yet, irrespective of the use of a crosslinking agent, such gels can be readily treated with a passivation agent and made suitable for passivated gel-EP. As a different example, open-pore foams that have highly controlled pore size distributions, for instance as are made by a process of solidification of an interconnected network of a solid material during a phase separation by spinodal decomposition, can be readily treated with a passivation agent and made suitable for passivated gel-EP. As yet a different example, highly controlled Shirasu porous glass (e.g. such as is made by SPG Tech Co., Ltd.) that has a pre-defined pore size distribution, can be treated with a passivation agent and made suitable for passivated gel-EP.

Such passivated porous glass structures can be especially useful for separating larger microscale colloidal objects. As yet a different example, certain poly-peptides or block poly-peptides are known to form porous hydrogels through self-assembly or directed-assembly; since these hydrogels can be charged through the types of peptides that make up their compositions, certain poly-peptide-based hydrogels can be self-passivating in regards to interactions with charged particles and do not always require the addition of a separate passivation agent.

In an embodiment of the current invention, it is desirable to add a refractive-index-modifying agent to said buffer solution that modifies a refractive index of said buffer solution in order to enhance scattering from at least one of colloidal particles or droplets. In an alternative embodiment of the current invention, it is desirable to add a refractive-index-modifying agent to said buffer solution that modifies a refractive index of said buffer solution in order to reduce scattering from said passivated gel.

In an embodiment of the current invention, said buffer solution does not create an attractive interaction between colloidal particles loaded into a device for performing separations or size distribution measurement using passivated gel-EP. It is commonly known that factors such as pH and concentrations of dissolved electrolytes in a solution can cause destabilization of colloidal particles in a dispersion, leading to aggregation of said colloidal particles. Such aggregation would necessarily preclude an accurate determination of a size distribution of said colloidal objects prior to such aggregation.

In an embodiment of the current invention, output light that emanates from particles in a device for performing passivated gel-EP and is detected by an imaging device has a wavelength that is longer than input light from an illumination source that is used to illuminate said particles. In such a case, which is useful for imaging fluorescent light from fluorescent molecules within colloidal particles or droplets, it is typically desirable for said imaging device to be equipped with a filter that filters out scattered light of the shorter wavelength. In certain cases, the illuminating light is ultraviolet light, and the detected fluorescent light is visible light.

In an embodiment of the current invention, the illuminating light source is at least one of incoherent and coherent monochromatic light, as can be produced by a laser or an optical parametric oscillator.

In an embodiment of the current invention, a gradient in a pore size distribution in a passivated gel is used in combination with a process of passivated gel-EP in order to facilitate separation of colloidal objects in a dispersion of colloidal objects. Said gradient in a pore size distribution in a passivated gel is typically used to increase the range of sizes of said colloidal objects that can be separated.

In an embodiment of the current invention, a non-linear velocity-electric field response of colloidal particles subjected to an electric field in a passivated gel is used to enhance a separation of said colloidal particles.

In an embodiment of the current invention, a computer-controlled fluidic feedback loop is used in combination with a passivated gel in performing passivated gel-EP. Said computer-controlled feedback loop is typically used to direct a subset of colloidal particles that have traveled through at least a portion of said passivated gel to a different pre-defined location in a passivated gel in order to enhance a separation power of a colloidal separation using said process of passivated gel-EP. In some instances, said computer-controlled feedback loop directs said subset of colloidal particles to a location in said passivated gel that is at a reduced distance to a loading well in said passivated gel.

It can be reasonably anticipated that a combination of two or more different molecular passivation agents, whether charged or uncharged, can be used to passivate a porous gel, making said gel suitable for passivated gel-EP.

In an embodiment of the current invention, casting a porous gel in the presence of a passivation agent modifies said porous gel in a manner that change at least one of a surface charge on solid structures of said porous gel, a steric repulsive layer on solid structures of said porous gel, and a pore size distribution of said porous gel.

In an embodiment of the current invention, a charged passivation agent serves to neutralize residual surface charge groups on surfaces of a porous gel structure, making said porous gel structure suitable for performing passivated gel-EP.

It can be reasonably anticipated that size distributions of dispersions of uncharged colloidal objects can be readily measured by first exposing said uncharged colloidal objects to a molecular charging agent, such as a charged amphiphilic surfactant (e.g. SDS), which imparts a charge onto at least a surface of said uncharged colloidal objects through a process such as surface adsorption, and then loading said uncharged colloidal objects that have been treated with said molecular charging agent into the passivated gel-EP device suitable for measuring size distributions. In some cases, it would be reasonable to add a concentration of said charged amphiphilic surfactant to the buffer solution in said passivated gel-EP device in order to maintain the imparted charge on the surfaces of said colloidal objects.

In an embodiment of the current invention, a porous polymer gel having a smaller average of a pore size distribution is cast in a solid porous glass structure having a larger average of a pore size distribution in order to form a solid porous polymer gel structure that is supported by said solid porous glass structure. At least one of said solid porous polymer gel structure and said solid porous glass structure are passivated by a passivation agent to make said solid porous polymer gel structure that is supported by said solid porous glass structure suitable for use in performing passivated gel electrophoresis of colloidal objects. An advantage of using a supported structure is that an average pore size of the polymer gel can be made larger than what is typically possible, since the rigidity of a slab of porous polymer gel tends to decrease as the average pore size increases.

In an embodiment of the current invention, an illumination source is placed proximate to a gel electrophoresis device to provide a transmission illumination rather than a side illumination. Said transmission illumination facilitates the imaging of optically absorbing particles that are separated during a process of gel electrophoresis. Said optically absorbing particles reduce an intensity of transmitted light, thereby creating a spatially varying intensity signal in an imaging device, which has been arranged to image transmitted light that is not absorbed by said optically absorbing particles. Thus, imaging transmitted light, not scattered light, through a gel containing optically absorbing particles undergoing electrophoresis can provide a an optical image signal that can be used to determine a size distribution from the reduction of intensity due to the presence of optically absorbing particles that have been electrophoretically transported to certain locations in a gel.

In an embodiment of the current invention, the particles to be separated can be in the form of a dispersion in a liquid material or liquid droplets as an emulsion. The liquid material must not cause aggregation of the particles or droplets (or coalescence of the droplets). For instance, having a liquid material at a pH that is unsuitable could cause particle aggregation after loading into the gel, which would then create problems for the separation or size distribution measurements.

In an embodiment of the current invention, the illuminating light can cause fluorescent light to be emitted from the particles, rather than scattered light. The propagating bands can be detected using at least one of scattered light, absorbed light, and fluorescent light.

In an embodiment of the current invention, Particles larger than about 10 μm can settle rapidly through sedimentation by gravitational forces. Smaller microscale and nanoscale objects will not settle gravitationally over the time periods required to perform the spatial separation by passivated gel-EP. Particles less than about 20 nm in diameter do not scatter light appreciably; the gel itself might scatter more. For sizes less than 20 nm, the light obtained may not be scattered light. It might be fluorescent light through an excitation using shorter wavelength light (e.g. UV) and a detection using longer wavelength light. A possible range likely suited for scattering is from about 20 nm in diameter to about 5 μm in diameter.

In some embodiments of the invention, any of the following agents can serve as a passivation agent: anionic amphiphilic molecules, cationic amphiphilic molecules, zwitterionic amphiphilic molecules, surface-modifying organofunctional alkoxysilane molecules, surface-modifying silicone polymer molecules, and surface-modifying polyether molecules.

In some embodiments, it can be reasonably anticipated that passivated gels of materials other than agarose can be formed in liquids other than water to be used in passivated gel electrophoresis. Other liquids, such as non-polar hydrocarbon liquids (e.g. vegetable oils, petroleum oils), silicone oils (e.g. poly-dimethylsiloxanes), and even fluorinated oils can be used in combination with a passivated gel in order to perform passivated gel electrophoresis.

In an embodiment of the current invention, the algorithm for determining a size distribution of small-scale particles can involve the following steps:

Step 1: Measure I(L), where L is a distance of propagation and I is a light intensity, for unknown distribution of particles propagating in a passivated gel during gel electrophoresis (GE) using scattered light imaging after background subtraction and after particles have propagated a time $t_{opt}$ that has enabled near-optimal spatial separation.

Step 2: Convert I(L) to I(a) using a known calibration obtained from prior GE experiments on particles having known sizes a, same shapes, and same charge characteristics.

Step 3: Convert I(a) to a smeared probability density as a function of effective radius a, $p^s_\phi(a)$, a measure of a size distribution, using a known calibration I($\phi$,a) obtained from prior GE experiments on particles having known sizes, same shapes, and same refractive index difference Δn.

Step 4: Perform a peak detection on $p^s_\phi(a)$ to determine the number, locations, and widths of resolvable peaks in the size distribution.

Step 5: Convolve a normalized point-spread function $f_{ps}$(a, δa) that has a variable width δa that depends on effective radius a, determined from a prior GE experiment using highly monodisperse particles, with an initial guess for the deconvolved size distribution $p^d_\phi(a)$, based on the peak detection results and a prior GE experiment of the characteristics of the widths and heights of point-spread functions for different a, for instance by using a direct method that is not based on Fourier transforms to obtain a convolved particle size distribution $p^C_\phi(a)$.

Step 6: Compare $p^C_\phi(a)$ to $p^s_\phi(a)$. If the total mean square error, given by chi-square, between these two functions is less than a certain acceptable error value, then stop and $p^d_\phi(a)$ is the final deconvolved size distribution. If not, then decrease values of $p^d_\phi(a)$ at a particular a if $p^C_\phi(a) > p^s_\phi(a)$ and increase values of $p^d_\phi(a)$ at a particular a if $p^C_\phi(a) < p^s_\phi(a)$ to obtain an updated $p^d_\phi(a)$.

Step 7: If necessary, repeat STEP 5 and STEP 6 until chi-square is below a certain acceptable error value and report the deconvolved size distribution $p^d_\phi(a)$.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A device for measuring at least one of mobility distributions and size distributions of colloidal objects, comprising:
   a gel electrophoresis component comprising a gel chamber that is suitable to receive a gel in which colloidal objects propagate in a liquid medium during operation;
   an illumination source arranged to illuminate said colloidal objects such that said colloidal objects absorb, scatter or emit light;
   an imaging device configured to obtain image data from said absorbed, scattered, or emitted light from said colloidal objects while said colloidal objects propagate through said gel; and
   a computing device configured to receive and process said image data to provide information concerning at least one of a mobility distribution and a size distribution of said colloidal objects,
   wherein said colloidal objects absorb, scatter or emit light from said illumination source with an intensity as a function of a spatial positioning of colloidal objects,
   wherein said colloidal objects is at least one of particles or droplets, and
   wherein said computing device is further configured to measure a size distribution of said at least one of particles or droplets from a spatial distribution of scattered light from said at least one of particles or droplets.

2. The device of claim 1, further comprising a gel disposed in said gel chamber, said gel being suitable to mediate propagation of said at least one of particles or droplets when said at least one of particles or droplets have an ensemble average maximum spatial dimension greater than 1 nm.

3. The device of claim 1, further comprising a gel disposed in said gel chamber, said gel being suitable to mediate propagation of said at least one of particles or droplets when said at least one of particles or droplets have an ensemble average maximum spatial dimension greater than 1 nm and less than about 10 μm.

4. The device of claim 1, wherein the illumination source is positioned along a side of the gel electrophoresis component.

5. A device for measuring at least one of mobility distributions and size distributions of colloidal objects, comprising:
- a gel electrophoresis component comprising a gel chamber that is suitable to receive a gel in which colloidal objects propagate in a liquid medium during operation;
- an illumination source arranged to illuminate said colloidal objects such that said colloidal objects absorb, scatter or emit light;
- an imaging device configured to obtain image data from said absorbed, scattered, or emitted light from said colloidal objects while said colloidal objects propagate through said gel; and
- a computing device configured to receive and process said image data to provide information concerning at least one of a mobility distribution and a size distribution of said colloidal objects,
- wherein said computing device is further configured to determine a point-spread function from said image data, and
- wherein said point spread function is determined by fitting a reversed log-normal function to said image data.

6. The device of claim 5, further comprising a gel disposed in said gel chamber, said gel being suitable to mediate propagation of said colloidal objects when said colloidal objects have an ensemble average maximum spatial dimension greater than 1 nm.

7. The device of claim 5, further comprising a gel disposed in said gel chamber, said gel being suitable to mediate propagation of said colloidal objects when said colloidal objects have an ensemble average maximum spatial dimension greater than 1 nm and less than about 10 μm.

8. A device for measuring at least one of mobility distributions and size distributions of colloidal objects, comprising:
- a gel electrophoresis component comprising a gel chamber that is suitable to receive a gel in which colloidal objects propagate in a liquid medium during operation;
- an illumination source arranged to illuminate said colloidal objects such that said colloidal objects absorb, scatter or emit light;
- an imaging device configured to obtain image data from said absorbed, scattered, or emitted light from said colloidal objects while said colloidal objects propagate through said gel;
- a computing device configured to receive and process said image data to provide information concerning at least one of a mobility distribution and a size distribution of said colloidal objects; and
- a gel disposed in said gel chamber, said gel being suitable to mediate propagation of said colloidal objects when said colloidal objects have an ensemble average maximum spatial dimension greater than 20 nm and less than about 5 μm,
- wherein said colloidal objects is at least one of particles or droplets.

9. The device of claim 8, wherein said computing device is further configured to determine distribution of sizes of said at least one of particles or droplets.

10. The device of claim 9, wherein said computing device is further configured to model said distribution of sizes of said at least one of particles or droplets.

11. The device of claim 10, wherein said model includes an adaptive asymmetric point-spread function to deconvolve mobility and size distributions.

12. The device of claim 8, wherein said gel is a passivated gel.

13. The device of claim 12, wherein a polymer or an amphiphilic surfactant is used as a passivating agent.

14. The device of claim 13, wherein the polymer is polyethylene glycol.

15. The device of claim 13, wherein the amphiphilic surfactant used is sodium dodecyl sulfate.

16. The device of claim 8, wherein said computing device is further configured to deconvolve said image data using a point spread function.

17. A device for measuring at least one of mobility distributions and size distributions of colloidal objects, comprising:
- a gel electrophoresis component comprising a gel chamber that is suitable to receive a gel in which colloidal objects propagate in a liquid medium during operation;
- an illumination source arranged to illuminate said colloidal objects such that said colloidal objects absorb, scatter or emit light;
- an imaging device configured to obtain image data from said absorbed, scattered, or emitted light from said colloidal objects while said colloidal objects propagate through said gel; and
- a computing device configured to receive and process said image data to provide information concerning at least one of a mobility distribution and a size distribution of said colloidal objects,
- wherein the illumination source emits white incoherent light.

18. The device of claim 17, further comprising a gel disposed in said gel chamber, said gel being suitable to mediate propagation of said colloidal objects when said colloidal objects have an ensemble average maximum spatial dimension greater than 1 nm.

19. The device of claim 17, further comprising a gel disposed in said gel chamber, said gel being suitable to mediate propagation of said colloidal objects when said colloidal objects have an ensemble average maximum spatial dimension greater than 1 nm and less than about 10 μm.

20. The device of claim 17, wherein said computing device is further configured to deconvolve said image data using a point spread function.

* * * * *